United States Patent
Kapinsky

(10) Patent No.: US 10,502,678 B2
(45) Date of Patent: Dec. 10, 2019

(54) SYSTEMS AND METHODS FOR PANEL DESIGN IN FLOW CYTOMETRY

(71) Applicant: Beckman Coulter, Inc., Brea, CA (US)

(72) Inventor: Michael Kapinsky, Pollenried (DE)

(73) Assignee: Beckman Coulter, Inc., Brea, CA (US)

(*) Notice: Subject to any disclaimer, the term of this patent is extended or adjusted under 35 U.S.C. 154(b) by 484 days.

(21) Appl. No.: 14/776,891

(22) PCT Filed: Mar. 14, 2014

(86) PCT No.: PCT/US2014/029400
§ 371 (c)(1),
(2) Date: Sep. 15, 2015

(87) PCT Pub. No.: WO2014/144826
PCT Pub. Date: Sep. 18, 2014

(65) Prior Publication Data
US 2016/0025621 A1    Jan. 28, 2016

Related U.S. Application Data

(60) Provisional application No. 61/791,492, filed on Mar. 15, 2013.

(51) Int. Cl.
*G01N 21/25*    (2006.01)
*G01N 15/14*    (2006.01)
*G01N 15/10*    (2006.01)

(52) U.S. Cl.
CPC ............ *G01N 21/255* (2013.01); *G01N 15/14* (2013.01); *G01N 15/1425* (2013.01);
(Continued)

(58) Field of Classification Search
CPC ............ G01N 21/255; G01N 15/1425; G01N 15/1434; G01N 15/14
See application file for complete search history.

(56) References Cited

U.S. PATENT DOCUMENTS 4,661,913 A * 4/1987 Wu .................... G01N 15/1456
356/442
5,073,497 A * 12/1991 Schwartz ........... G01N 15/1012
356/243.2

(Continued)

FOREIGN PATENT DOCUMENTS

CN    101669031 A    3/2010
JP    2003-083894 A    3/2003

(Continued)

OTHER PUBLICATIONS

Kapinsky, "Designing Panels for Multicolor Phenotyping", 1st US SINO Flow Cytometry Workshop, Shanghai, China, Apr. 23, 2012, pp. 1-59.*

(Continued)

*Primary Examiner* — Michele Fan
(74) *Attorney, Agent, or Firm* — Schwegman Lundberg & Woessner, P.A.

(57) ABSTRACT

Embodiments of the present invention encompass systems and methods for determining detection limits for various antibody-dye conjugates for flow cytometry. Exemplary techniques involve a linear superpositioning approach of spillover-induced enlargements of normally distributed measurement errors.

20 Claims, 85 Drawing Sheets

(52) U.S. Cl.
CPC . *G01N 15/1434* (2013.01); *G01N 2015/1006* (2013.01); *G01N 2015/1402* (2013.01); *G01N 2015/1477* (2013.01); *G01N 2201/12* (2013.01)

(56) References Cited

U.S. PATENT DOCUMENTS

| | | | | |
|---|---|---|---|---|
| 5,656,499 | A * | 8/1997 | Chupp | B01F 5/0453 422/63 |
| 6,228,652 | B1 * | 5/2001 | Rodriguez | G01N 15/14 356/335 |
| 2004/0119974 | A1 | 6/2004 | Bishop et al. | |
| 2004/0214171 | A1 * | 10/2004 | Yamashita | C12N 9/18 435/6.18 |
| 2005/0123549 | A1 * | 6/2005 | Payne | C07K 14/4727 424/178.1 |
| 2005/0170373 | A1 * | 8/2005 | Monforte | C12Q 1/6809 435/6.14 |
| 2006/0269970 | A1 * | 11/2006 | Paul | G01N 33/56966 435/7.21 |
| 2008/0194508 | A1 | 8/2008 | Christensen et al. | |
| 2009/0216478 | A1 * | 8/2009 | Estevez-Labori | G01N 15/1429 702/104 |
| 2009/0221005 | A1 * | 9/2009 | Kelleher | G01N 33/56972 435/7.24 |
| 2010/0028865 | A1 * | 2/2010 | Fazekas De St Groth | C12N 5/0636 435/6.16 |
| 2010/0120059 | A1 * | 5/2010 | Yan | G01N 21/6428 435/7.1 |
| 2010/0302536 | A1 * | 12/2010 | Ball | G01J 3/4406 356/317 |
| 2011/0204259 | A1 * | 8/2011 | Rogers | G01N 15/1429 250/459.1 |
| 2011/0282870 | A1 | 11/2011 | Herzenberg et al. | |
| 2011/0312511 | A1 | 12/2011 | Winquist et al. | |
| 2012/0056103 | A1 | 3/2012 | Sakai | |

FOREIGN PATENT DOCUMENTS

| | | |
|---|---|---|
| JP | 2011-085587 A | 4/2011 |
| WO | 2012/178166 A1 | 12/2012 |

OTHER PUBLICATIONS

Kapinsky, M., "Designing Panels for Multicolor Phentoyping," Beckman Coulter Flow Cytometry, 1st US SINO Flow Cytometry Workshop, Shanghai, China, Apr. 23, 2012, 59 pages.

Kapinsky, M., "Beyond Matching Dim Expression Densities with Bright Fluorochromes: A Novel Practical Approach to Design Multicolor Applications," Beckman Coulter Life Science, Inc., Krefeld, Germany, Poster, 2012.

Kapinsky, M., "Designing Panels for Multicolor Phenotyping," Beckman Coulter Flow Cytometry, Clinical Flow Symposium, Hong Kong Institute of Medicine Laboratory Sciences Ltd., Apr. 6-7, 2013, 57 pages.

International Search Report and Written Opinion dated Jul. 7, 2014 for PCT Patent Application No. PCT/US2014/029400, 11 pages.

Maecker, H., et al., "Selecting Reagents for Multicolor Flow Cytometry," BD Biosciences, Jun. 2012, 8 pages.

"FlowJo Panel Wizard," software product information, 2010, [online], [retrieved from the internet], <URL: http://www.flowjo.com/>, 4 pages.

Japanese Office Action dated Apr. 2, 2018 for JP Patent Application No. 2016-503083, with English Translation, 10 pages.

Chinese Office Action dated Jun. 2, 2017 for CN Patent Application No. 201480013742.6, English Translation, 20 pages.

European Office Action dated Dec. 12, 2017 for EP 14723573.3, 7 pages.

"Chinese Application Serial No. 201480013742.6, Office Action dated Sep. 4, 2019", W/English Translation, 7 pgs.

* cited by examiner

USER INPUT: SPECIFICITIES (SUCH AS CD57) ASSIGNED TO A SET OF PREDEFINED DYES

DETECTION CHANNELS

| FL9 | FL10 | FL1 | FL2 | FL3 | FL4 | FL5 | FL6 | FL7 | FL8 |
|---|---|---|---|---|---|---|---|---|---|
| 405 EXCITATION | | 488 EXCITATION | | | | | 633 EXCITATION | | |
| PACIFIC BLUE | KROME ORANGE | FITC | PE | ECD | PC5 | PC5.5 | PC7 | APC | APC-AF700 | APC-F750 |
| CD57 | CD45 | TDT | MPO | CD13 | DUMMY | CD33 | CD34 | CD79a | CD22 | CD19 |
| A74779 | A96416 | IM3524 | IM3455U | B24026 | CDS | A70198 | A21691 | A60793 | A89311 | A49681 |

EXAMPLE: CD57 (ANTIGEN) SHALL BE USED CONJUGATED TO PACIFIC BLUE (FLUOROCHROME, DYE); CD57-PacBlue IS CALLED A "CONJUGATE"; FL10 IS PacBlue'S PRIMARY CHANNEL, FL1-FL9 ARE SECONDARY CHANNELS THAT COULD DETECT UNWANTED SPILLOVER FLUORESCENCE FROM PacBlue EXAMPLE: DYES THAT ARE NOT INTENDED TO BE USED IN THE PANEL ARE ASSIGNED TO A "DUMMY" SPECIFICITY

EITHER PC5 OR PC5.5 IS USED (SPECIAL RULE FOR THIS COMBINATION OF DYES)

FIG. 1B

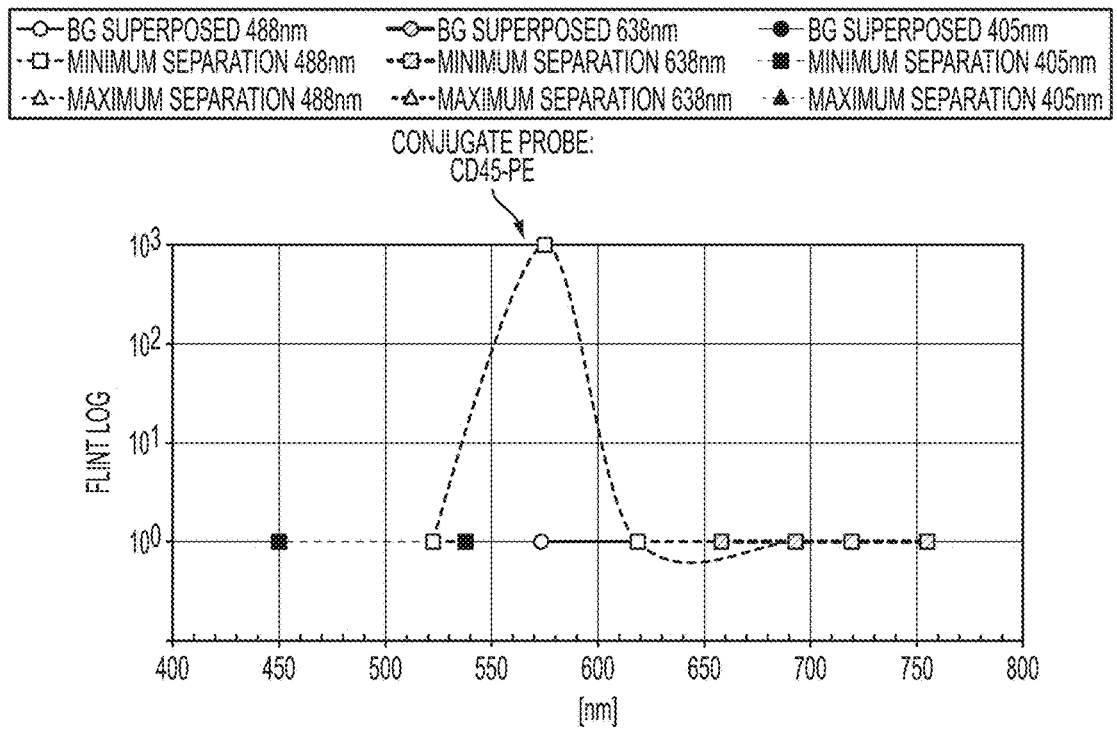
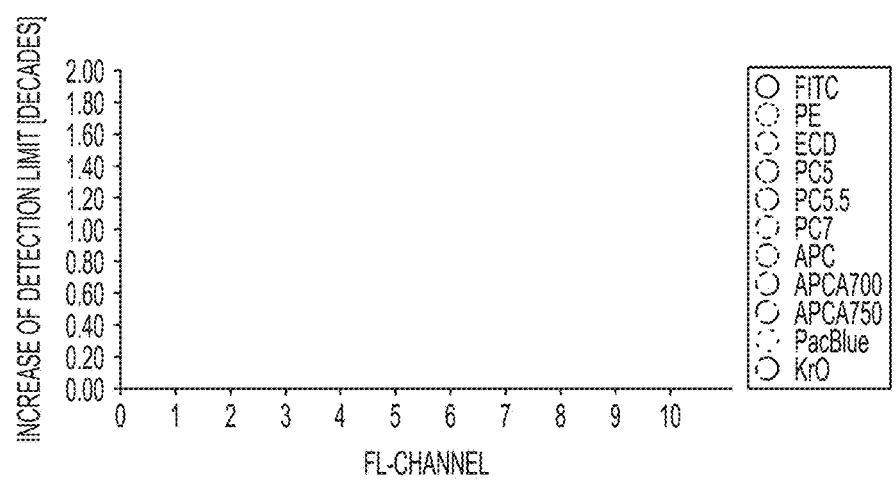
FIG. 1E

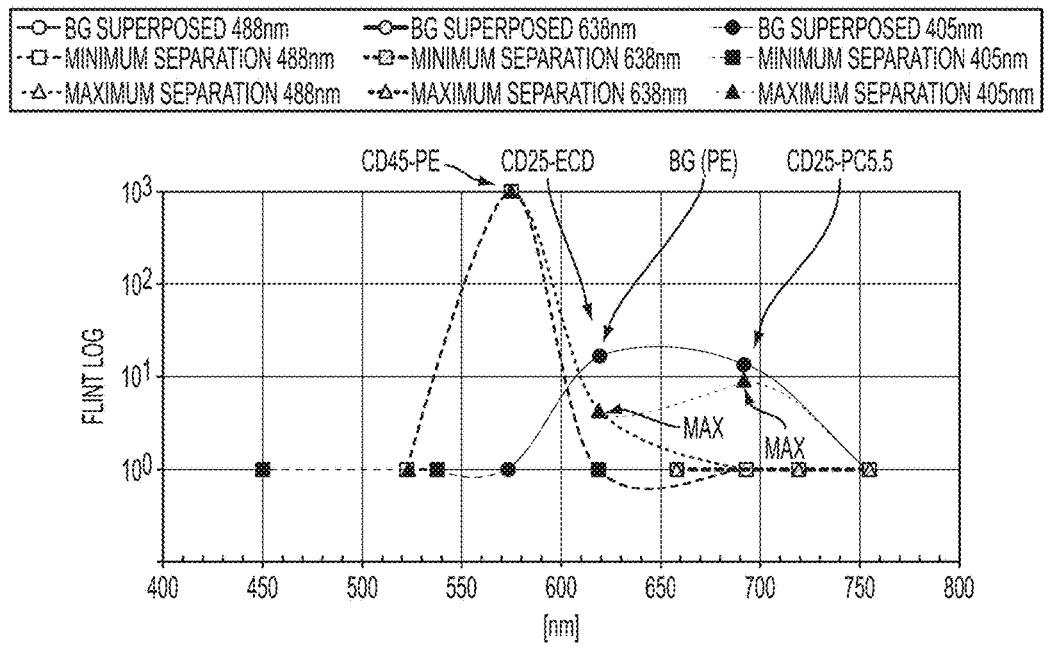
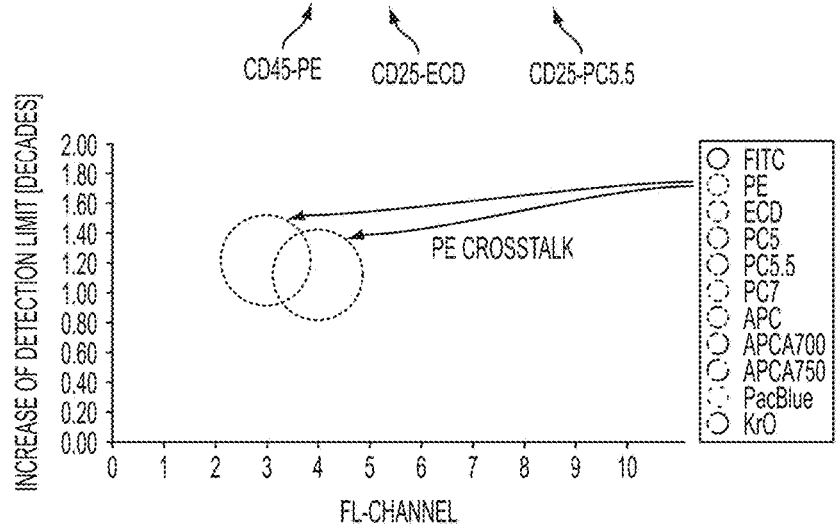
FIG. 1H

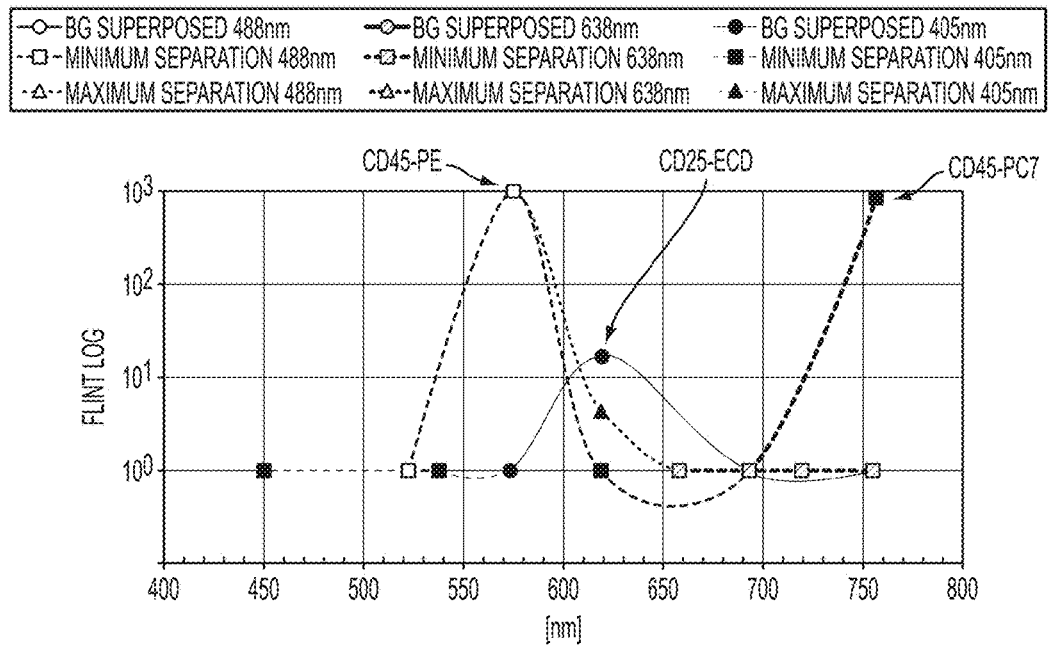
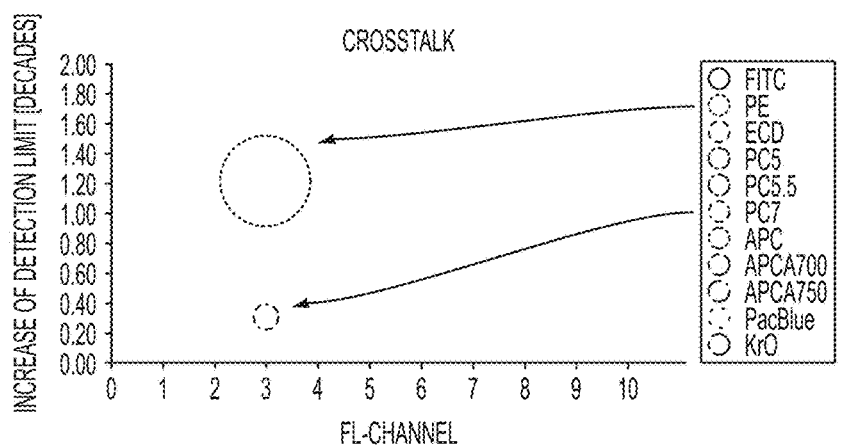
FIG. 1I

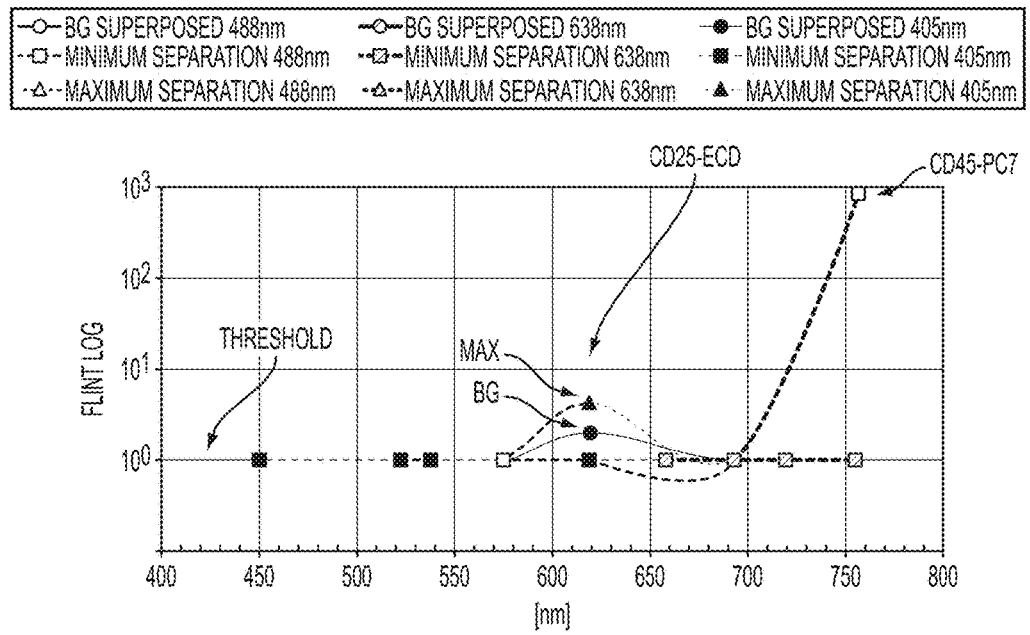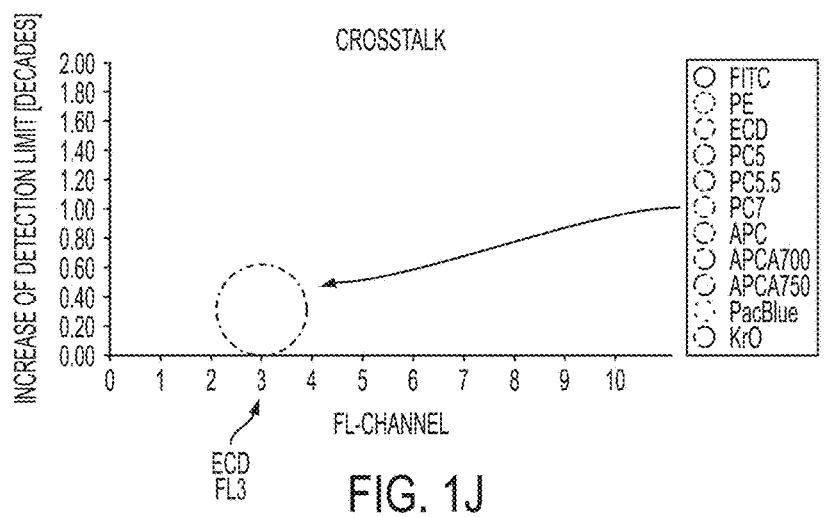
FIG. 1J

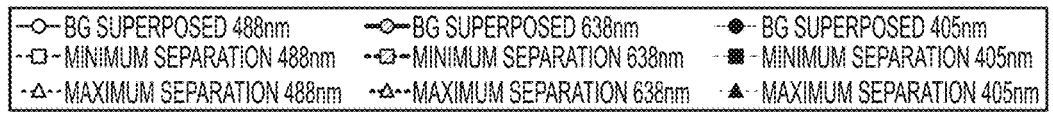
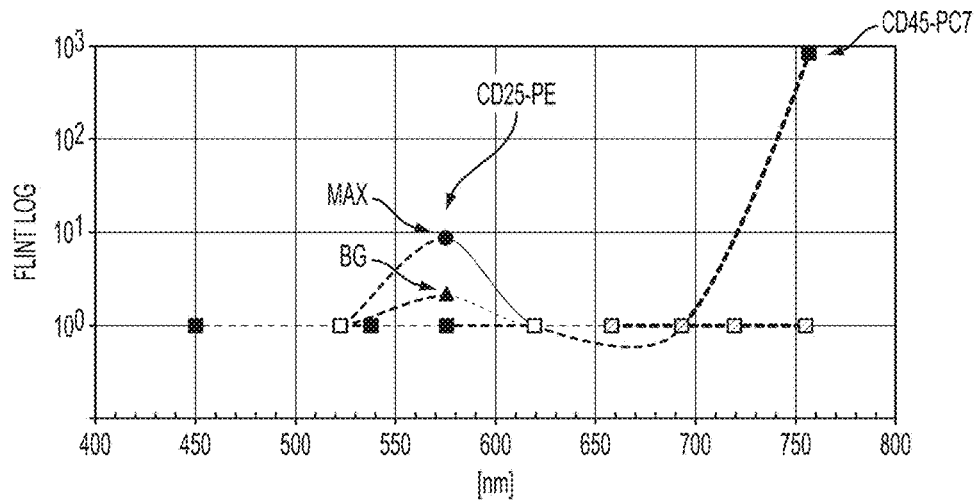
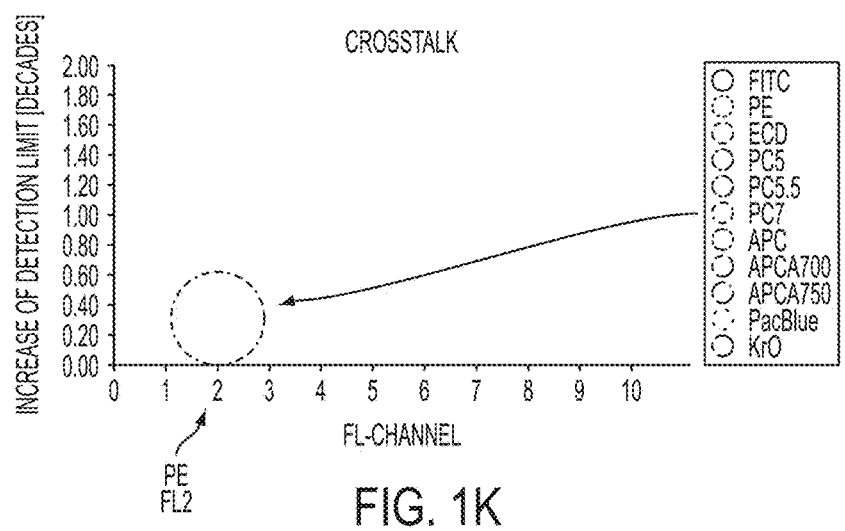
FIG. 1K

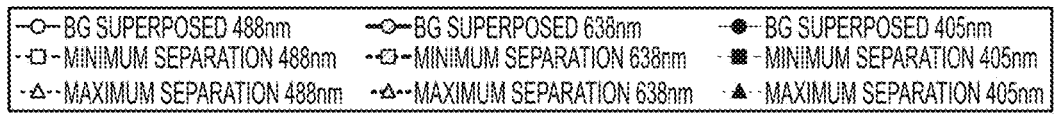
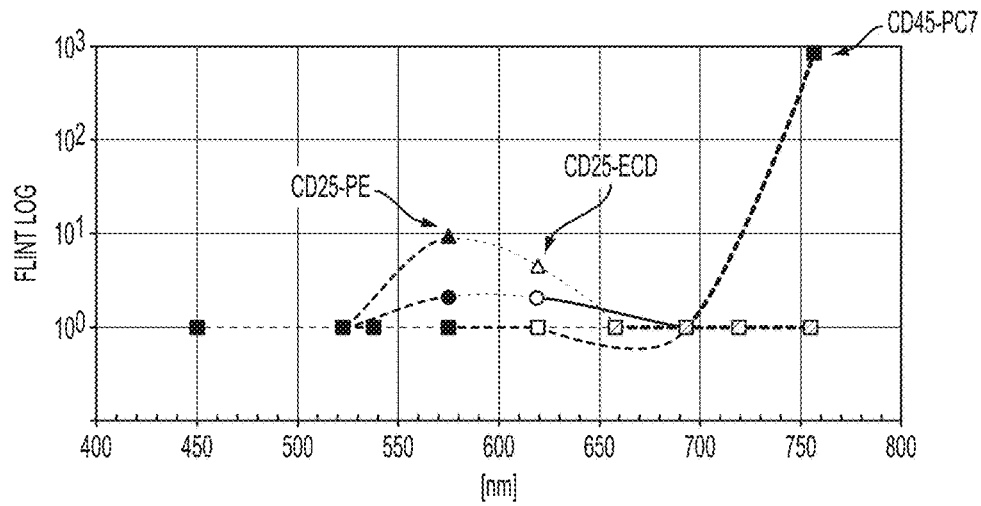
| 405 EXCITATION | | 488 EXCITATION | | | | | | 633 EXCITATION | | |
|---|---|---|---|---|---|---|---|---|---|---|
| PACIFIC BLUE | KROME ORANGE | FITC | PE | ECD | PC5 | PC5.5 | PC7 | APC | APC-AF700 | APC-F750 |
| DUMMY | DUMMY | DUMMY | CD25 | CD25 | DUMMY | DUMMY | CD45 | DUMMY | DUMMY | DUMMY |
| CDS | CDS | CDS | A89311 | A89311 | CDS | CDS | A74779 | CDS | CDS | CDS |
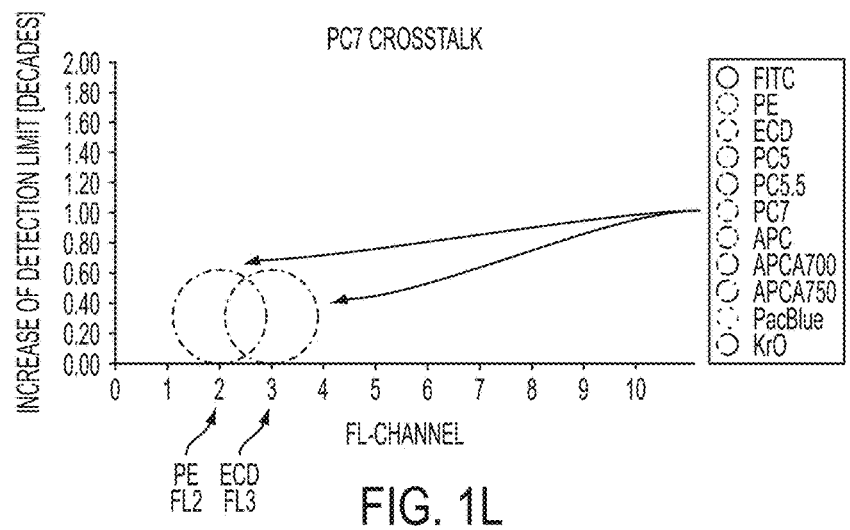
FIG. 1L

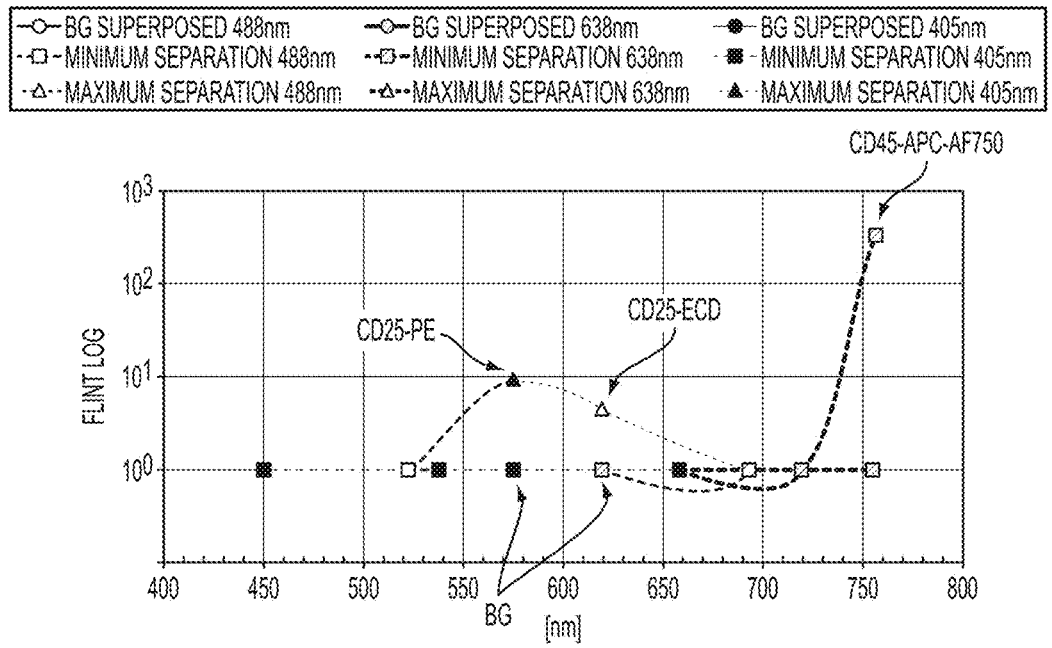
| 405 EXCITATION | | 488 EXCITATION | | | | | | 633 EXCITATION | | |
|---|---|---|---|---|---|---|---|---|---|---|
| PACIFIC BLUE | KROME ORANGE | FITC | PE | ECD | PC5 | PC5.5 | PC7 | APC | APC-AF700 | APC-F750 |
| DUMMY | DUMMY | DUMMY | CD45 | CD25 | DUMMY | DUMMY | DUMMY | DUMMY | DUMMY | CD45 |
| CDS | CDS | CDS | A89311 | A74779 | CDS | CDS | CDS | CDS | CDS | CDS |
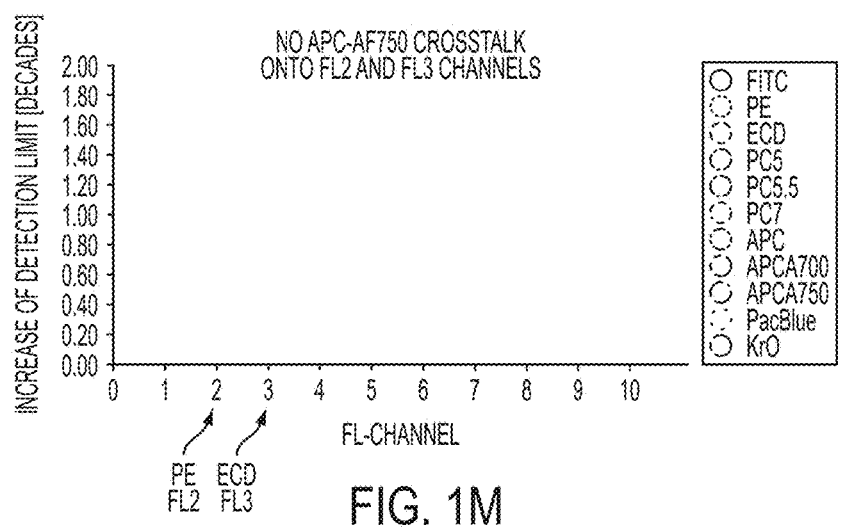
FIG. 1M

EXAMPLE FOR 3 CONJUGATES

| A-DYE (PRESET) | B-DYE (PRESET) | C-DYE (PRESET) |
|---|---|---|
| CDx | CDy | CDz |

USER INPUT

|  | MFI OF PE-conj. ABOVE 10^0 (DECADES) |
|---|---|
| CDx | 0.5 |
| CDy | 1 |
| CDz | 2.5 |

| MODULATED = 0 DISCRETE = 1 | ANTIGEN EXPRESSION CHARACTERISTICS |
|---|---|
| CDx | "1" |
| CDy | "0" |
| CDz | "1" |

DATABASE INFORMATION (COLOR CODES FACILITATE TRACKING OF CALCULATIONS BELOW)

| PARENT DESCENDANT | CDx | CDy | CDz |
|---|---|---|---|
| CDx | N.A. | 1 | 0 |
| CDy | 0 | N.A. | 1 |
| CDz | 1 | 1 | N.A. |

| COEXPRESSION OF INTEREST | CDx | CDy | CDz |
|---|---|---|---|
| CDx | N.A. | 1 | 0 |
| CDy | 1 | N.A. | 1 |
| CDz | 0 | 1 | N.A. |

FIG. 1N

| DISTORTION FACTORS | A-DYE | B-DYE | C-DYE |
|---|---|---|---|
| FL1 (DETECTOR FOR A-DYE) | N.A. | 0.25 | 0 |
| FL2 (DETECTOR FOR B-DYE) | 0.65 | N.A. | 0.1 |
| FL3 (DETECTOR FOR C-DYE) | 0 | 0.75 | N.A. |

| | RELATIVE INTENSITY AS COMPARED TO PE |
|---|---|
| A-DYE | 0.2 |
| B-DYE | 0.45 |
| C-DYE | 0.85 |

CALCULATIONS:

(I) FOR $CD_x$ = $LOG_{10}(((10^{\wedge}(0.5)-10^{\wedge}0) \times 0.2)+10^{\wedge}0)$;

(J) FOR $CD_y$ = 0 (MODULATED AS CODED BY "0")

FOR $CD_x$ = $LOG_{10}(((10^{\wedge}(0.5)-10^{\wedge}0) \times 0.2)+10^{\wedge}0)$ (DISCRETE AS AS CODED BY "1");

(K) FOR FL2: $K_1$ = $LOG_{10}((((10^{\wedge}(0.5)-10^{\wedge}0) \times 0.2)+10^{\wedge}0) *0.65 *1 *0$; NO INCREASE OF DL THROUGH $CD_x$ SPILLOVER $K_2$ = $LOG_{10}((((10^{\wedge}(.25)-10^{\wedge}0) \times 0.85)+10^{\wedge}0) *0.1 *1 *1$; INCREASE OF DL THROUGH $CD_z$ SPILLOVER (L) FOR FL2: = $LOG_{10}((10^{\wedge}(K_1)-10^{\wedge}0)+ (10^{\wedge}(K_2)-10^{\wedge}0))$;

FIG. 10

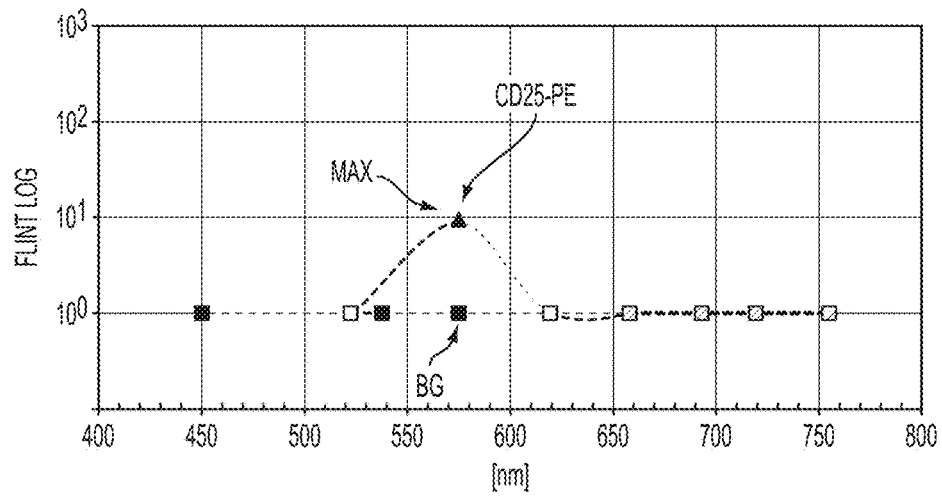
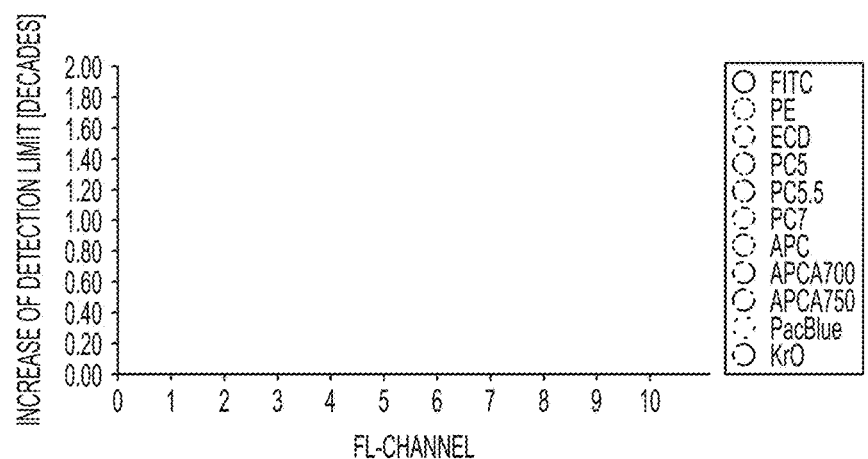
FIG. 1P

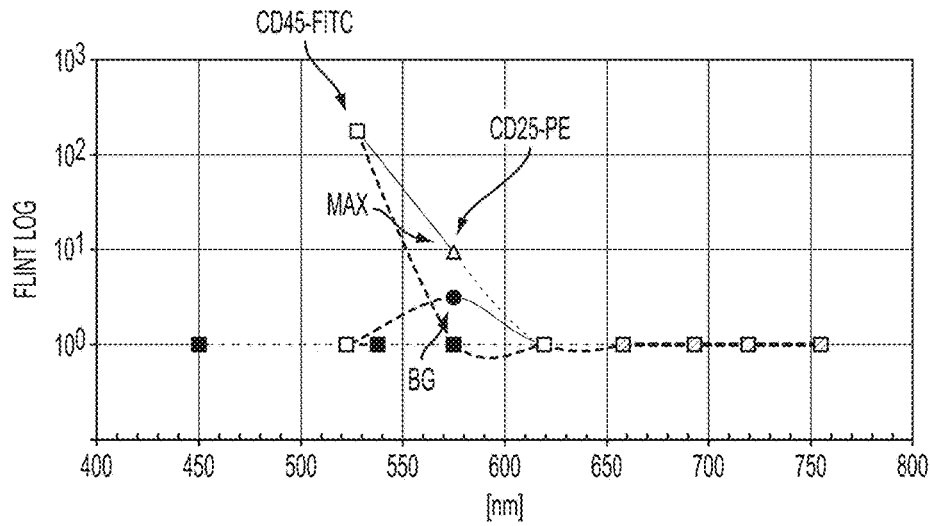
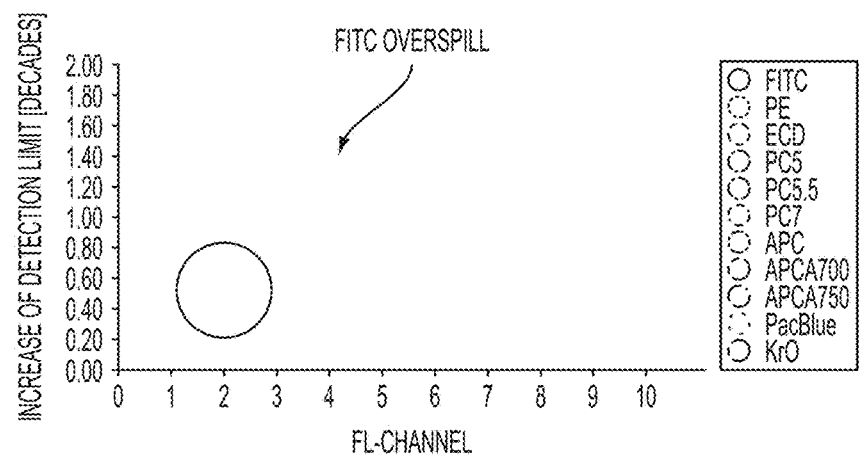
FIG. 1Q

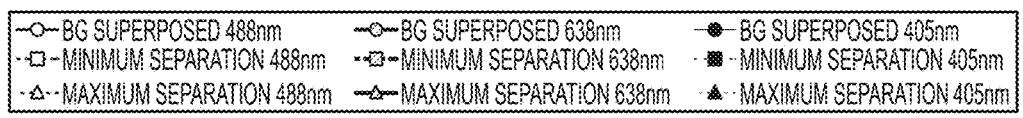
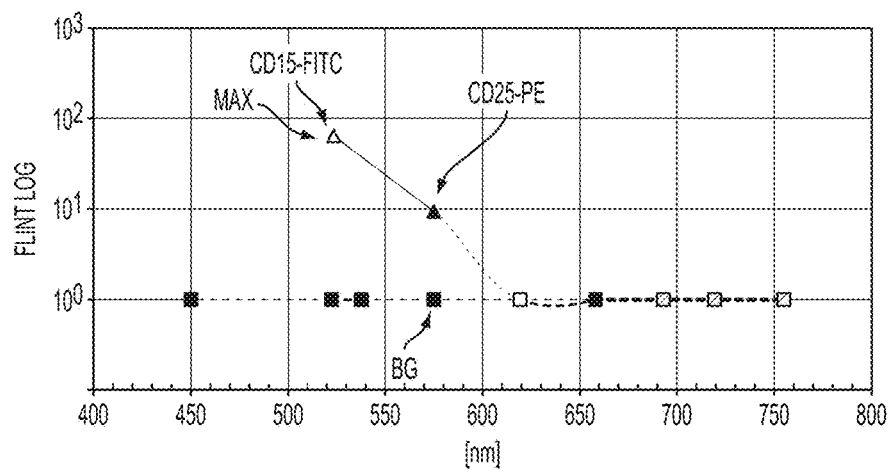
FIG. 1R

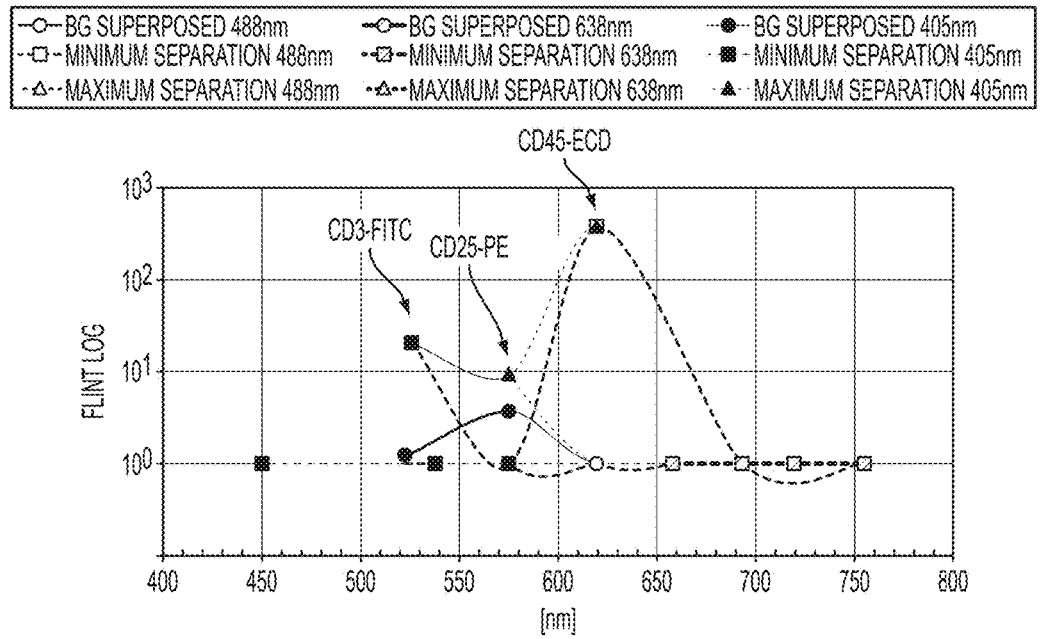
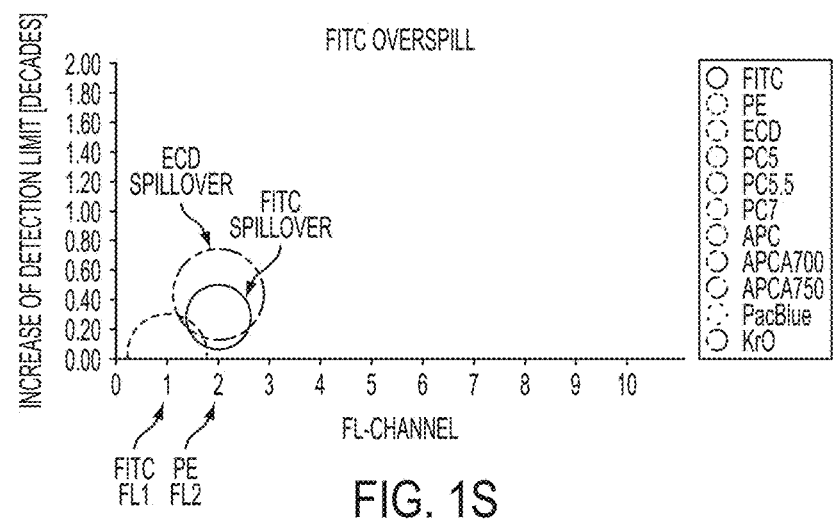
FIG. 1S

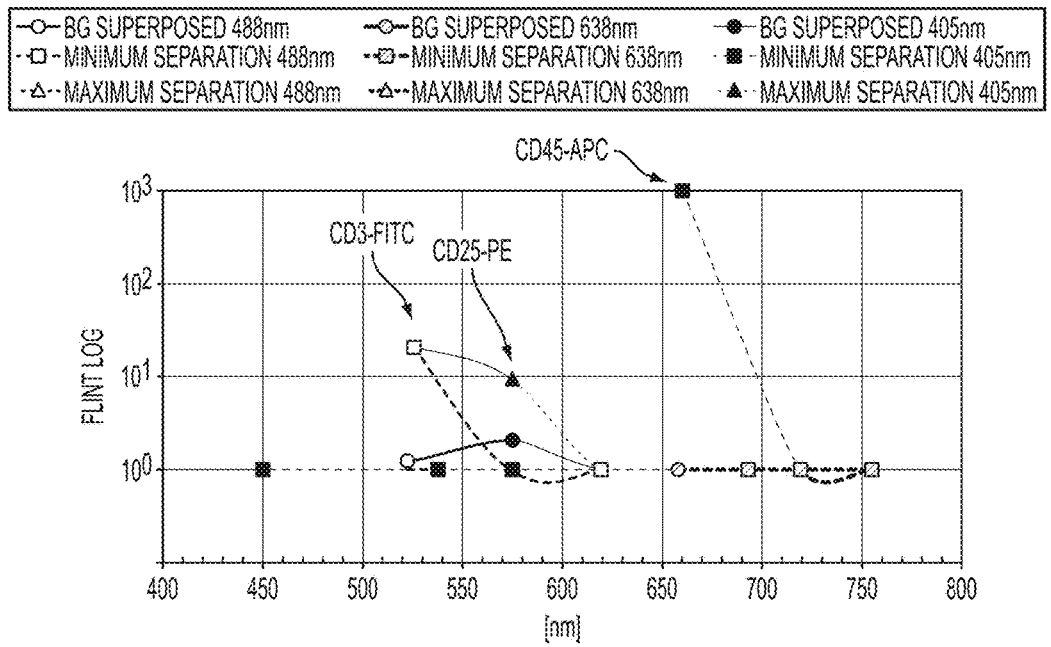
| 405 EXCITATION | | 488 EXCITATION | | | | | | 633 EXCITATION | | |
|---|---|---|---|---|---|---|---|---|---|---|
| PACIFIC BLUE | KROME ORANGE | FITC | PE | ECD | PC5 | PC5.5 | PC7 | APC | APC-AF700 | APC-F750 |
| DUMMY | DUMMY | CD03 | CD25 | DUMMY | DUMMY | DUMMY | DUMMY | CD45 | DUMMY | DUMMY |
| CDS | CDS | A74779 | A74779 | CDS | CDS | CDS | CDS | IM2472U | CDS | CDS |
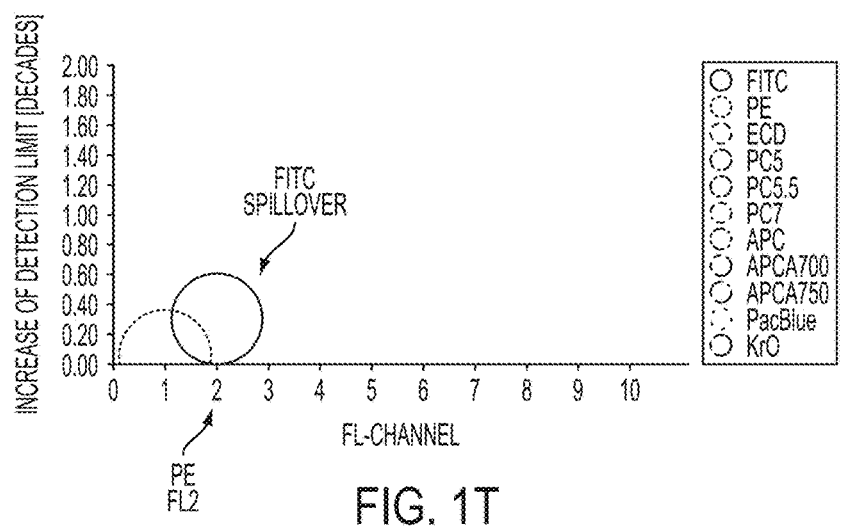
FIG. 1T

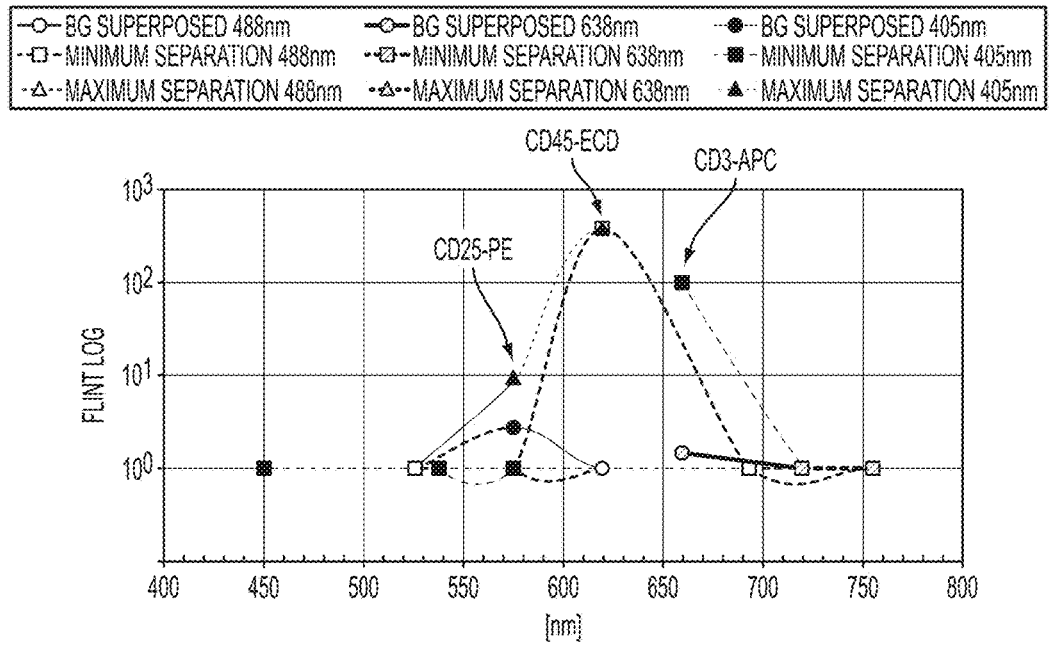
| 405 EXCITATION | | 488 EXCITATION | | | | | | 633 EXCITATION | | |
|---|---|---|---|---|---|---|---|---|---|---|
| PACIFIC BLUE | KROME ORANGE | FITC | PE | ECD | PC5 | PC5.5 | PC7 | APC | APC-AF700 | APC-F750 |
| DUMMY | DUMMY | DUMMY | CD25 | CD45 | DUMMY | DUMMY | DUMMY | CD3 | DUMMY | DUMMY |
| CDS | CDS | CDS | A32976 | A32976 | CDS | CDS | CDS | IM5467 | CDS | CDS |
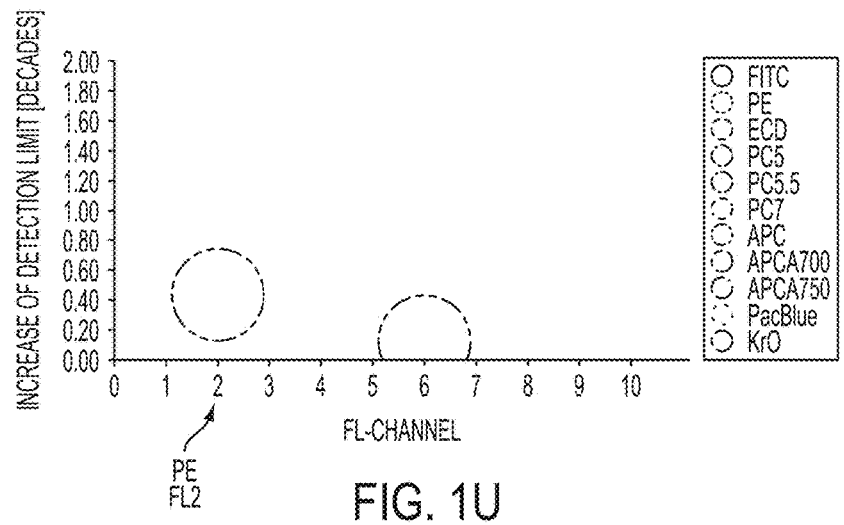
FIG. 1U

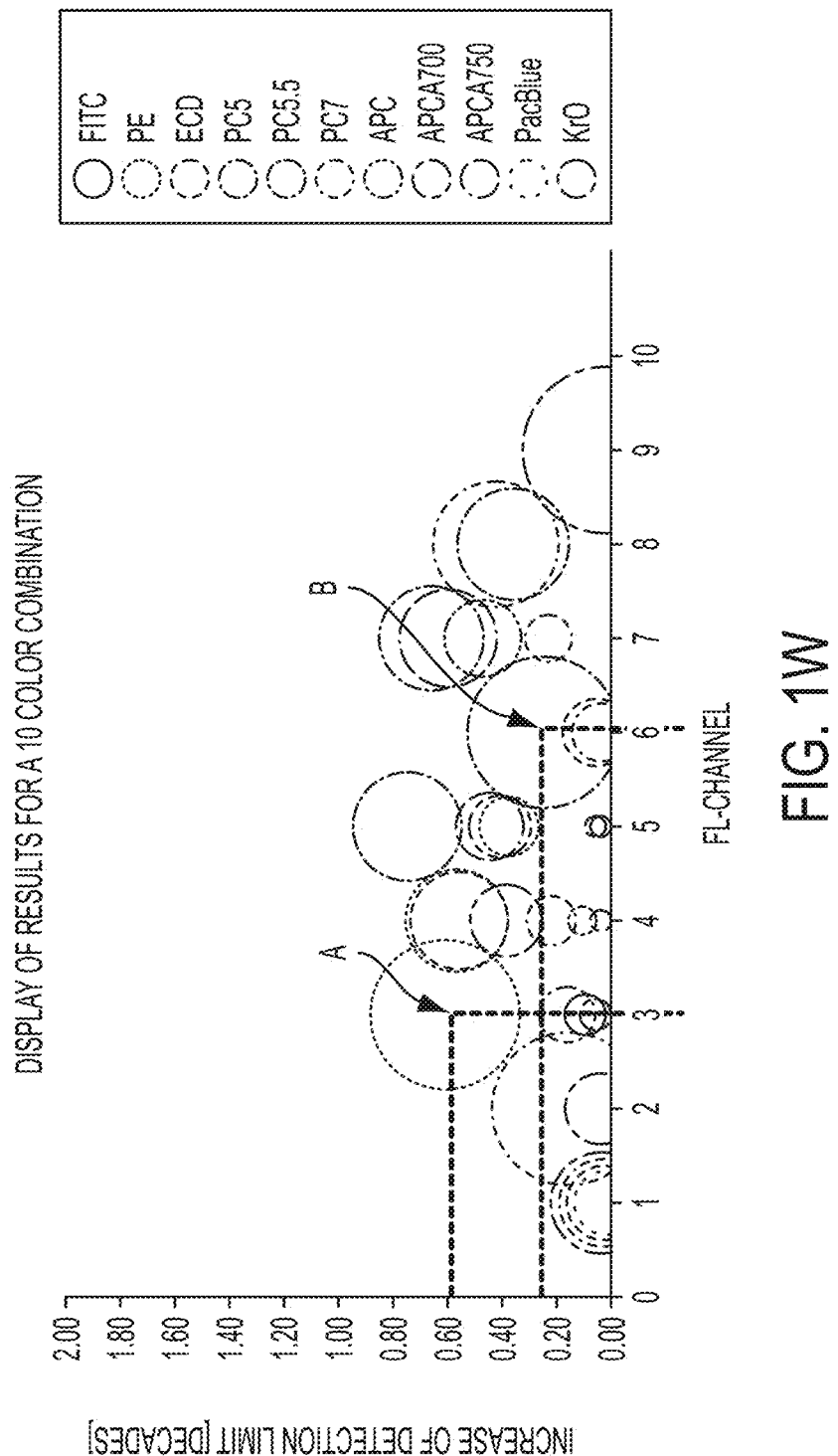

| | SKIP BUTTON<br>DO NOT SPECIFY PHENOTYPES |
|---|---|
| DROPDOWN PHENOTYPE INDEX (1,2,....,32) | |
| DROPDOWN (FORM 2) PHENOTYPE-RELATED ANTIBODY 1 | AUTOFILL (FORM 2) ANTIBODY 1-RELATED PRESELECTED DYE<br>(DEFAULT = NO DYE PRESELECTED) |
| DROPDOWN (FORM 2) PHENOTYPE-RELATED ANTIBODY 2 | AUTOFILL (FORM 2) ANTIBODY 2-RELATED PRESELECTED DYE<br>(DEFAULT = NO DYE PRESELECTED) |
| DROPDOWN (FORM 2) PHENOTYPE-RELATED ANTIBODY ... | AUTOFILL (FORM 2) ANTIBODY ...-RELATED PRESELECTED DYE<br>(DEFAULT = NO DYE PRESELECTED) |
| DROPDOWN (FORM 2) PHENOTYPE-RELATED ANTIBODY 14 | AUTOFILL (FORM 2) ANTIBODY 14-RELATED PRESELECTED DYE<br>(DEFAULT = NO DYE PRESELECTED) |
| DROPDOWN (FORM 2) PHENOTYPE-RELATED ANTIBODY 15 | AUTOFILL (FORM 2) ANTIBODY 15-RELATED PRESELECTED DYE<br>(DEFAULT = NO DYE PRESELECTED) |
| DROPDOWN ASSIGN PRIORITY RANKING (1,2,....,32) | |

FIG. 2A

|  |  | SKIP BUTTON<br>DO NOT SPECIFY EXCLUSIONS |
|---|---|---|
| DROPDOWN (FORM2) ANTIBODY SPECIFITY 1 | | DROPDOWN (FORM2) ANTIBODY SPECIFITY ...6 |
| DROPDOWN (FORM 2) EXCLUSION 1 | | DROPDOWN (FORM 2) EXCLUSION 1 |
| DROPDOWN (FORM 2) EXCLUSION 2 | | DROPDOWN (FORM 2) EXCLUSION 2 |
| DROPDOWN (FORM 2) EXCLUSION 3 | | DROPDOWN (FORM 2) EXCLUSION 3 |
| DROPDOWN (FORM 2) EXCLUSION ... | | DROPDOWN (FORM 2) EXCLUSION ... |
| DROPDOWN (FORM 2) EXCLUSION 9 | | DROPDOWN (FORM 2) EXCLUSION 9 |
| DROPDOWN (FORM 2) EXCLUSION 10 | | DROPDOWN (FORM 2) EXCLUSION 10 |

| | | 488 EXCITATION | | | | | | 633 EXCITATION | | | 405 EXCITATION | |
|---|---|---|---|---|---|---|---|---|---|---|---|---|
| | | FITC | PE | ECD | PC5 | PC5-5 | PC7 | APC | APC-AF700 | APC-AF750 | PACIFIC BLUE | KROME ORANGE |
| 488 EXCITATION | FITC | ░ | | | | | | | | | | |
| | PE | ○ | ░ | ∘ | | | | | | | | |
| | ECD | ○ | ○ | ░ | | | | | | | | |
| | PC5 | | ○ | ○ | ░ | ░ | | | | | | |
| | PC5-5 | | ○ | ○ | ░ | ░ | | | | | | |
| | PC7 | | ∘ | ○ | ○ | ○ | ░ | | | ∘ | | |
| 633 EXCITATION | APC | | | | ○ | ∘ | | ░ | ○ | ○ | | |
| | APC-AF700 | | | | ○ | ○ | | ○ | ░ | ○ | | |
| | APC-AF750 | | | | ∘ | ∘ | ○ | ∘ | ○ | ░ | | |
| 405 EXCITATION | PACIFIC BLUE | | | | | | | | | | ░ | |
| | KROME ORANGE | | | | | | | | | | ○ | ░ |

FIG. 10

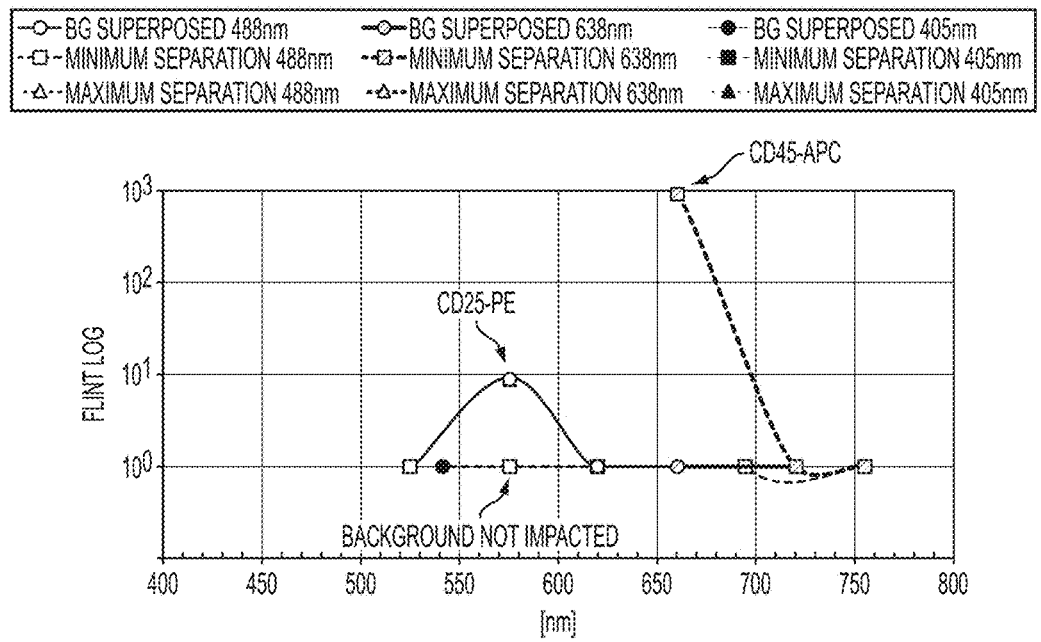
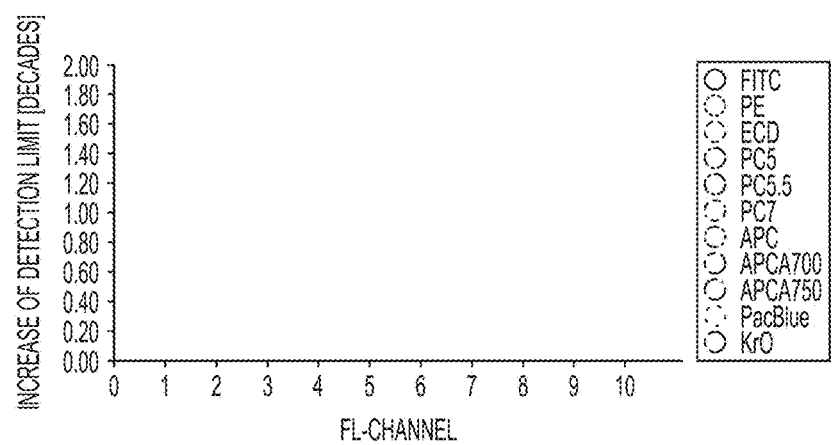
FIG. 12D

FIG. 13

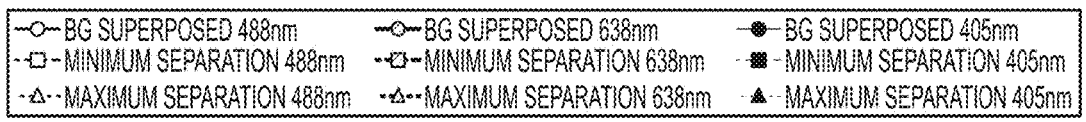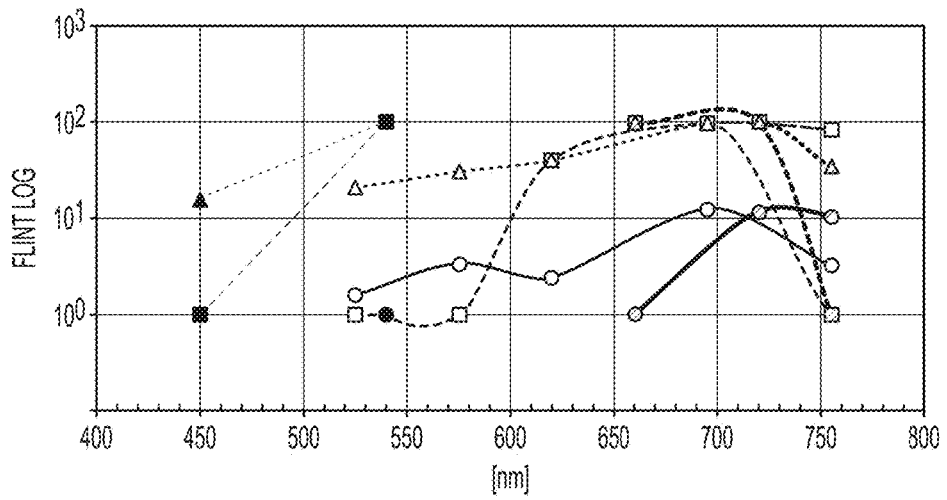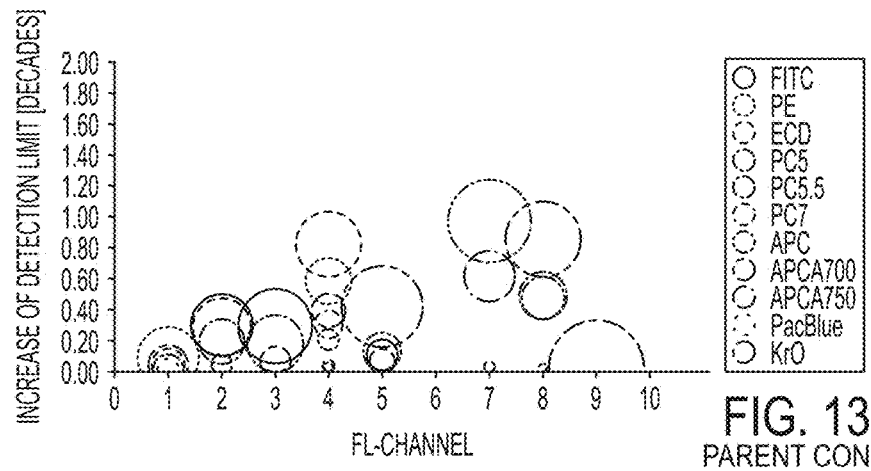
FIG. 13 PARENT CONT.

FIG. 14

| RELATIVE CONTRIBUTIONS (LOG) | | | | | | | | | | | |
|---|---|---|---|---|---|---|---|---|---|---|---|
| FL-CHANNEL | FITC | PE | ECD | PC5 | PC5.5 | PC7 | APC | APCA700 | APCA750 | PacBlue | KrO |
| 1 | 0.39 | 0.40 | 0.14 | 0.00 | 0.08 | 0.16 | 0.00 | 0.00 | 0.00 | 0.05 | 0.17 |
| 2 | 0.58 | 0.00 | 0.36 | 0.00 | 0.21 | 0.00 | 0.00 | 0.00 | 0.00 | 0.00 | 0.04 |
| 3 | 0.05 | 0.23 | 0.00 | 0.00 | 0.33 | 0.00 | 0.00 | 0.00 | 0.00 | 0.00 | 0.10 |
| 4 | 0.00 | 0.00 | 0.45 | 0.00 | 0.00 | 0.08 | 0.05 | 0.12 | 0.01 | 0.00 | 0.00 |
| 5 | 0.11 | 0.00 | 0.00 | 0.00 | 0.00 | 0.00 | 0.14 | 0.68 | 0.00 | 0.00 | 0.01 |
| 6 | 0.00 | 0.00 | 0.01 | 0.00 | 0.00 | 0.00 | 0.72 | 0.00 | 0.28 | 0.00 | 0.07 |
| 7 | 0.00 | 0.00 | 0.00 | 0.00 | 0.21 | 0.00 | 0.20 | 0.59 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 1.00 |
| 10 | 0.00 | 0.00 | 0.00 | 0.00 | 0.00 | 0.00 | 0.00 | 0.00 | 0.00 | 0.00 | 0.00 |

FIG. 14
PARENT CONT.

| RELATIVE BRIGHTNESS (APCA700 = 100%) | | INCREASE OF DETECTION LIMIT PER DECADE OF DISTORTING SIGNAL INTENSITY | | | | | | | | | | |
|---|---|---|---|---|---|---|---|---|---|---|---|---|
| | | FITC | PE | ECD | PC5 | PC5.5 | PC7 | APC | APCA700 | APCA750 | PacBlue | KrO |
| 0.2 | FITC | 0.00 | 0.06 | 0.02 | 0.01 | 0.01 | 0.02 | 0.00 | 0.00 | 0.00 | 0.01 | 0.02 |
| 0.95 | PE | 0.22 | 0.00 | 0.17 | 0.00 | 0.09 | 0.11 | 0.00 | 0.00 | 0.00 | 0.00 | 0.02 |
| 0.4 | ECD | 0.21 | 0.41 | 0.00 | 0.00 | 0.09 | 0.11 | 0.00 | 0.00 | 0.00 | 0.00 | 0.03 |
| 0.7 | PC5 | 0.00 | 0.00 | 0.00 | 0.00 | 0.00 | 0.00 | 0.00 | 0.00 | 0.00 | 0.00 | 0.00 |
| 0.95 | PC5.5 | 0.15 | 0.38 | 0.49 | 0.00 | 0.00 | 0.15 | 0.10 | 0.19 | 0.02 | 0.00 | 0.02 |
| 0.85 | PC7 | 0.07 | 0.25 | 0.39 | 0.00 | 0.50 | 0.00 | 0.06 | 0.20 | 0.28 | 0.00 | 0.03 |
| 0.95 | APC | 0.00 | 0.00 | 0.05 | 0.00 | 0.17 | 0.03 | 0.00 | 0.25 | 0.29 | 0.00 | 0.00 |
| 1 | APCA700 | 0.00 | 0.00 | 0.02 | 0.00 | 0.44 | 0.16 | 0.47 | 0.00 | 0.38 | 0.00 | 0.00 |
| 0.35 | APCA750 | 0.00 | 0.00 | 0.01 | 0.00 | 0.24 | 0.29 | 0.23 | 0.41 | 0.00 | 0.00 | 0.00 |
| 0.15 | PacBlue | 0.00 | 0.00 | 0.00 | 0.00 | 0.00 | 0.00 | 0.00 | 0.00 | 0.00 | 0.00 | 0.01 |
| 0.1 | KrO | 0.12 | 0.12 | 0.01 | 0.00 | 0.00 | 0.00 | 0.00 | 0.00 | 0.00 | 0.14 | 0.00 |

| LEVELS OF DISTORTION | IMPACT |
|---|---|
| 1/12 | ONLY RELEVANT IN CASE OF MID-STRONG TO VERY STRONG SIGNAL INTENSITIES |
| 2/15 | |
| 1/6 | |
| 1/4 | ALREADY RELEVANT IN CASE OF LOW-MID TO MID SIGNAL INTENSITIES |
| 1/3 | |
| 1/2 | ALREADY RELEVANT IN CASE OF LOW SIGNAL INTENSITIES |

FIG. 15

| 405 EXCITATION | | 488 EXCITATION | | | | | | 633 EXCITATION | | |
|---|---|---|---|---|---|---|---|---|---|---|
| PACIFIC BLUE | KROME ORANGE | FITC | PE | ECD | PC5 | PC5.5 | PC7 | APC | APC-AF700 | APC-F750 |
| CD45 | CD45 | CD36 | CD59 | CD15 | DUMMY | DUMMY | CD3 | DUMMY | CD71 | DUMMY |
| A74765 | A96416 | IM0766U | | | | | 737657 | | A97051 | |

FIELDS FOR INPUT FOR SPECIFICITIES

FIG. 16B

CD59 ONLY AVIALABLE AS FITC CONJUGATE

| 405 EXCITATION | | 488 EXCITATION | | | | | | 633 EXCITATION | | |
|---|---|---|---|---|---|---|---|---|---|---|
| PACIFIC BLUE | KROME ORANGE | FITC | PE | ECD | PC5 | PC5.5 | PC7 | APC | APC-AF700 | APC-F750 |
| CD45 | CD45 | CD36 | CD59 | CD15 | DUMMY | DUMMY | CD3 | DUMMY | CD71 | DUMMY |
| A74765 | A96416 | IM0766U | CDS | CDS | CDS | CDS | 737657 | CDS | A97051 | CDS |

PART NUMBERS ACCORDING TO ANTIBODY DATABASE

FIG. 16C

| ANTIGEN | ...MAY BE COEXPRESSED WITH / COEXPRESSION MAY BE OF INTEREST | | | | | | | | | | |
|---|---|---|---|---|---|---|---|---|---|---|---|
| | CD36 | CD59 | CD15 | DUMMY | DUMMY | CD3 | DUMMY | CD71 | DUMMY | CD45 | CD45 |
| CD36 |  | 1 | 1 | 1 | 1 | 0 | 1 | 1 | 1 | 1 | 1 |
| CD59 | 1 |  | 1 | 1 | 1 | 1 | 1 | 1 | 1 | 1 | 1 |
| CD15 | 1 | 1 |  | 1 | 1 | 0 | 1 | 0 | 1 | 1 | 1 |
| DUMMY | 1 | 1 | 1 |  | 1 | 1 | 1 | 1 | 1 | 1 | 1 |
| DUMMY | 1 | 1 | 1 | 1 |  | 1 | 1 | 1 | 1 | 1 | 1 |
| CD3 | 0 | 1 | 0 | 1 | 1 |  | 1 | 0 | 1 | 1 | 1 |
| DUMMY | 1 | 1 | 1 | 1 | 1 | 1 |  | 1 | 1 | 1 | 1 |
| CD71 | 1 | 1 | 0 | 1 | 1 | 0 | 1 |  | 1 | 1 | 1 |
| DUMMY | 1 | 1 | 1 | 1 | 1 | 1 | 1 | 1 |  | 1 | 1 |
| CD45 | 1 | 1 | 1 | 1 | 1 | 1 | 1 | 1 | 1 |  | 1 |
| CD45 | 1 | 1 | 1 | 1 | 1 | 1 | 1 | 1 | 1 | 1 |  |

FIG. 16D

| ANTIGEN | ...(BRIGHT EXPRESSING) CELLS ARE *NOT* A DESCENDANT POPULATION OF | | | | | | | | | | |
|---|---|---|---|---|---|---|---|---|---|---|---|
| | KAPPA | LAMBDA | CD5 | DUMMY | CD79b | CD20 | CD10 | CD23 | CD19 | FMC7 | CD45 |
| KAPPA |  | 1 | 1 | 1 | 1 | 1 | 1 | 1 | 1 | 0 | 1 |
| LAMBDA | 1 |  | 1 | 1 | 1 | 1 | 1 | 1 | 1 | 0 | 1 |
| CD5 | 1 | 1 |  | 1 | 1 | 1 | 1 | 1 | 1 | 1 | 1 |
| DUMMY | 1 | 1 | 1 |  | 1 | 1 | 1 | 1 | 1 | 1 | 1 |
| CD79b | 1 | 1 | 1 | 1 |  | 1 | 1 | 1 | 1 | 0 | 1 |
| CD20 | 0 | 0 | 0 | 1 | 0 |  | 1 | 1 | 1 | 0 | 1 |
| CD10 | 1 | 1 | 1 | 1 | 1 | 1 |  | 1 | 1 | 1 | 1 |
| CD23 | 1 | 1 | 0 | 1 | 1 | 1 | 1 |  | 1 | 1 | 1 |
| CD19 | 0 | 0 | 1 | 1 | 0 | 0 | 1 | 0 |  | 0 | 1 |
| FMC7 | 0 | 0 | 1 | 1 | 0 | 0 | 1 | 1 | 1 |  | 1 |
| CD45 | 0 | 0 | 0 | 1 | 0 | 0 | 0 | 0 | 0 | 0 |  |

FIG. 16E

EFFECTIVE DISTORTION MATRIX
(LINEAR SUPERPOSITIONS, PARABOLIC FACTORS SET TO ZERO)

| FL-CHANNEL | FITC | PE | ECD | PC5 | PC5.5 | PC7 | APC | APCA700 | APCA750 | PacBlue | KrO | MAX | TOTAL | SUPERPOSED |
|---|---|---|---|---|---|---|---|---|---|---|---|---|---|---|
| 1 | 525.00 | 0.00 | 0.03 | 0.00 | 0.01 | 0.04 | 0.00 | 0.00 | 0.00 | 0.00 | 0.04 | 0.04 | 0.11 | 285 |
| 2 | 0.00 | 575.00 | 0.27 | 0.00 | 0.13 | 0.21 | 0.00 | 0.00 | 0.00 | 0.00 | 0.04 | 0.27 | 0.47 | 377 |
| 3 | 0.18 | 0.81 | 620.00 | 0.00 | 0.13 | 0.21 | 0.00 | 0.00 | 0.00 | 0.00 | 0.06 | 0.81 | 0.91 | 489 |
| 4 | 0.00 | 0.00 | 0.00 | 695.00 | 0.00 | 0.00 | 0.00 | 0.00 | 0.00 | 0.00 | 0.00 | 0.00 | 0.00 | 256 |
| 4 | 0.13 | 0.75 | 0.79 | 0.00 | 695.00 | 0.29 | 0.10 | 0.03 | 0.00 | 0.00 | 0.04 | 0.79 | 1.13 | 545 |
| 5 | 0.00 | 0.00 | 0.63 | 0.00 | 0.00 | 755.00 | 0.06 | 0.29 | 0.00 | 0.00 | 0.06 | 0.63 | 0.86 | 476 |
| 6 | 0.00 | 0.00 | 0.03 | 0.00 | 0.25 | 0.06 | 660.00 | 0.30 | 0.43 | 0.00 | 0.00 | 0.45 | 0.71 | 438 |
| 7 | 0.00 | 0.00 | 0.02 | 0.00 | 0.65 | 0.31 | 0.46 | 0.38 | 0.45 | 0.00 | 0.00 | 0.65 | 1.02 | 516 |
| 8 | 0.00 | 0.00 | 0.02 | 0.00 | 0.00 | 0.00 | 0.23 | 0.00 | 0.59 | 0.00 | 0.02 | 0.23 | 0.24 | 316 |
| 9 | 0.00 | 0.00 | 0.00 | 0.00 | 0.00 | 0.00 | 0.00 | 720.00 | 755.00 | 450.00 | 0.00 | 0.02 | 0.02 | 261 |
| 10 | 0.00 | 0.00 | 0.00 | 0.00 | 0.00 | 0.00 | 0.00 | 0.00 | 0.00 | 0.00 | 540.00 | 0.00 | 0.00 | 256 |

FIG. 16H

RELATIVE CONTRIBUTIONS (LOG)

| FL-CHANNEL | FITC | PE | ECD | PC5 | PC5.5 | PC7 | APC | APCA700 | APCA750 | PacBlue | KrO |
|---|---|---|---|---|---|---|---|---|---|---|---|
| 1 | | 0.00 | 0.26 | 0.00 | 0.12 | 0.32 | 0.00 | 0.00 | 0.00 | 0.00 | 0.31 |
| 2 | 0.00 | | 0.45 | 0.00 | 0.18 | 0.32 | 0.00 | 0.00 | 0.00 | 0.00 | 0.05 |
| 3 | 0.07 | 0.77 | | 0.00 | 0.05 | 0.09 | 0.00 | 0.00 | 0.00 | 0.00 | 0.02 |
| 4 | 0.00 | 0.00 | 0.00 | | 0.00 | 0.00 | 0.00 | 0.00 | 0.00 | 0.00 | 0.02 |
| 4 | 0.03 | 0.37 | 0.41 | 0.00 | | 0.08 | 0.02 | 0.07 | 0.00 | 0.00 | 0.01 |
| 5 | 0.00 | 0.00 | 0.52 | 0.00 | 0.00 | | 0.02 | 0.16 | 0.28 | 0.00 | 0.02 |
| 6 | 0.00 | 0.00 | 0.01 | 0.00 | 0.19 | 0.03 | | 0.33 | 0.44 | 0.00 | 0.00 |
| 7 | 0.00 | 0.00 | 0.05 | 0.00 | 0.37 | 0.11 | 0.20 | | 0.31 | 0.00 | 0.00 |
| 8 | 0.00 | 0.00 | 0.00 | 0.00 | 0.00 | 0.00 | 0.95 | 0.00 | | 0.00 | 0.00 |
| 9 | 0.00 | 0.00 | 0.00 | 0.00 | 0.00 | 0.00 | 0.00 | 0.00 | 0.00 | 1.00 | 0.00 |
| 10 | 0.00 | 0.00 | 0.00 | 0.00 | 0.00 | 0.00 | 0.00 | 0.00 | 0.00 | 0.00 | |

FIG. 16I

| RELATIVE BRIGHTNESS | | INCREASE OF DETECTION LIMIT PER DECADE OF DISTORTING SIGNAL INTENSITY | | | | | | | | | | |
|---|---|---|---|---|---|---|---|---|---|---|---|---|
| (APCA700 = 100%) | | FITC | PE | ECD | PC5 | PC5.5 | PC7 | APC | APCA700 | APCA750 | PacBlue | KrO |
| 0.2 | FITC | 0.00 | 0.06 | 0.02 | 0.01 | 0.01 | 0.02 | 0.00 | 0.00 | 0.00 | 0.01 | 0.02 |
| 0.95 | PE | 0.22 | 0.00 | 0.17 | 0.09 | 0.09 | 0.11 | 0.00 | 0.00 | 0.00 | 0.00 | 0.02 |
| 0.4 | ECD | 0.21 | 0.41 | 0.00 | 0.09 | 0.09 | 0.11 | 0.00 | 0.00 | 0.00 | 0.00 | 0.03 |
| 0.7 | PC5 | 0.15 | 0.38 | 0.49 | 0.00 | 0.00 | 0.15 | 0.10 | 0.19 | 0.02 | 0.00 | 0.02 |
| 0.95 | PC5.5 | 0.15 | 0.38 | 0.49 | 0.00 | 0.00 | 0.15 | 0.10 | 0.19 | 0.02 | 0.00 | 0.02 |
| 0.85 | PC7 | 0.07 | 0.25 | 0.39 | 0.45 | 0.50 | 0.00 | 0.06 | 0.20 | 0.28 | 0.00 | 0.03 |
| 0.95 | APC | 0.00 | 0.00 | 0.05 | 0.50 | 0.17 | 0.03 | 0.00 | 0.25 | 0.29 | 0.00 | 0.00 |
| 1 | APCA700 | 0.00 | 0.00 | 0.02 | 0.25 | 0.44 | 0.16 | 0.47 | 0.00 | 0.38 | 0.00 | 0.00 |
| 0.35 | APCA750 | 0.00 | 0.00 | 0.01 | 0.15 | 0.24 | 0.29 | 0.23 | 0.41 | 0.00 | 0.01 | 0.01 |
| 0.125 | PacBlue | 0.00 | 0.00 | 0.00 | 0.00 | 0.00 | 0.00 | 0.00 | 0.00 | 0.00 | 0.00 | 0.01 |
| 0.075 | KrO | 0.12 | 0.12 | 0.01 | 0.00 | 0.00 | 0.00 | 0.00 | 0.00 | 0.00 | 0.14 | 0.00 |

FIG. 16J

| ANTIGEN | HIGHEST RELATIVE DENSITY (CD8=3) | ...IS RATHER DISCRETE | P/N FITC | PE | ECD | PC5 | PC5.5 | PC7 | APC | APCA700 | APCA750 | PacBlue | KrO |
|---|---|---|---|---|---|---|---|---|---|---|---|---|---|
| 7.1 |  |  | CDS | IM3454U | CDS | CDS | CDS | CDS | CDS | CDS | CDS | CDS | CDS |
| CD1a | 0.5 | 0 | CDS | A07742 | CDS | IM3610 | CDS | CDS | IM3645 | CDS | CDS | CDS | CDS |
| CD2 | 0.5 | 0 | A07743 | A07744 | CDS | A07745 | CDS | A21689 | A60794 | CDS | CDS | CDS | CDS |
| CD3 | 1.5 | 1 | A07746 | A07747 | A07748 | A07749 | A66327 | 737657 | IM2467 | B10823 | A94680 | A93687 | B00068 |
| CD4 | 2 | 1 | A07750 | A07751 | 6604727 | A07752 | B16491 | 737660 | IM2468 | CDS | A94682 | A82789 | A96417 |
| CD5 | 2 | 1 | A08932 | A07753 | A33096 | A07754 | A70203 | A21690 | A60790 | A78835 | A78836 | A82790 | CDS |
| CD7 | 1.5 | 0 | A07755 | IM1429U | A70202 | IM3613 | CDS | A46526 | A97050 | A70201 | B16892 | B06499 | CDS |
| CD8 | 2.5 | 0 | A07756 | A07757 | B06467 | A07758 | A99019 | 737661 | IM2469 | A66332 | A94683 | A07758 | B00067 |
| CD9 | 1 | 1 | IM1755U | CDS | CDS | CDS | B16490 | CDS | CDS | CDS | B13649 | B09979 | CDS |
| CD10 | 1 | 0 | A07759 | A07760 | IM3608U | A07761 | CDS | A46527 | IM3633 | A86353 | A89310 | CDS | CDS |
| CD11a | 1.5 | 0 | IM0860U | IM1433U | CDS | CDS | CDS | CDS | CDS | CDS | CDS | CDS | CDS |
| CD11b | 2 | 0 | IM0530 | IM2581U | CDS | IM3611 | CDS | A54822 | A87782 | CDS | A97052 | B16891 | CDS |
| CD11c | 2 | 0 | CDS | IM1760 | CDS | IM3707 | B19719 | A80249 | B01680 | CDS | CDS | CDS | CDS |
| CD13 | 1.5 | 0 | IM0778U | A07762 | A33097 | A07763 | A79389 | A46528 | A87783 | CDS | CDS | CDS | CDS |
| CD14 | 2.5 | 0 | IM0645U | A07764 | IM2707U | A07765 | A70204 | A22331 | IM2580 | A99020 | A86052 | B00846 | B01175 |
| CD15 | 2.5 | 0 | IM1423U | IM1954U | CDS | IM2641U | CDS | CDS | CDS | A89312 | CDS | A74775 | B01176 |
| CD16 | 2.5 | 0 | IM0814U | A07766 | A33098 | A07767 | CDS | 6607118 | CDS | A78637 | A66330 | A82792 | B00069 |
| CD19 | 2 | 1 | A07768 | A07769 | A07770 | A07771 | A66328 | IM3628 | IM2470 | CDS | A94581 | A86355 | A96418 |

| ANTIGEN | 7.1 | CD1a | CD2 | CD3 | CD4 | CD5 | CD7 | CD8 | CD9 | CD10 | CD11a | CD11b | CD11c | CD13 | CD14 | CD15 | CD16 | CD19 |
|---|---|---|---|---|---|---|---|---|---|---|---|---|---|---|---|---|---|---|
| 7.1 | 1 | 0 | 1 | 0 | 0 | 0 | 0 | 0 | 0 | 0 | 1 | 1 | 0 | 1 | 1 | 1 | 0 | 0 |
| CD1a | 0 | 1 | 1 | 1 | 1 | 1 | 1 | 1 | 1 | 1 | 1 | 1 | 1 | 1 | 1 | 1 | 1 | 0 |
| CD2 | 1 | 1 | 1 | 1 | 1 | 1 | 1 | 1 | 1 | 0 | 1 | 0 | 1 | 0 | 0 | 0 | 1 | 0 |
| CD3 | 0 | 1 | 1 | 1 | 1 | 1 | 1 | 1 | 1 | 0 | 1 | 0 | 1 | 0 | 0 | 0 | 1 | 0 |
| CD4 | 0 | 1 | 1 | 1 | 1 | 1 | 1 | 0 | 1 | 0 | 1 | 0 | 1 | 1 | 1 | 0 | 1 | 0 |
| CD5 | 0 | 1 | 1 | 1 | 1 | 1 | 1 | 1 | 1 | 0 | 1 | 0 | 1 | 0 | 0 | 0 | 1 | 1 |
| CD7 | 0 | 1 | 1 | 1 | 1 | 1 | 1 | 1 | 1 | 1 | 1 | 1 | 1 | 0 | 0 | 0 | 1 | 0 |
| CD8 | 0 | 1 | 1 | 1 | 0 | 1 | 1 | 1 | 1 | 0 | 1 | 0 | 1 | 0 | 0 | 0 | 1 | 0 |
| CD9 | 0 | 1 | 1 | 1 | 1 | 1 | 1 | 1 | 1 | 1 | 1 | 1 | 1 | 1 | 1 | 1 | 1 | 1 |
| CD10 | 0 | 1 | 0 | 0 | 0 | 0 | 1 | 0 | 1 | 1 | 1 | 1 | 1 | 1 | 1 | 1 | 1 | 1 |
| CD11a | 1 | 1 | 1 | 1 | 1 | 1 | 1 | 1 | 1 | 1 | 1 | 1 | 1 | 1 | 1 | 1 | 1 | 1 |
| CD11b | 1 | 1 | 0 | 0 | 0 | 0 | 1 | 0 | 1 | 1 | 1 | 1 | 1 | 1 | 1 | 1 | 1 | 1 |
| CD11c | 0 | 1 | 1 | 0 | 0 | 0 | 1 | 0 | 1 | 1 | 1 | 1 | 1 | 1 | 1 | 1 | 1 | 1 |
| CD13 | 1 | 1 | 0 | 0 | 1 | 0 | 1 | 0 | 1 | 1 | 1 | 1 | 1 | 1 | 1 | 1 | 1 | 0 |
| CD14 | 1 | 1 | 0 | 0 | 1 | 0 | 0 | 0 | 1 | 1 | 1 | 1 | 1 | 1 | 1 | 1 | 1 | 0 |
| CD15 | 1 | 1 | 0 | 0 | 0 | 0 | 1 | 0 | 1 | 1 | 1 | 1 | 1 | 1 | 1 | 1 | 1 | 0 |
| CD16 | 0 | 1 | 1 | 0 | 1 | 0 | 1 | 1 | 1 | 1 | 1 | 0 | 1 | 0 | 0 | 1 | 1 | 1 |
| CD19 | 0 | 0 | 0 | 0 | 0 | 1 | 0 | 0 | 1 | 1 | 1 | 0 | 1 | 0 | 0 | 0 | 0 | 1 |

IMMUNOMONITORING....MAY BE COEXPRESSED WITH / COEXPRESSION MAY BE OF INTEREST

| 488 EXCITATION | | | | | | 633 EXCITATION | | | 405 EXCITATION | |
|---|---|---|---|---|---|---|---|---|---|---|
| FITC | PE | ECD | PC5 | PC5.5 | PC7 | APC | APC-AF700 | APC-AF750 | PACIFIC BLUE | KROME ORANGE |
| CD90 | CD34 | CD7 | DUMMY | CD19 | CD309 | CD117 | DUMMY | CD38 | HLA-DR | CD45 |
| IM1839U | A07776 | A70202 | 0 | A66328 | A64616 | IM3638 | 0 | A86049 | A74781 | A96416 |
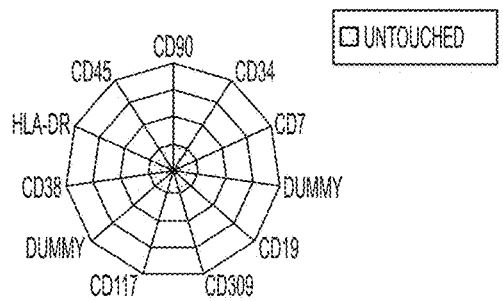
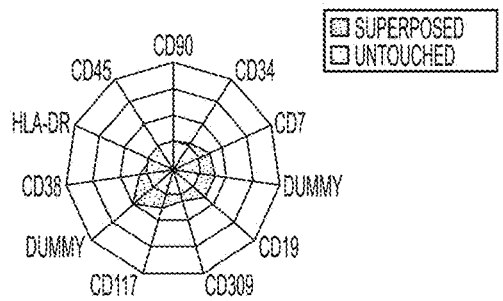
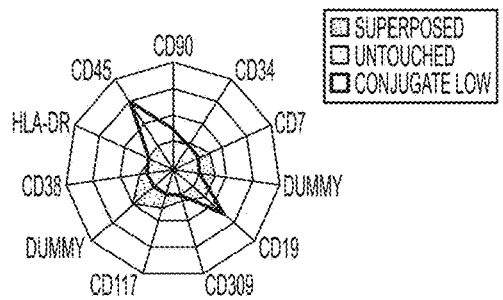
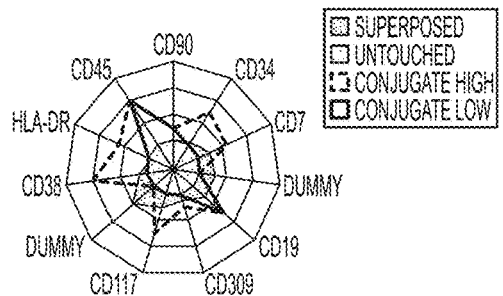
DETECTION RADAR
FIG. 17

DETECTION RADAR AND DISTORTION INDICATOR

CLONALITY SCREEN

CLONALITY SCREEN

FIG. 21B

|  | PacBlue | KrO | FITC | PE | ECD | PC5.5 | PC7 | APC | APCA700 | APCA750 |
|---|---|---|---|---|---|---|---|---|---|---|
| 450/40 | 0.00 | -0.01 | 0.00 | 0.00 | 0.00 | 0.00 | 0.00 | 0.00 | 0.00 | 0.00 |
| 540/40 | 0.10 | 0.00 | 0.08 | 0.08 | 0.01 | 0.00 | 0.00 | 0.00 | 0.00 | 0.00 |
| 525/40 | 0.00 | 0.01 | 0.00 | 0.04 | 0.01 | 0.00 | 0.01 | 0.00 | 0.00 | 0.00 |
| 575/30 | 0.00 | 0.01 | 0.16 | 0.00 | 0.13 | 0.07 | 0.08 | 0.00 | 0.00 | 0.00 |
| 620/30 | 0.00 | 0.02 | 0.17 | 0.34 | 0.00 | 0.07 | 0.09 | 0.00 | 0.00 | 0.00 |
| 695/30 | 0.00 | 0.02 | 0.14 | 0.35 | 0.45 | 0.00 | 0.14 | 0.09 | 0.18 | 0.02 |
| 755LP | 0.00 | 0.03 | 0.07 | 0.25 | 0.40 | 0.51 | 0.00 | 0.06 | 0.21 | 0.28 |
| 660/20 | 0.00 | 0.00 | -0.01 | 0.00 | 0.04 | 0.15 | 0.02 | 0.00 | 0.22 | 0.25 |
| 720/20 | 0.00 | 0.00 | -0.01 | 0.00 | 0.00 | 0.43 | 0.16 | 0.45 | 0.00 | 0.36 |
| 755LP | 0.01 | 0.00 | 0.00 | 0.00 | 0.01 | 0.25 | 0.30 | 0.24 | 0.42 | 0.00 |

FIG. 28

| 488 EXCITATION | | | | | | 633 EXCITATION | | | 405 EXCITATION | |
|---|---|---|---|---|---|---|---|---|---|---|
| FITC | PE | ECD | PC5 | PC5.5 | PC7 | APC | APC-AF700 | APC-AF750 | PACIFIC BLUE | PACIFIC ORANGE |
| CD62L | CD28-PE | CD45RA | | CD19 | CD27 | IgM | CD8 | CD45 | CD4 | CD3 |

FIG. 30

SYSTEMS AND METHODS FOR PANEL DESIGN IN FLOW CYTOMETRY

CROSS-REFERENCES TO RELATED APPLICATIONS

The present disclosure is a US National Phase of PCT Application No. PCT/US2014/029400, filed on Mar. 14, 2014 which claims priority to U.S. Provisional Patent Application No. 61/791,492 filed on Mar. 15, 2013, the disclosures of which are hereby incorporated by reference.

BACKGROUND OF THE INVENTION

Embodiments of the present invention relate generally to systems and methods for evaluating cells of a biological sample, and in particular to techniques for selecting antibody-dye conjugate combinations for use in flow cytometry. Further embodiments relate generally to automated systems and methods for analyzing positivity in multicolor flow cytometry.

Cell surface immunophenotyping using fluorescent flow cytometry has become a relatively routine process for differentiating and counting cells of interest in a cell sample containing many different cell types. Typically, cell surface probes, e.g., fluorochrome-labeled monoclonal antibodies (MABs) or other suitably labeled ligands, specific to antigens on the outer surface of the cells of interest, are used to selectively tag or "stain" such cells for subsequent detection. The flow cytometer operates to detect the stained cells by irradiating individual cells in the sample, one-by one, with radiation specially adapted to excite the fluorochrome labels. When irradiated, the labels fluoresce and their associated cells scatter the incident radiation in a pattern determined by the physical and optical characteristics of the irradiated cell. Suitable photo-detectors within the flow cytometer detect the scattered radiation and fluorescence, and their respective output signals are used to differentiate the different cell types on the basis of their respective light-scattering and fluorescence signatures.

Immunophenotyping by flow cytometry typically involves the selection of a set of probes or reagents physiologically appropriate for the desired evaluation or monitoring procedure. Relatedly, because certain disease conditions can be characterized by the expression of various antigens on the surface of cells or inside the cells of the patient, antibody probe reagent panels can be selected which correspond to such antigen profiles. For example, the Solastra™ 5-Color Reagent Panel is a panel of conjugated-antibody cocktails for use in characterizing hematolymphoid neoplasia by flow cytometry. The panel can be used to identification and enumerate relevant leukocyte surface molecules, and as aid in the differential diagnosis of patients with certain abnormal hematology results and/or presence of blasts in the blood stream, bone marrow, and/or lymphoid tissues. Solastrar® 5-Color Reagents are composed of antibodies directed to B, T, and Myelomonocytic lineage antigens. Such panels can be used in flow cytometric analyses for hematopathology applications.

The measurement of samples run through a flow cytometry device yields a characteristic photonic signature of scattered light, fluoresced light, or a combination thereof. By analyzing the signature, it is possible to infer physical and chemical characteristics of the particle. Often protein expression, a biological feature of an exemplary particle, is subject to the interrogation. The particle signatures from a sample of blood can be displayed in a dot plot, and gating can be used to interpret those signatures. Generally, gating is used to classify a signature as either positive or negative. For example, gating can be used to determine whether a particle is a blood cell or a piece of debris, or whether the blood cell contains a marker for disease. Hence, gating is important for diagnostic and clinical hematology applications. However, it can be difficult to determine whether a particle belongs to a positive or negative population, such as when the positive and negative signatures have a similar appearance. A variety of gating or specificity control techniques, such as isotype controls, models applying cluster analysis algorithms such as principal component analysis, and fluorescence minus one (FMO) have been proposed to help determine whether a particle should be classified as either positive or negative.

Although currently known antibody panel selection techniques provide many benefits to those who perform cell evaluation and monitoring procedures, still further improvements are desired. Further, gating control techniques to evaluate samples can be improved. Embodiments of the present invention provide solutions to at least some of these outstanding needs.

BRIEF SUMMARY OF THE INVENTION

Embodiments of the present invention encompass systems and methods for selecting and simulating antibody-dye conjugate panels for use in flow cytometry, and other related cellular evaluation and monitoring techniques. Often, such panels can be used or designed for evaluating cells of a biological sample. Such cells may be obtained from an individual person, from a cell culture, from a pool of human or non-human donors, or the like. According to some embodiments, the techniques disclosed herein can be used to evaluate any material that includes particles (e.g. biological cells) which are present in a suspension and which have structures on their surface or their inside that may be recognized by specific biological fluorochrome-labeled probes that non-covalently bind to these structures such as antibodies, toxins, receptor ligands, or derivatives thereof or similar compounds. As discussed elsewhere herein, exemplary probes, which may include fluorochrome-labeled monoclonal antibodies (MABs) or other suitably labeled ligands, can be specific to antigens on the outer surface of, or on the inside of, the cells of interest. Although difference sample preparation procedures may be used depending on whether the analysis involves external or internal antigens, the data acquisition techniques discussed here apply equally to either type of analysis. Suitable photo-detectors within the flow cytometer detect the scattered radiation and fluorescence, and their respective output signals are used to differentiate the different cell types (or subtypes of a certain cell type or different functional statuses among a certain type of cells) on the basis of their respective light-scattering and fluorescence signatures. These fluorescence signatures can be resolved computationally by a procedure referred to as fluorescence compensation thus delivering quantitative information on the presence of each interrogated single antigen on the surface or inside the cell/particle.

Multi-color immunophenotypic analysis using flow cytometry typically involves using panels or cocktails of antibody-dye conjugates. The panels can be configured so that individual probes, having respective individual dyes, correspond to individual color detection channels of a flow cytometry device. As discussed herein, the selection of probe panels can be automated, thus streamlining the multi-color flow cytometry analysis process. The use of such probe panels in flow cytometry can provide for the efficient acquisition of excellent quality data using multiple detection channels. Hence, downtime can be reduced and lab productivity can be maximized. Relatedly, embodiments of the present invention provide an improvement of sensitivity for the detection of prioritized antigens, and an enhanced facilitation of data analysis.

Exemplary flow cytometry devices may include various laser configurations (e.g. multiple solid state lasers) providing excitation spectra corresponding to red, blue, violet, yellow, and the like. Interchangeable optical filters can be used to facilitate the detection of a variety of dyes and wavelengths. Exemplary systems can be used for analyzing multiple fluorescent markers simultaneously. For example, systems having six fluorescence detectors can provide simultaneous acquisition of up to six fluorescence signals. Additional fluorescence detectors and/or lasers can be added to a system, enabling concurrent reading of up to ten or more colors. Embodiments of the present invention provide graphic display techniques for providing a user with plots, charts, and other visual features which can facilitate the analysis of complex flow cytometry data.

In one aspect, embodiments of the present invention encompass systems and methods of determining a probe panel for analyzing a biological sample in a flow cytometry procedure. Exemplary methods include inputting a flow cytometer hardware configuration, inputting a roster comprising a plurality of probes, where individual probes of the roster are associated with respective individual channel-specific detection limits, inputting an antigenic coexpression pattern, and determining the probe panel based on the flow cytometer hardware configuration, the individual channel-specific detection limits, and the antigenic coexpression pattern. The probe panel may include a subset of probes from the roster.

Further embodiments of the present invention encompass systems and methods for assessing positivity in multicolor flow cytometry. Exemplary specificity or gating control techniques can be used to evaluate an individual particle signature, for example to determine whether a blood cell is positive or negative for a certain protein expression, such as a disease marker. In some cases, these control techniques can be used to position a gate or graphical region relative to acquired data, so as to classify the cells from which the data is obtained. Exemplary control techniques can be used in multicolor procedures following compensation. In some cases, the methods disclosed herein provide for a level of standardization which is not present in currently used techniques. Moreover, the control techniques disclosed herein are time-efficient, economical, effective for heterogeneous expression patterns, and provide for the quantification of positives.

The above described and many other features and attendant advantages of embodiments of the present invention will become apparent and further understood by reference to the following detailed description when considered in conjunction with the accompanying drawings.

BRIEF DESCRIPTION OF THE DRAWINGS

Aspects of systems and methods according to embodiments of the present disclosure are described by the illustrations and figures set forth below.

FIG. 1B depicts aspects of a probe panel selection technique, according to some embodiments.

FIGS. 1E-1M depict aspects of a panel evaluation technique, according to embodiments of the present invention, according to some embodiments.

FIGS. 1N-1O depict examples for associations and calculations for three conjugates, to associate given CD with a given dye, according to some embodiments.

FIGS. 1P-1U depict further aspects of a panel evaluation technique, according to embodiments of the present invention, according to some embodiments.

FIGS. 1V-1W depicts aspects of displays for results for exemplary ten color probe panels, according to some embodiments.

FIG. 2A-2C depict operation selection features for target phenotype, phenotype exclusion, and parent/descendent schemes, respectively, according to some embodiments.

FIG. 2D depicts operation selection features for antigen density parameters, according to some embodiments.

FIG. 10 depicts aspects of an exemplary spillover pattern distortion matrix for certain dyes, according to some embodiments.

FIGS. 12A-12I depict schematics of estimated staining patterns, according to some embodiments.

FIG. 13 depicts aspects of probe panel evaluation including the categorization of expression patterns, according to some embodiments.

FIG. 14 depicts aspects of probe panel evaluation including relative fluorophore contribution, according to some embodiments.

FIG. 15 depicts aspects of probe panel evaluation including relative expression brightness of dyes, according to some embodiments.

FIGS. 16B-16C depict aspects of a user input module for a probe panel, according to some embodiments.

FIGS. 16D-16E depict aspects of simulator graphic modules for expression relationships in tabular form, according to some embodiments.

FIGS. 16H-16J depict aspects of a simulator numerics module for distortion calculations, according to some embodiments.

FIGS. 16M-16O depict aspects of an antibody database module, according to some embodiments.

FIG. 17 depicts aspects of a numerical approach to model spillover patterns including detection radar graphics for multivariate analysis, according to some embodiments.

FIGS. 21A-21B depict further aspects of a computerized interface for designing and simulating a probe panel, according to some embodiments.

FIG. 28 depicts an exemplary distortion table, according to some embodiments.

FIGS. 30-30A depict aspects of real data, plotting event data acquired from a flow cytometry instrument without applying gating to the data, according to some embodiments.

DETAILED DESCRIPTION OF THE INVENTION

Figure 1:
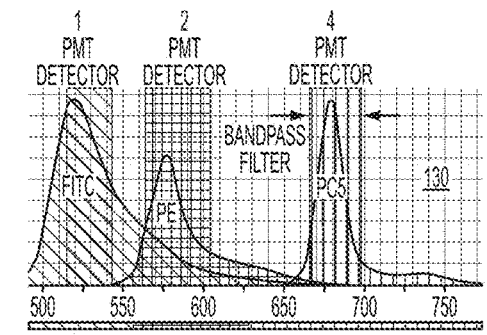
FIG. 1 depicts aspects of flow cytometry systems and methods according to some embodiments.

Flow cytometry often involves labeling a particle sample with fluorochrome dyes, and then evaluating properties of individual particles of the sample using various fluorescence detectors specific for various wavelengths. In this way, it is possible to obtain quantitative and qualitative data about the particle sample. For example, different cell surface receptors on a blood cell can be labeled with different fluorochrome dyes, and a flow cytometer can use separate fluorescence channels to detect the resulting light emitted. In exemplary embodiments, multiple excitation light wavelengths can be used in conjunction with multiple fluorochrome dyes and multiple fluorescence detectors, so as to simultaneously obtain several parameters of a sample. In particular embodiments, distortion factors resulting from the conjunctive use of multiple fluorochrome dyes and multiple fluorescence detectors can be quantified.

The term "event" as used herein can refer to a particle as it passes through a light beam, or the data or signature representing the particle. An event can be evaluated using multiple detectors, and each detector can provide respective intensity or signal parameter. Relatedly, each detector can be associated with a respective channel of the flow cytometer. For example, a measurement from an individual detector can be referred to as a parameter (e.g. forward scatter, side scatter, or fluorescence measured) and the data acquired in each parameter for a particle can be referred to as an event.

In some cases, a measured parameter may not reach a particular threshold for the detector channel, and hence may not register as an event. In this sense, the interaction between a light beam and a particle flowing through the cytometer may or may not produce a particle event. Optionally, such a threshold can be used to reduce or eliminate signals caused by noise, debris, and the like.

Embodiments of the present invention encompass systems and methods that involve determining detection limits of fluorescence signals in photomultipliers for use in flow cytometer applications. In some cases, the determination of a detection limit can be based on an expected expression pattern of a target cell (which can be labeled with antibody-fluorochrome conjugates), the expected fluorescence signal intensities for individual fluorescent labels arising from the fluorescent labeling of the antigens comprised by the expression pattern, and on an expected spillover matrix for the fluorochromes in the different photomultipliers.

According to some embodiments, there may be an additional input which encompasses the data spread that is specific for a given wavelength detection range (as determined by the bandpass filter in front of a photomultiplier) as the latter can determine the respective photomultiplier sensitivity and hence the measurement error (data spread). The relation between spillover and resulting data spread can be assessed experimentally.

Exemplary embodiments allow a cytometry device user to select a desired fluorochrome antibody combination (e.g. probe panel) which can be used to build flow cytometer experiments including a prediction of detection limits for the fluorochrome conjugates; this can also be referred to as a panel simulation. Furthermore, a cytometry device user may select a combination of antibodies without assigning fluorescent labels to each of these, respectively, in order to obtain a proposal for a probe panel with minimized detection limits for desired single probes within this probes panel. In some instances, panel evaluation or design techniques can involve the use of a linear superpositioning model of spillover-induced enlargements of normally distributed measurement errors.

Probe panel evaluation and design techniques as disclosed herein can use data from reference fluorochrome measurements with a single dye for calculations of a spillover (which can be alternatively referred to as overspill/overspilling, spilling, or crosstalk). In some cases, a distortion factor can be characterized by the following formula:

$$\frac{[\text{increase of the detecton limit in a non-primary channel}]}{[\text{intensity in the primary channel}][\text{decades}]}$$

In other words, the determination of a distortion factor can quantify the spillover effect of a first label (which is part of a probe-label conjugate), where the first label is intended or configured to be measured in a first channel (e.g. a PMT detector), into at least a second channel, where the second channel (or other additional channels) is intended and configured to measure a different label. In some aspects, the distortion factor can be an estimate of an increase in detection limit in the second channel as a function of an emission intensity of a first probe-label combination. In other aspects, the distortion factor can be a linear function of the emission intensity of a first probe-label combination. In further aspects, the distortion factor can be calculated using a crosstalk index. In some aspects, the distortion factor is mathematically modified by a coefficient representing the coexpression pattern of antigens corresponding to a first probe-label combination and a second probe-label combination, the second probe-label combination being intended or configured to be measured in a second channel. In further aspects, determining a distortion factor for each label in a first potential probe panel can be done to calculate a total increase in detection limit in a second channel.

Figure 1A:
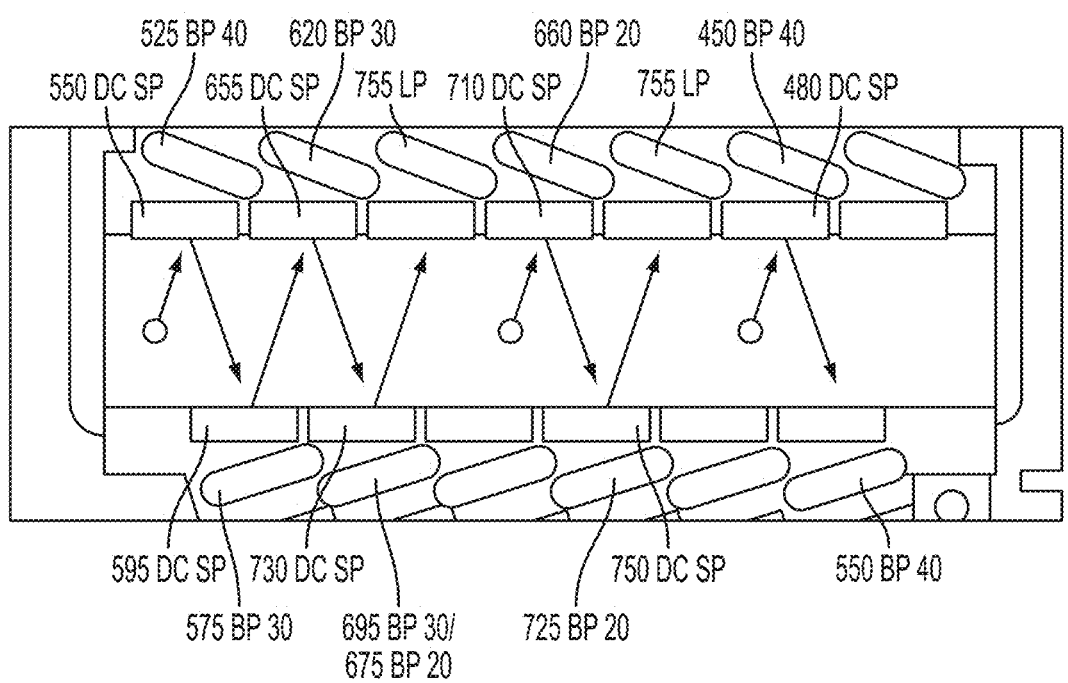
FIG. 1A depicts an exemplary hardware illustration of a flow cytometry device, having a three laser, ten color filter block configuration, according to some embodiments.
Figure 1C:
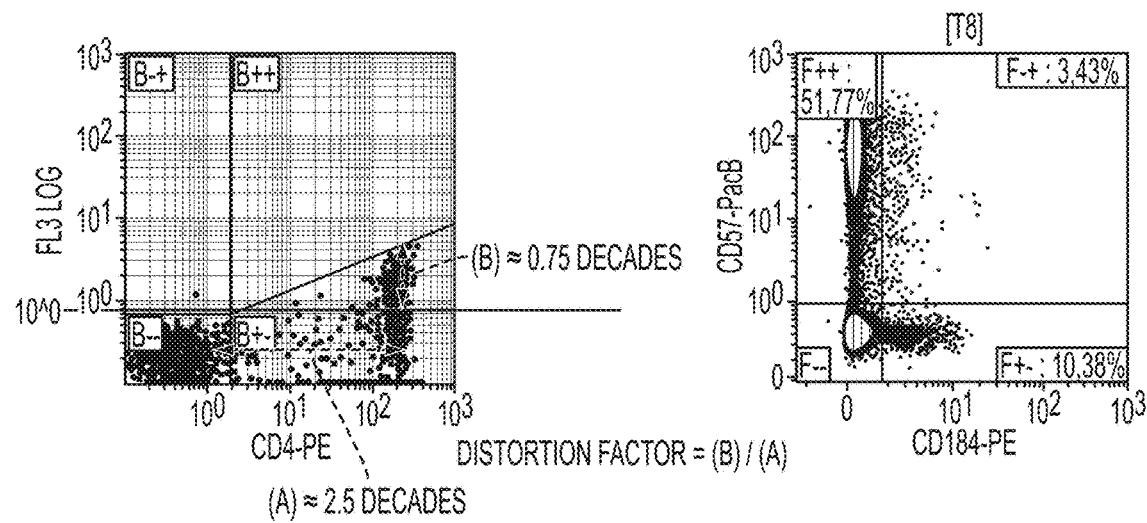
FIG. 1C depicts aspects the expression of antibody-dye conjugates, which may refer to a set of antibody-dye conjugates within a database containing information regarding flow cytometry probes, according to some embodiments.
Figure 1D:
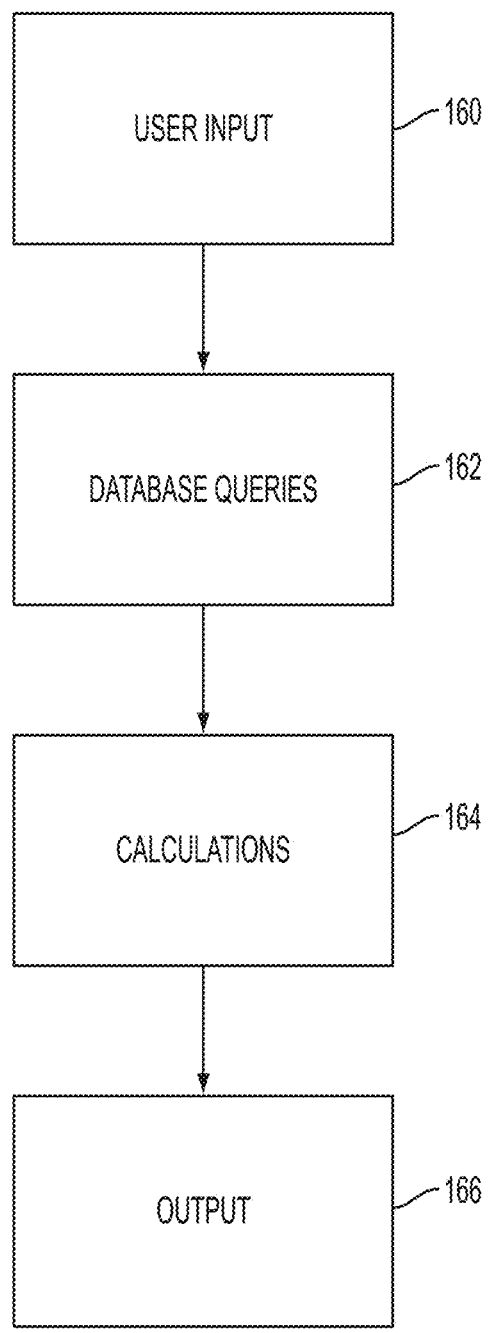
FIG. 1D depicts aspects of database queries for antigen-specific antibodies selected by a user to return information associated with the respective probes, according to some embodiments.

In some instances, a probe panel evaluation or design technique can involve the use of an expected expression pattern of antigens on different target cells, such as exclusion, subpopulation (e.g. parent-descendent as depicted in FIG. 1D), non-exclusive co-expression, or expected antigen expression characteristics such as discrete or modulated. In some cases, a probe panel evaluation or design technique can involve predicting, estimating, or otherwise determining detection limits for individual detection channels, optionally for a variety of different cell types or antigen expression patterns.

As used herein, in the description of antigens, the geneological terms "parent", "child", "sibling", "aunt", and "cousin" are used to identify and describe relationships between clusters of differentiation ("CD") for specific antigens, or the corresponding antibody. It is noted, however, that in the context of the present disclosure, these terms do not refer to generations of cellular reproduction, but rather refer to developmental steps of a given cell as antigens on the given cell surface change due to differentiation or specialization. For example, an antigen such as CD45 may be present on an native T-cell; if the native T-cell specializes to become a killer T-cell, the CD45 antigen may act as a precursor to and become a CD2 (child) antigen, whereas if the native T-cell specializes to become a helper T-cell, the CD45 antigen may act as a precursor to and become a CD4 (child) antigen. In such a situation, the CD45 antigen can be referred to as the parent antigen to both sibling CD2 and CD4 antigens.

Possible developmental relationships between antigens are generally set forth as follows. On some cells, two different antigens may occur on the same cell surface, each of them with its typical mean density and range of expression, resulting in a case called "co-expression". The presence of an antigen on the cell surface may exclude the presence of another specific antigen on the same cell surface, resulting in a case called "exclusion". Antigens with an identical "parent" are called "siblings". On some cells a first antigen can occur on a cell surface where a second antigen is also expressed, however, the second antigen may also occur on a cell surface without the first antigen being present. In such cases, the second antigen is called "parent" antigen while the first antigen is called "descendant" or "child" antigen, resulting in a case called "parent-descendant" or "parent-child". The "sibling" of a "parent" of a given antigen is called the "aunt" of that antigen. When considering a specific antigen, its non-excluded "siblings", its children, their further children (or "grandchildren"), further descending antigens, its "parent", their further "parents" (or "grandparents") and all further ascending antigens and its non-excluded "aunts" can be referred to as the developmental genealogy (or developmental tree) of the specific antigen. It may occur that a single protein is expressed on different cell types belonging to different developmental genealogies, possibly also bearing different mean density, range and distribution characteristics of expression of this antigen. The multiple cellular entities of this multiply expressing antigen can be referred to as "multiple". Further, two co-expressed antigens may have inversely correlated densities of expression, resulting in a case called "inverse correlation".

A set of guidelines for creating developmental genealogies for any given antigen can include the following rules: (1) each antigen must be assigned at least one "parent", if the "parent" is not known "unknown" is assigned as "parent"; (2) if existing, for each antigen "exclusions", "correlations" or "inverse correlations" with "siblings" must be identified, in aspects, the order of consideration of siblings can be based on which antigen has the alphabetically preceding name; (3) if existing, for each antigen "exclusions", "correlations" or "inverse correlations" with "aunts" must be identified, unless the aunts are excluded by the parent of the respective antigen; (4) "multiples" must be handled as is if they were multiple different antigens in order to maintain consistency of individual antigen genealogies, this is done by assigning different "parents", excluded or inversely correlated "siblings" and "aunts", and (5) correlated antigens share the same exclusions and inverse correlations but do not necessarily have the same multiples. By this set of rules, the full set of antigen developmental genealogies for a certain species and body compartment can be created, establishing all possible relations between all antigens.

According to some embodiments, detection limits can be used to rank, compare, or otherwise evaluate fluorochrome-antibody panels, based on antigen expression patterns (which may involve antigen expression densities and fluorochrome brightness), optionally in combination with experimental data. In some aspects, calculations related to determining detection limits can include inputting, or receiving information regarding, a maximum expected signal of a first probe-label combination, based on the characteristics of a first probe and first label. In an instrument or system where signal from a first probe-label combination can create spillover into at least a second detection channel (i.e. a channel not configured to specifically detect the first probe-label conjugate), calculating the increase in detection limits of a second channel can be based on a distortion fact and the maximum expected signal of the first probe-label combination. Accordingly, a probe-label combination can be selected or chosen to include probe panel based on the calculated increase(s) in detection limit(s). In further aspects, the increase in a detection limit in at least a second channel can be caused by an increase in measurement error, as a function of emission intensity, of a first probe-label combination.

Exemplary probe panel systems and methods as disclosed herein are well suited for use in evaluating various conjugate (e.g. fluorochrome-labeled antibody, panel-label combinations, etc.) combinations having complex spillover patterns. Such systems and methods can involve the use of detection channel and expression pattern specific determination of a typical signal intensity and an increase in detection limit related to a typical signal intensity. Accordingly, systems and methods may operate based on particular parameters such as expression densities, fluorochrome intensities, coexpression patterns, and distortion factors. In some instances, the evaluation of a probe panel may include determining a maximum difference for a typical signal intensity and for an increase in detection limit. In some cases, the evaluation of a probe panel may involve determining the ratio of a typical signal intensity to a detection limit, for one or more particular antibody-dye conjugates. Exemplary probe panel evaluation systems and methods can be based on the consideration of coexpression patterns and on the simulation of experimental results. The selection of probe-label combinations can be further based on a comparison of the calculated total increase of detection limit, with an expected minimum increase in at least a second channel. Further, a total increase in detection limits, for all channels, can be calculated for each probe in one or more potential probe panels. In some aspects, systems and methods for evaluating various conjugate combinations can further include calculating a total increase in detection limit for each probe in a second potential probe panel and selecting the probe panel based on a comparison of the calculated total increase in detection limit for each probe in the first potential probe panel, with the calculated total increase in detection limit for each probe in the second potential probe panel. In other aspects, such methods or systems can include calculating a total increase in detection limit for each probe in a second potential probe panel and selecting the probe panel based on the calculated total increase in detection limit for a prioritized probe in the first potential probe panel and the second potential probe panel. In other aspects, a first channel and a second channel can be adjacent channels.

Further, in some embodiments, methods of designing a probe panel for a flow cytometer can include: identifying a first probe and a second probe; identifying an expected minimum signal of the first probe: determining a first detection limit of the first probe based on a potential label associated with the second probe; determining a second detection limit of the first probe based on a different potential label associated with the second probe; and selecting which label to associate with the second probe for the probe panel based on the first detection limit, the second detection limit, and the expected minimum signal of the first probe. In aspects, determining a first detection limit can include multiplying a distortion factor by a maximum expected signal in a detection channel intended to measure the potential label associated with the second probe. In other aspects, determining the first detection limit can include multiplying the distortion factor by a coefficient representing an antigenic coexpression pattern, where in some cases, the coefficient is either one or zero. In further aspects, a maximum expected signal can be based in part on any or all of an expected antigen density on a target cell, the potential label associated with the second probe, and an antigenic coexpression pattern. Some embodiments of such methods or systems include a first probe which is intended to be detected in a first channel, and where determining a first detection limit of the first probe includes multiplying a distortion factor by a maximum expected signal for each channel of the flow cytometer other than the first channel. In such aspects, determining the first detection limit of the first probe is based on a linear superpositioning model of CV enlargements. In some aspects, the distortion factor can be a measure of CV enlargement caused by color compensation.

In some embodiments, a method of designing a probe panel for a flow cytometer can include: identifying a first probe, a second probe, and a third probe; identifying a plurality of possible probe panels, each possible probe panel including a combination of the first probe, the second probe, or the third probe, each probe having a possible label associated thereto; evaluating a first possible probe panel by determining the detection limit of the first probe based on spectrum spillover effects of combination of the second probe and its associated possible label; evaluating a second possible probe panel by determining the detection limit of the second probe based on spectrum spillover effects of the combination of the third probe and its associated possible label; and selecting the probe panel from the plurality of possible probe panels based on the detection limits determined. In such aspects, at least one of the first probe, the second probe, and the third probe can specifically bind to an antigen. In similar aspects, at least one of the first probe, the second probe, and the third probe can specifically bind to an analyte. In further aspects, evaluating a first possible probe panel includes determining the detection limit of a first probe based in part on a coexpression pattern of antigens associated with the first probe and a second probe. In some aspects, the coexpression pattern of antigens can include information regarding coexpression relationships between antigens for a particular cell type. In aspects, spectrum spillover effects of combinations of a second probe and its associated label can be determined to be zero if the coexpression pattern of antigens associated with a first probe and the the second probe indicate the probes are mutually exclusive. In further aspects, spectrum spillover effects of combination of a second probe and its associated label can be determined to be zero if the antigen associated with the second probe is a descendent of the antigen associated with a first probe. In aspects, spectrum spillover effects of combination of the second probe and its associated label can be quantified as a function of a distortion factor and an antigenic coexpression pattern. Conjunctively or alternatively, spectrum spillover effects of combination of the second probe and its associated label can be quantified as a function of an expected antigen density on a target cell. In some aspects, such methods or systems can include displaying a graphical representation of a population distribution of expected signals for a pair of probes in a selected probe panel, where displaying the graphical representation of the population distribution can include displaying the determined detection limit of the first probe and the second probe.

The probe panel techniques as disclosed herein are well suited for use with various automated devices, including the Navios™ and Gallios™ Flow Cytometry systems (Beckman Coulter, Brea, Calif., USA). In some cases, distortion calculations can be based on specific properties or performance characteristics of filter sets and/or photodetectors (e.g. PMTs). Further, probe panel techniques can be based on spectral properties of dyes, optionally which are available within a particular library or repository of dyes or antibody-dye conjugates.

In some instances, the evaluation or simulation of probe panels can be based on certain antigen expression profiles or patterns. Such profiles or patterns may or may not be associated with a particular cell type. In operation, a user may select antibody-dye conjugates according to a particular expression pattern, which may be a selected target expression pattern in a planned experiment. In some cases, an instrument such as a flow cytometer may be configured to accept multiple colors (e.g. ten colors) and the user may wish to chose a lesser number of probes. Hence, the user may expressly assign a first number of probes, while leaving a second number of probes as a dummy variable, so that the sum total of probes is equivalent to the number of color channels in the flow cytometer. In some cases, different dyes (e.g. PC5 and PC5.5) may be detected at the same channel and therefore may not involve simultaneous application.

As disclosed elsewhere herein, once a user selects or inputs certain parameters of a probe panel, the system can operate to retrieve or upload part numbers or other identifying indicia from an antibody database module. If, for example, a desired conjugate (i.e. probe) is not contained in the library, the part number (PN) can be indicated as a customer design service (CDS) probe. In some cases, systems and methods involve the evaluation of a probe panel based on a respective fluorochrome property and a signal intensity (e.g. assumed) that could be expected based on an expression density of the targeted antigen, and such parameters can be retrieved or read from an antibody database module. In some cases, an antibody database module may include data concerning various parameters for use in evaluating probe panels, including probe signal intensity, which may be based on an antigen density for the probe specificity in conjunction with conjugated fluorochrome. Conjugate intensity data can be based on estimates, or may be based on experimental data, for example which may be obtained as part of a manufacturing quality control process.

Further embodiments of the present disclosure encompass systems and methods for assessing positivity in multicolor flow cytometry. Exemplary specificity or gating control techniques can be used to evaluate an individual particle signature, for example to determine whether a blood cell is positive or negative for a certain protein expression, such as a disease marker. In some cases, these control techniques can be used to position a gate or graphical region relative to acquired data, so as to classify the cells from which the data is obtained. Exemplary control techniques can be used in multicolor procedures following compensation. In some cases, the methods disclosed herein provide for a level of standardization which is not present in currently used techniques. Moreover, the control techniques disclosed herein are time-efficient, economical, effective for heterogeneous expression patterns, and provide for the quantification of positives.

In some cases, the emission spectra measured from different fluorescent dyes may overlap, and it may be helpful to compensate the signals obtained by the detectors. For example, a fluorescence compensation technique can be applied during data analysis so as to determine how much interference that Fluorochrome A is having in Channel B (which is assigned to specifically measure Fluorochrome B). As a result, it is possible to obtain the total measured fluorescence at Channel B, and subtract the contribution of Fluorochrome A, so as to determine the fluorescence of Fluorochrome B at Channel B. According to some embodiments, it is possible to obtain the total measured fluorescence at Channel B, and eliminate the contribution of Fluorochrome A, so as to determine the fluorescence of Fluorochrome B at Channel B, for example which may be accomplished using a matrix-based compensation approach involving digital compensation.

Event data can be visually depicted in a variety of ways. For example, a histogram can be used to display a single measurement parameter (e.g. fluorescence) on the horizontal X-axis and the number of events (e.g. cell count) on the vertical Y-axis. In this way, it is possible to determine the number of cells in a sample having certain characteristics. For example, a short peak on the left side of the graph may represent a small group of cells having a dim fluorescence (events within a negative population) and high peak on the right side of the graph may represent a large group of cells having a bright fluorescence (events within a positive population).

As used herein, a "gate" can be used as a boundary to differentiate between a positive population and a negative population. Similarly, a gate can be used as a boundary to define a subpopulation of events. A gate can be set, for example, by delineating a boundary around a subset of events on a data plot such as a dot plot or histogram. A gate can be inclusive so as to select events that fall within a boundary, or exclusive so as to select events that fall outside of the boundary. Accordingly, the number of positive events (on a particular side of the boundary) can refer to the number of cells displaying a physical feature or marker of interest. According to some embodiments of the present invention, gating can be used to distinguish signals corresponding to fluorescent objects from signals corresponding to non-fluorescent objects. According to some embodiments, any event detected with a photomultiplier tube (PMT) may emit a fluorescence signal. Hence, an emitted fluorescence can be associated with a specific label.

Specific gating protocols are available for diagnostic and clinical purposes in the hematology field. For example, gates can be used in flow cytometry data to selectively visualize certain cells of interest such as white blood cells, while eliminating results from unwanted particles such as dead cells and debris. In some situations, it can be difficult to determine where to place a gate so as to effectively classify an event as either positive or negative. By using an appropriate control, it is possible to help identify the difference between a positive population and a negative population. Embodiments of the present invention can be used in conjunction with multicolor cytometry techniques in general, including without limitation the hematological field. In some cases, embodiments of the present invention can be applied to any measurement where a Fluorescence Minus One (FMO) control is helpful or necessary.

Embodiments of the present disclosure provide systems and methods for conducting automated positives analysis in multicolor flow cytometry that is characterized by spillover-induced enlargement of measurement errors. Embodiments further encompass techniques to calculate measurement errors according to each individual event's expression pattern based on a linear superpositioning model of fluorochrome spillover, as also applied for panel design and simulation applications, using the same or similar techniques for determining prediction limits for multicolor flow cytometry, taking into account co-expression pattern of antigens on a detected particle so as to allow for the determination of a spillover ratio for a fluorochrome into all other detection channels by a superposition calculation.

Relatedly, embodiments of the present invention encompass post-acquisition correction techniques for flow cytometry, such that compensation errors associated with acquired sample results can be minimized. For example, use of standard compensation approaches in multi-color channel experiments with fixed correction values can tend to either overcompensate or undercompensate the experiment results at a gating border. Embodiments of the present invention encompass the use of correctly compensated data, or avoid such overcompensation or undercompensation, In some cases, the automatic correction techniques disclosed herein can operate to improve compensated results in a flow cytometry device, so as to enhance the identification of specific positive results after data acquisition. In some embodiments, systems and methods disclosed herein can operate to calculate a corrected detection limit or corrected boundaries between two result sections or corrected limits between specific positivity and specific negativity for each fluorescence signal channel (e.g. photomultiplier), based on a superpositioning model of the spillover from all other dyes detected on all other channels. Using such corrected limits between specific positivity and negativity, it is possible to proceed automatically without the manual gating of result sets, and critical results at the border area between two result sections are observed to be unambiguously assigned to the appropriate section.

Overview

Turning now to the drawings, FIG. 1 depicts aspects of flow cytometry systems and methods according to some embodiments. The configuration 100 of a flow cytometry device typically includes certain fluorescence signal detector assembly parameters 110, as well as laser excitation wavelength parameters 120.

Flow cytometry devices can be configured with any of a variety of laser excitation parameters. For example, laser assemblies can be configured to produce excitation spectra at 355 nm (ultraviolet), 405 nm (violet), 488 nm (blue), 532 nm (green), 561 (yellow), 633 nm (red), 638 nm (red), and the like. Relatedly, laser assemblies can include any number of laser excitation devices. For example, a dual laser assembly may include a first laser for delivering excitation energy at 488 nm and a second laser for delivering energy at 638 nm.

As shown in FIG. 1, the laser excitation energy can impinge upon a dye of an antibody-dye conjugate probe. Typically, a particular dye will be excited at a characteristic wavelength, and subsequently fluoresce a characteristic emission spectra. There may be one or several maxima of fluorescence emission. The emission spectra can cover a range of wavelengths. For example, fluorescein isothiocyanate (FITC) is a fluorochrome that is excited by 488 nm light and that produces a fluorescence emission maximum around 520 nm. At least one wavelength, PC5 and PC5.5 for instance are excited by two wavelengths 488 and 638 nm which adds complexity to the spillover patterns.

Signal detector assemblies 110 can include various combinations of filters and detectors. As shown here, a detector assembly may include a 525/40 bandpass filter for use with a photomultiplier tube device PMT1 that is designated for detecting FITC dye emission. Such configurations can be designed to provide desired detection parameters for a particular fluorochrome. Further configurations as shown can include: a 575/30 bandpass filter for use with a photomultiplier tube device PMT2 that is designated for detecting PE dye emission; a 620/30 bandpass filter for use with a photomultiplier tube device PMT3 that is designated for detecting ECD dye emission; a 675/20 bandpass filter for use with a photomultiplier tube device PMT4 that is designated for detecting PC5 dye emission; a 695/30 bandpass filter for use with a photomultiplier tube device PMT5 that is designated for detecting PE-Cy7 dye emission; and a 660/20 bandpass filter for use with a photomultiplier tube device PMT6 that is designated for detecting APC dye emission. Individual detectors (e.g. PMT1, PMT2, PMT4) can be designated to detect light wavelengths from respective primary dyes (e.g. FITC, PE, PC5) as indicated by emission spectra graph 130. Bandpass filters can be used to allow certain amounts of emitted light to pass therethrough, and on toward a photomultiplier tube (PMT). Specific PMT with their associated bandpass filters may be dedicated to detecting the emission of conjugates excited by specific wavelengths of light.

An exemplary hardware illustration of a flow cytometry device, having a three laser, ten color filter block configuration, is depicted in FIG. 1A. As shown here, a flow cytometry device can include a variety of bandpass (BP) filters, as well as dichroic (DC) short pass (SP) and long pass (LP) filters.

With returning reference to FIG. 1, it can be seen that exemplary techniques may involve a user or operator performing certain actions. For example, user actions 140 may include determining or selecting a configuration of a flow cytometry device, as indicated in step 142, and determining or selecting an antigenic expression pattern of interest, as indicated in step 144. With regard to the step of selecting a device configuration, such a selection can be made using a dropdown (database) button, to choose from a variety of preset hardware configurations (e.g. such as the hardware configuration represented in FIG. 1A).

According to some embodiments, the selection of various hardware configurations and the selection of antigen expression patterns of interest may be implemented in a web-based version. According to some embodiments, systems and methods may involve database means which can provide an indication if there are potentially more antigens out of the probes panel that are included in the expression pattern than the user assigned to a certain pattern. If so, this can result in pointing out to the user that there are more antigens including these probes' influence on the detection limits.

According to some embodiments, hardware configuration may represent any of a variety of laser assembly, filter set, and detection channel combinations. For example, a particular hardware configuration may include one or more lasers emitting at various wavelengths. In some cases, a hardware configuration may include six detection channels and two laser colors (e.g. 488 nm and 638 nm). In some cases, a hardware configuration may include eight detection channels and two laser colors (e.g. 488 nm and 638 nm). In some cases, a hardware configuration may include ten detection channels and three laser colors (e.g. 405 nm, 488 nm, and 638 nm). In some cases, a hardware configuration may include ten detection channels and four laser colors (e.g. 405 nm, 488 nm, 561 nm, and 638 nm).

Exemplary cell monitoring procedures involve evaluating individual cells for the relative quantitative presence or absence of certain cell surface or internal antigens. As shown in FIG. 1, a particular cell at a certain stage of development or in a certain disease state may present a distinctive antigenic expression pattern 150 characterized by the presence of certain antigens (e.g. CD28, CD26, CD3, CD15, CD59, CD71) at the surface of the cell or inside of the cell. Hence, an antibody-dye conjugate panel containing probes specific for such antigens (e.g. conjugate specific for CD28, conjugate specific for CD26) which respectively produce specific emission spectra upon excitation, can be used to analyze a biological sample to determine the extent to which the sample contains cells expressing such antigens, and also the relative quantity of antigen expression on expressing cells. In this way, the probe panel can be used to evaluate or monitor the physiological status of a patient. FIGS. 1B to 1H provide additional details concerning the processing of the user input, the return of database entries and subsequent calculations, and the interpretation of displays.

FIG. 1B depicts aspects of a probe panel selection technique according to embodiments. As shown here, a user can input a set of antibodies corresponding to a particular antigenic expression pattern of interest (e.g. CD57, CD45, and other cell markers). In some cases, the selected antibodies may be assigned to or associated with respective predefined dyes. According to some embodiments, a user may assign each specificity to a predefined dye. According to some embodiments, a user may have the opportunity to enter the specificity only and to let the software propose the optimal antibody-dye-assignments. The selection of probe panels can further include "dummy" channels, where a particular channel and related dye are not intended to be used, the dummy designation and panel design can be used as a "silent" channel and negative control. As used herein, a "silent" channel indicates a detector channel that causes no spillover of signal into any other channel, and can be referred to as a "clean column" when viewed as part of a distortion table. Similarly, as used herein, an "untouched" channel indicates a detector channel that does not receive any spillover of signal from the dyes that channel is not configured to detect, and can be referred to as a "clean row" when viewed as part of a distortion table.

As shown in FIG. 1B, the use of PC5.5 as a dye for detection of the CD33 antigen in detection channel FL4 would be complicated by use of PC5 or the attempted detection of PC5 in detection channel FL4. Accordingly, PC5 is assigned as dummy in this probe panel. FIG. 1B further shows that a user can assign a specific antigen to a desired dye in a particular detection channel, particularly in the example shown, Pacific Blue dye conjugated to CD57, which will be excited by light at 405 nm and detected in PMT detection channel FL9. In this context, the FL9 is the primary channel for detection of excited Pacific Blue dye (and therefore detection of CD57), and accordingly, FL1-8 and FL 10 are secondary channels that could detect unwanted spillover fluorescence signal from the Pacific Blue dye.

As illustrated in FIG. 1C, a probe panel, which may refer to a set of antibody-dye conjugates, can be linked with a database containing information regarding the probes. For example, the database may contain information concerning the fluorescence intensity for each probe in the panel. In some embodiments, the term "panel" may also refer to a sequence or group of several conjugate combinations. As shown, (and discussed in further detail with regard to FIG. 8 below) the database can provide information regarding a set of conjugates (also referred to as the panel), that allows for the calculation of the typical mean fluorescence intensity of a bright positive population, as indicated by population events in decades above 10^0 as shown in the graphs, identified as section (A) in FIG. 1C. The database can also allow for calculation of the minimal fluorescence intensity of a dim positive population. In a discrete antigen expression characteristic evaluation, as seen with the CD4-PE graph, the positive and negative populations are clearly separated, and the minimal fluorescence intensity of the dim positive population is identical to 1. In a modulated antigen expression characteristic evaluation as seen in the CD184-PE versus CD57-PacB graph, however, positive and negative populations are not clearly separated, as the antigen densities can vary between the positive cells, and the minimal fluorescence intensity is assumed to be within the zero decade (i.e., less that 10^0). Further, the database can allow for calculation of the increase of a detection limit for a conjugate (and the corresponding loss of sensitivity) in decades for each conjugate resulting from the combined effects of all occurring spillover contributions, identified as (B) in FIG. 1C. In some aspects, the distortion factor of one conjugate onto another can be characterized as the ratio of (B) over (A).

Relatedly, as shown in FIG. 1D, based on the set of antigen-specific antibodies selected by the user, which can be referred to as the input 160, it is possible to query a database 162 for information associated with the respective probes. As discussed elsewhere herein, the calculations 164 discussed in relation to FIG. 1D can be used for reference for example with respect to the techniques depicted in FIG. 8. Database queries 162 can on the user input 160 of a conjugate can include, for example: (C) the intensity (in decades over 10^0) of a PE-conjugate (or other reference dye) for each conjugate; (D) the fluorochrome brightness relative to PE for each conjugate, where PE (or other reference dye) is equal to 1 or 100%; (E) the typical increase of detection limit caused by secondary channels per decade of signal intensity in a primary channel for each fluorochrome use, i.e. a distortion factor; (F) typical expression characteristics of each antigen, evaluated as either discrete or modulated; (G) the typical antigen coexpression patterns for each single antigen with all other antigens, i.e. the coexpressions of interest, where "1" codes for coexpression and "0" codes for an absence of coexpression or exclusion; and (H) the typical parent-descendent antigen coexpression patters for each single antigen with all other antigens, where "0" codes for a descendent property and "1" codes for an absence of a descendent property.

The output 166 of a database as described in FIG. 1D depends on the area of its application. Particularly, the assumed cell type of interest is different for immunomonitoring and blood cell disorders, therefore typical coexpression patterns and typical expression characteristics related thereto vary depending on the cell type of interest. Calculations 164 based on data retrieved from the database due to search queries can provide the following output. A value for (I), the typical mean fluorescence intensity above 10^0 for each conjugate for bright positive populations (thus directed to discrete plots), can be calculated as:

$$(I)=\log(((10^{\wedge}(C)-10^{\wedge}0*(D))+10^{\wedge}0)$$

where the addition and subtraction of 10^0 provides for consistency in a plot scaling. A value for (J), the typical fluorescence intensity of each conjugate for dim positive populations (thus directed to modulated plots) based on expression characteristics, is similar to the equation for (I) above, but with the value for (C) set to 0 decades above 10^0.

The value for (K), the increase of detection limit (DL) in a secondary detection channel through spillover of a single conjugate in a primary channel, can be determined as:

$$(K)=(I)*DF*(G)*(H)$$

where the value of (K) is calculated for each single conjugate detected in a primary channel, which for example can be nine (9) values for (K) calculated for secondary channels in a ten (10) color panel. Further, a value (L) for the overall increase of DL in a secondary detection channel through combined spillover of all conjugates detected in their respective primary channels can be given by:

$$(L)=\log((10^{\wedge}0(K_1)-10^{\wedge}0)+\log((10^{\wedge}0(K_2)-10^{\wedge})+\log((10^{\wedge}(K_n)-10^{\wedge}0)$$

where, again, the addition and subtraction of 10^0 provides for consistency in a plot scaling. An (L) value can be calculated for each secondary channel. The results of such calculations 164 can subsequently be output 166 to either or both of a display and further processing.

FIG. 1E depicts aspects of a panel evaluation technique, according to embodiments. The graphic display charts shown here can be useful in analyzing or ranking certain panel designs. As shown here, a certain probe or stain is provided, having an antibody specific for the CD45 antigen, conjugated with a PE fluorophore dye. The PE dye can be excited by a 488 nm laser, and can emit spectra which is detected on an FL2 channel (e.g. at approximately 575 nm). The CD45 antigen is typically strongly expressed on leukocyte cells, and PE is a bright fluorophore. Hence, it is possible to observe a strong signal intensity when applying a CD45-PE probe to a lab sample of human origin. As shown here, the result is a full scale intensity. The dashed (minimum separation, square data symbols) and dotted (maximum separation, triangle data points symbols) lines coincide, indicating a discrete expression. That is, the positive and negative populations are clearly separated.

Figure 1F:
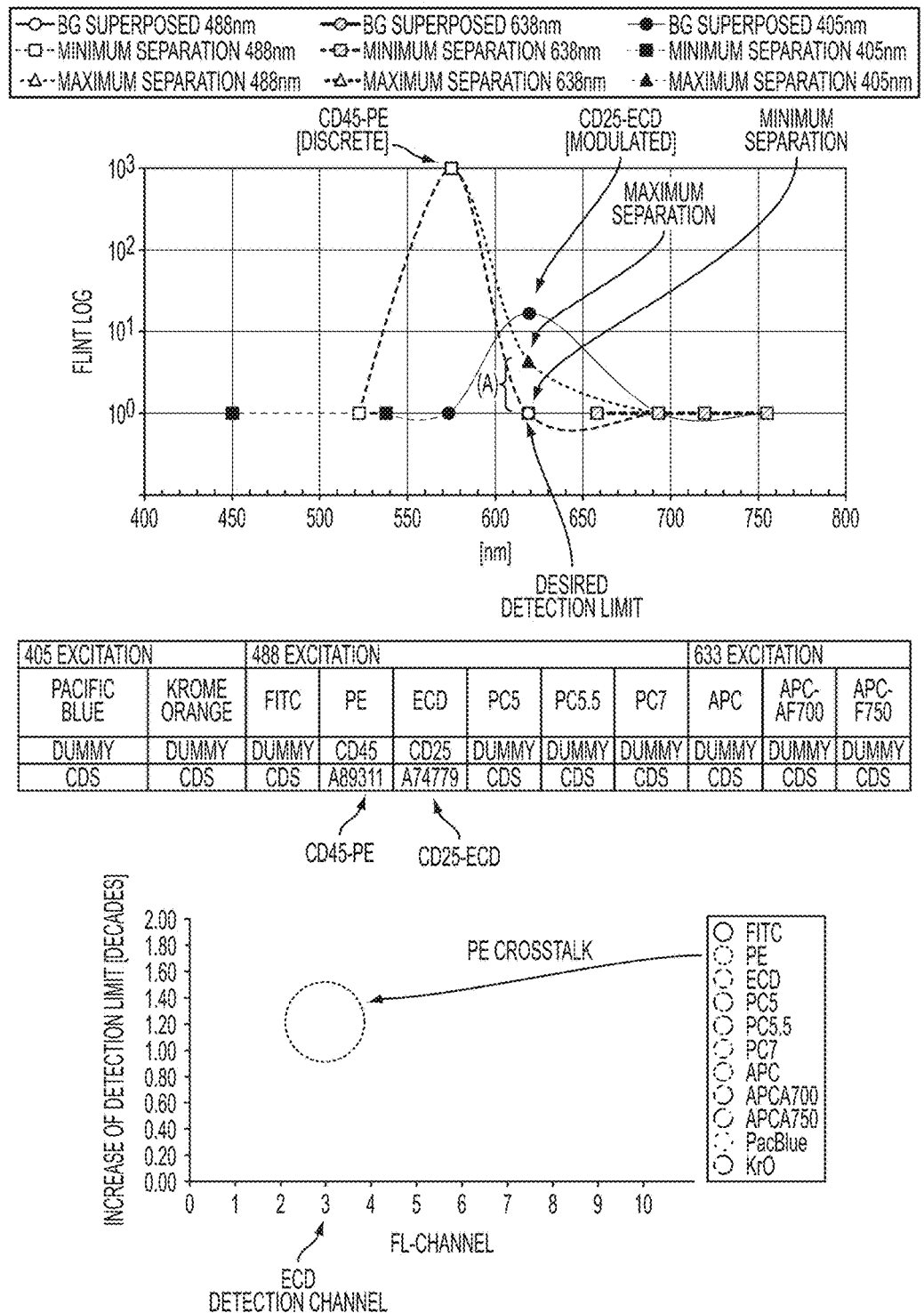

FIG. 1F depicts the addition of a CD25-ECD probe. The ECD dye also can be excited by a 488 nm laser, and can emit spectra which is detected on an FL3 channel (e.g. at approximately 625 nm). As shown here, CD25 is a modulated antigen. That is, there is a difference between the dashed (minimum separation) and dotted (maximum separation). Depending on the activation status of the cell, cells can have a high expression of CD25, down to a negative expression of CD25. Here, the dashed line (minimum separation) coincides with the limit between the first and second decades. This corresponds to a desired detection limit, whereby cells with a very low expression (dim signal) can be detected, as well as cells with a higher expression (bright signal). As depicted here, the cells with a higher expression (maximum separation; dotted line) are about 0.75 Decades higher than cells with a lower expression (minimum separation; dashed line). The difference (A) between the minimum (dashed) and the maximum (dotted) represents the range of expression for CD25 according to this embodiment. Note that this data can also take into account parameters associated with the ECD dye itself. The lower panel bubble plot of FIG. 1F indicates that emission spectra from the PE dye is spilling over into the ECD detection channel and causes an estimated increase of detection limit according to the position of the circle center when projected to the y-axis (in decades) (FL3).

As discussed elsewhere herein, such plots can include different lines corresponding to different laser configurations (e.g. 405 nm, 488 nm, and 638 nm). The threshold between the first and second decades can be used to evaluate certain signal data. In some cases, a particular background may be assumed for a particular coexpression pattern or cell type. For example, a T cell may have a certain pattern as compared to a B cell. Hence, a user may select a phenotype (and corresponding coexpression pattern) that they may wish to see in a simulation output. In some cases, for a given expression pattern, detection limits for a one particular cell type may be different from detection limits for another particular cell type, for example depending on the presence or absence and quantitative characteristics of the given expression pattern.

As shown in FIG. 1F, a detection limit can be represented by a dashed line (square data point symbols). In cases where expression characteristics are discrete, there may be either a negative population, or, positive population, but nothing in between. That is, there will be no cells with varying degrees of antigen densities on that particular population. Hence, the dashed and dotted lines will coincide (as with CD45-PE at about 575 nm). At that point, the highest expression density is equal to the lowest expression density. In contrast, with a modulated expression, an antigen may be found on a particular cell type at a very low expression density, up to a very high expression density. As shown here, a modulated expression can be represented by a dotted line. For example, on a particular CD3+ cell type, CD4 may either be present (CD4+, CD8−), or absent (CD4−, CD8+). This represents a strong positivity, and corresponds to a discrete expression characteristic. As discussed elsewhere herein, the probe panel evaluation can also be based on particular phenotypes (e.g. by assuming a default phenotype such as T cell or monocyte). Hence, users can evaluate probe panel characteristics according to different cell types and expression patterns, and determine how expression patterns may affect detection limits for particular antigens.

Figure 1G:
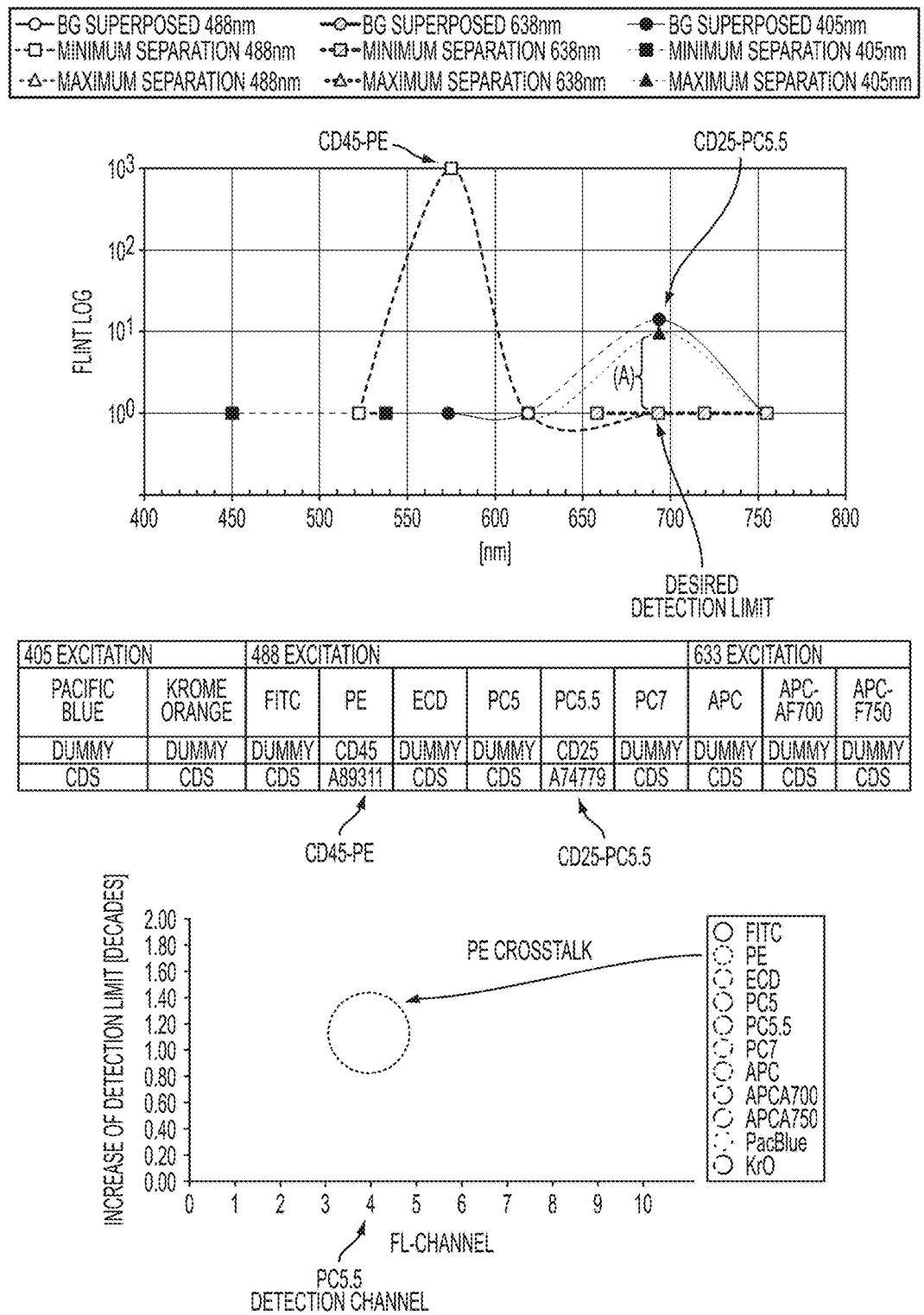

In contrast to FIG. 1F where the CD25 probe has an ECD label, FIG. 1G depicts results from a CD25 probe having a stronger fluorochrome, PC5.5. The desired detection limit of FIG. 1G is the same as that shown in FIG. 1F. However, the range (A) between dotted (maximum) and dashed (minimum) which the embodiment assumes, for the dynamics of the signal intensity, is much higher in FIG. 1G. As shown here, the range is about 1 Decade. The lower panel bubble plot of FIG. 1G indicates that emission spectra from the PE dye is spilling over into the PC5.5 detection channel (FL4).

In FIG. 1H, the CD25-ECD probe is reintroduced. Hence, it is possible to compare the highest expression (signal intensity) that could be expected for a CD25-ECD label with highest expression density that can be expected for CD 25-PC5.5 label. Assuming again, a logarithmic scale, the latter is considerably larger.

It is also useful to consider the background (solid line). For example, as shown in FIG. 1H, a certain level of background BG may occur due to the lymphocyte expression high levels of CD45, which is tagged with the CD45-PE label. As shown here, that background BG signal from PE on the ECD channel is higher than the signal from ECD on the ECD channel. Hence, there is a significant loss of information, and such a panel design may not be favorable.

In FIG. 1I, the CD25-PC5.5 probe is removed and a CD25-PC7 probe is added. There is spillover from PE and PC7 into the FL3 channel. In FIG. 1J, the CD45-PE probe is removed, and there is spillover from PC7 into the FL3 channel. A favorable result is provided when the solid line (background, BG) coincides with or approaches the threshold between the first and second logarithmic decades, as shown in FIG. 1J. As shown here, there is not an overwhelming amount of background that is caused by spillover into the ECD channel. Rather, there is a small amount of spillover from the CD45-PC7 probe emission onto the ECD FL3 detection channel. Hence, there is a gap between the background (BG) and the highest expression density (maximum; dotted line). Accordingly, the detection schema loses only those cells having very low levels of CD25 expression.

FIG. 1K depicts the replacement of the CD25-ECD probe of FIG. 1J with a CD25-PE probe. The PE fluorochrome is stronger than the ECD fluorochrome. As shown in FIG. 1K, there is a similar background BG provided by the CD45-PC7 probe on the PE detection channel FL2. However, the distance between the background and the maximum is greater in FIG. 1K, as compared with FIG. 1J, due to the stronger PE fluorochrome on the CD25 probe.

In FIG. 1L, the CD25-ECD probe is again included in the panel. Here, it can be seen that the distance between the background (solid) and the maximum (dotted) signal is greater for CD25-PE than it is for CD25-ECD. Hence, the overall sensitivity is greater. This result takes into account the intensity of the fluorochrome used on the CD25 probe (e.g. PE intensity>ECD intensity), and also the spillover pattern that stems from other antigens (e.g. CD45) which are also expressed on the cells. Both the fluorochrome intensity and the coexpression spillover pattern can contribute to the sensitivity.

In FIG. 1M, a CD45 antibody is conjugated with an APC-AF750 fluorophore and it can be seen that there is no spillover. Here, the solid line (BG) coincides with the threshold between the first and second decades, and hence there is no background added. Here, there is full sensitivity, so signals can be detected even where there are cells with low expression densities for CD25. As discussed elsewhere herein, as more probes are added to the panel, more complex results will be observed. Such results can take into account various contributions (e.g. fluorophore intensity) where the coexpression pattern is relevant to the spillover.

FIGS. 1N and 1O provide an example for three conjugates, where a given CD can be associated with a given dye. As shown in FIG. 1N, each CD-dye conjugate has a MFI for PE-conjugation above $10^0$ decades (PE being the reference dye); as shown CD-X has an MFI of 0.5, CD-Y has an MFI of 1, and CD-Z has an MFI of 2.5. In some embodiments, the parent descendent matrix can be symmetric. In some embodiments, the parent descendent matrix can be asymmetric. As shown here, the coexpression matrix can be symmetric, although in other aspects, the coexpression matrix can be asymmetric. Further, as shown in FIG. 1O, each dye of the CD-dye conjugates has a relative intensity compared to PE; the A-dye has an intensity of 0.2, the B-dye has an intensity of 0.45, and the C-dye has an intensity of 0.85. These values of the given CD-dye conjugates allow for calculation of a distortion factor table as seen in FIG. 1O, where, in-part, the B-dye has a distortion value of 0.25 effecting the PMT FL1 that is directed to detecting A-dye, and has a distortion value of 0.75 effecting the PMT FL3 that is directed to detecting C-dye. In contrast, the C-dye has no distortion effect on the PMT FL1, and similarly, the A-dye has no distortion effect on the PMT FL3 that is directed to detecting C-dye. In further contrast, the A-dye has a distortion value of 0.65 and the C-dye has a distortion value of 0.1 on the PMT FL2 that is directed to detecting the B-dye. Calculations shown in FIG. 1O are applications of the equations as given by FIG. 1D, using the relevant values provided in FIGS. 1N and 1O.

Where the coexpression pattern has a certain parent/descendent scheme, or an exclusion scheme, then the calculated spillover may not add to the overall distortion. For example, FIG. 1P depicts the calculated result for a single stain (CD25-PE probe). When a second stain (CD45-FITC) is added to the panel, as shown in FIG. 1Q, it can be seen that the FITC dye emission exerts spillover onto the PE FL2 detection channel. The circle on the bubble plot corresponding to the FITC spillover has a certain intercept on the Y-axis, and a certain diameter. As shown here, the CD45-FITC probe can take away about half of a decade of sensitivity on the PE FL2 channel. For example, the distance between the background and the maximum in FIG. 1Q is about half of that distance as depicted in FIG. 1P.

In FIG. 1R, the CD45-FITC probe of FIG. 1Q is replaced with a CD15-FITC probe. The CD15 antigen is less highly expressed, and hence the signal at the FITC detection channel is lower in FIG. 1R as compared to FIG. 1Q. For instance, it can be seen that the maximum (dotted line) is no longer between the third and fourth decades. However, CD45 is coexpressed with CD25, whereas CD15 is not coexpressed with CD25 (e.g. according to default settings in the database). Hence, there is no effective distortion caused by the CD15-FITC probe spillover onto the FL2 PE channel. Relatedly, there is no addition to the background at the PE channel. In other words, the spillover still is present but does not affect CD15 negative cells with regard to analysis of their potential CD25 expression. CD15+ cells, in this example, do not express CD25. Hence, based on the biology of the cells, CD25 expression would not be analyzed on CD15+ cells. These two different antigens could thus be evaluated using different gates.

In another illustration of a coexpression schema, FIG. 1S depicts results where both a CD3-FITC probe and a CD45-ECD probe are generating spillover spectral emission to the PE FL2 detection channel. The overall distortion is a little more than half of a decade. Such a result may be consistent with a coexpression pattern observable on a T cell. It can also be seen that there is a minor amount of spillover into the FL1 FITC detection channel. The bubble plot is useful in resolving the contributions. For example, when considering the Y-intercept values corresponding to the spillover at the FL2 channel, it can be seen that the CD45-ECD spillover is greater than the CD3-FITC spillover. The respective bubble diameters at the FL2 channel indicate that ECD provides a greater contribution to the overall distortion.

Hence, to improve the signal at the FL2 channel (e.g. increase sensitivity), it may be more desirable to remove that ECD spillover at FL2 (e.g. while retaining that FITC spillover). FIG. 1T depicts such a result, where the CD45-ECD probe of FIG. 1S is replaced with a CD45-APC probe. Hence, there is a considerable improvement at the FL2 PE channel for the detection limit. That is, there is a greater distance between the background (solid) and maximum (dotted) lines.

In FIG. 1U, the CD3-FITC and CD45-APC probes of FIG. 1T are replaced with CD3-APC and CD45-ECD probes, respectively. As shown in FIG. 1U, there is still about a half of decade of signal loss at the FL2 PE channel.

The bubble plots provide a useful indication of how a probe configuration (e.g. antigen specificity, fluorophore) can contribute to the detection limit for a detection channel.

Figure 1V:
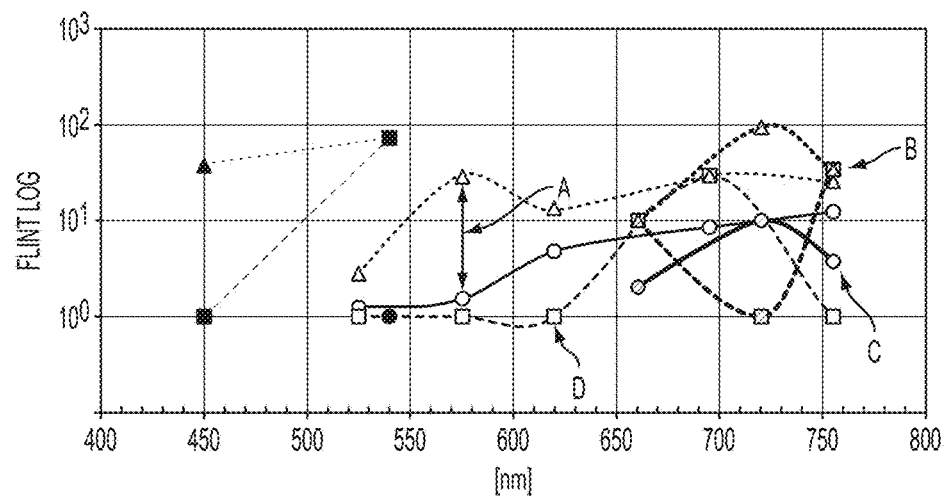

The display of results for an exemplary ten color panel probe is depicted in FIG. 1V. As shown at Section A, for prioritizing conjugates that detect antigens having a modulated expression characteristic, a large distance between an estimated mean fluorescence intensity (triangle) and an overall increase of DL (circle) may be desirable, and can serve as a criterium for the ranking of different conjugate combinations for identical sets of antigens. As shown at Section B, the estimates on bright (triangle) and dim (box) mean fluorescence intensities can be based on typical antigen expression densities and relative fluorochrome intensity (e.g. =(1) & (J) as depicted in FIG. 1D), and for example can coincide due to discrete expression characteristics for CDxy-APCA750-conjugate detected on respective primary channel FL8, assigned to a red laser. As shown at Section C, there may be an overall increase of DL=(L) for FL8, assigned to a red laser. As shown at Section D, due to modulated expression characteristics of CDqw-ECD the typical dim expression density (triangle) can be set to zero decades above $10^0$.

Another display of results for an exemplary ten color panel probe is depicted in FIG. 1W. As shown at Section A, the PE-conjugate (see legend) in this panel causes a 0.6 decade increase in the detection limit (DL) above $10^0$ on the third detection channel FL3 (e.g. when referring to the intercept on the Y-axis), and diameter of the bubble circle corresponds to the contribution of the PE-conjugate to the overall increase of the detection limit on FL3. Hence, it can be seen that the PE conjugate provides the largest contribution to the increase in the detection limit at FL3. As shown at Section B, the PC5/PC5.5 conjugate (see legend) in this panel causes a low-to-moderate increase of 0.2 decades above $10^0$. In many cases, such an increase will be acceptable. Section B also indicates that based on the magnitude of the bubble diameter, the PC5/PC5.5 conjugate can be considered as the major contributor to the overall increase of DL on detection channel 6.

Hence, in a typical procedure the user may select a particular hardware configuration, which may involve certain filters (e.g. bandpass filters) associated with various detectors. In some embodiments, a particular hardware configuration may be assigned or predetermined, without allowing for such a selection. Various hardware configurations may have associated distortion factor values. In some cases, the hardware configurations or distortion data may be retrieved from a database. For example, a database may include data indicating that a distortion factor for a particular bandpass detector configuration (e.g. infrared) is larger than some other detector configuration. Accordingly, the sensitivity and/or measurement error can vary based on the hardware configuration. In some embodiments, a database may include a preset number of hardware configurations, and the user may select from among them. For example, a particular hardware configuration may include data related to the Navios™ Flow Cytometry system or the Gallios™ Flow Cytometry system (both available from Beckman Coulter, Brea, Calif., USA). In some cases, a particular hardware configuration will have an associated distortion factor profile. The number of lasers and/or the number of detection channels contained in the hardware configuration can have an influence on the number of fluorochromes used in a particular probe panel. In some cases, the characteristics of the bandpass filters influence the distortion factors. Relatedly, the quality of a PMT or other detectors such as an avalanche photodiode may influence the distortion factors.

Antibody Selection for Panel Design and Simulation

Figure 2:
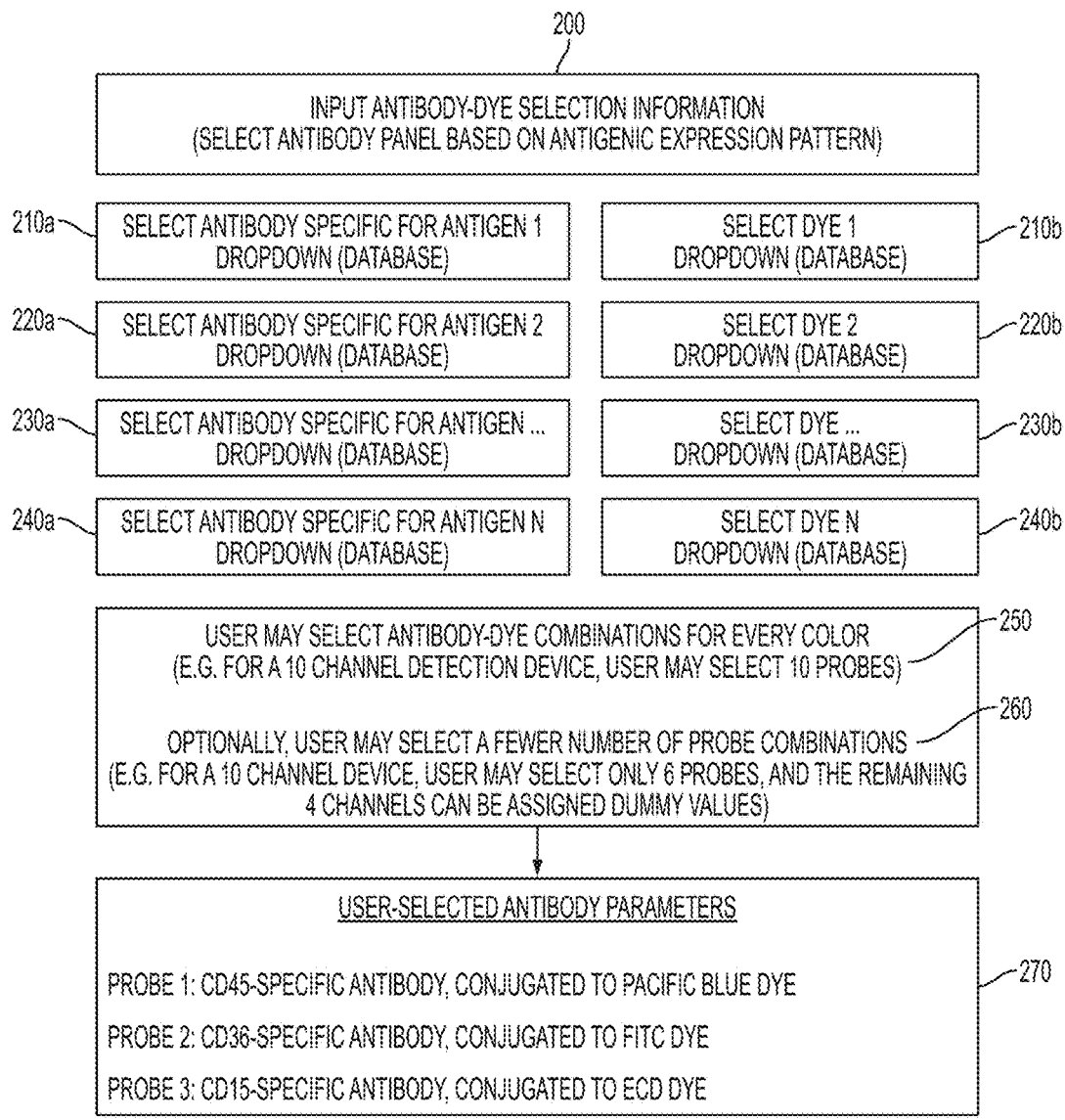
FIG. 2 depicts aspects of an operator selection procedure, according to some embodiments.

FIG. 2 depicts aspects of an operator selection procedure 200, whereby the operator inputs certain antibody and dye selection information for use in selecting an antibody panel. For example, as shown in step 210a, the operator can select an antibody specific for antigen 1 (e.g. CD28), optionally along with a corresponding dye (e.g. FITC) as indicated in step 210b. Further, the operator can select additional antibodies specific for respective antigens of an expression profile (e.g. steps 220a, 230a, and 240a), optionally along with respective corresponding dyes (e.g. steps 220b, 220c, 220d). As shown here, the antigen-specific antibody parameters can be selected from a dropdown menu of a database, and the dyes can also be selected from a dropdown menus of a database. In some instances, the dye selection process can be configured so that no dye is expressly selected by the operator. Rather, a dye associated with the selected antibody can be provided by the database. According to some embodiments, if the user does not assign dyes to antibodies, then the system can identify the most appropriate dyes for all non-assigned antibodies based on consideration of the whole probes panel (sensitivity etc.) out of the database that will provide all conjugations available for the respective antibody. The fluorochromes chosen by the system may not be displayed until the system has conducted the necessary calculation and iterations, i.e. when the simulated data output occurs.

Systems and methods as disclosed herein can embody the drop down database and user interface features shown here. Hence, the user may designate the antigens of interest, and the antigen designation in turn will influence the antibody selected. According to some embodiments, the user will directly choose antibodies in the interface. In some cases, the antigens of interest may correspond to a particular cell type, such as a T cell. Hence, a user may select a collection of antibodies which correspond to a T cell panel.

The menu shown in FIG. 2 includes two columns which can be presented to the user. The left column corresponds to antibody specificity, and the right column correspond to dye selection or assignment. At this stage in the process, the user may or may not have a particular expression pattern in mind. For example, the user may have only a list of antigens which may be of interest. In some cases, a user may know when selecting certain antigens whether it is desirable to be more sensitive when selecting a dye or alternatively, less sensitive. Relatedly, a database will often include data related to the expression density of a particular antigen, and this data can be taken into account when the dye is selected or assigned by the system. In some cases, the expression density may depend on a particular cell type. For example, the database may include information that a particular marker is minimally expressed on one cell type, whereas the same marker is highly expressed on another cell type. If a user does not select a dye to go along with a selected antibody, the system may take into account other features, such as the cell type, when recommending or assigning a dye to that antibody. According to some embodiments, at this stage in the process the system will not yet assign a dye in case the user did not select one.

Typically, different dyes will have different brightnesses quantified by the quantum yield and absorption coefficient of the dye, indicating how much of passing light is absorbed and how much of the light absorbed by the dye will translate to fluorescence emission, respectively. In many cases the absorption coefficient and the quantum yield correspond to each other. For example, a PE dye is considered to have a high absorption and quantum yield, and a high percentage of the light absorbed is translated to fluorescence emission. In contrast, FITC has a lower absorption coefficient and quantum yield, and a lower percentage of the light absorbed is translated to fluorescence emission. As a result, the selection of a particular dye can determine the sensitivity that can be achieved. Hence, using PE may confer the ability to achieve a higher sensitivity, as compared to the use of FITC (e.g. even taking into account that a single antibody molecule can be covalently bound to several FITC molecules due to the small size of the FITC molecule (<1 kD) which cannot be realized for the large (>200 kD) PE molecule).

In some cases, the user may elect to accept one or more of the default dye selections provided by the system database. Optionally, the user may elect to modify the default selections. According to some embodiments, at this stage in the process the system may not recommend dyes to be used with antibodies as the full range of information provided by all user interfaces input may be needed to select appropriate dyes for the antibodies. Relatedly, a system database may include a certain assumed expression density for a typical/particular T cell antigen (e.g. CD3 antigen). When selecting a particular antigen specificity, the system may retrieve a particular expression density that is typical for an antigen on a certain cell type. For example, when selecting an antibody specific for a CD3 antigen, the database may include relationship information associating the CD3 antigen with a T cell. As another example, a user may select antibody specificity for CD16, CD38, and the like. Some antigens have various expression densities, present on various types of cells. Hence, expression densities can vary amongst T cells, B cells, and monocytes, for example. For example, when selecting an antigen specificity, the database may have three typical expression densities, for three different cell types. In some embodiments, the user can opt to modify an assumed or default density, if desired.

Figure 2C:
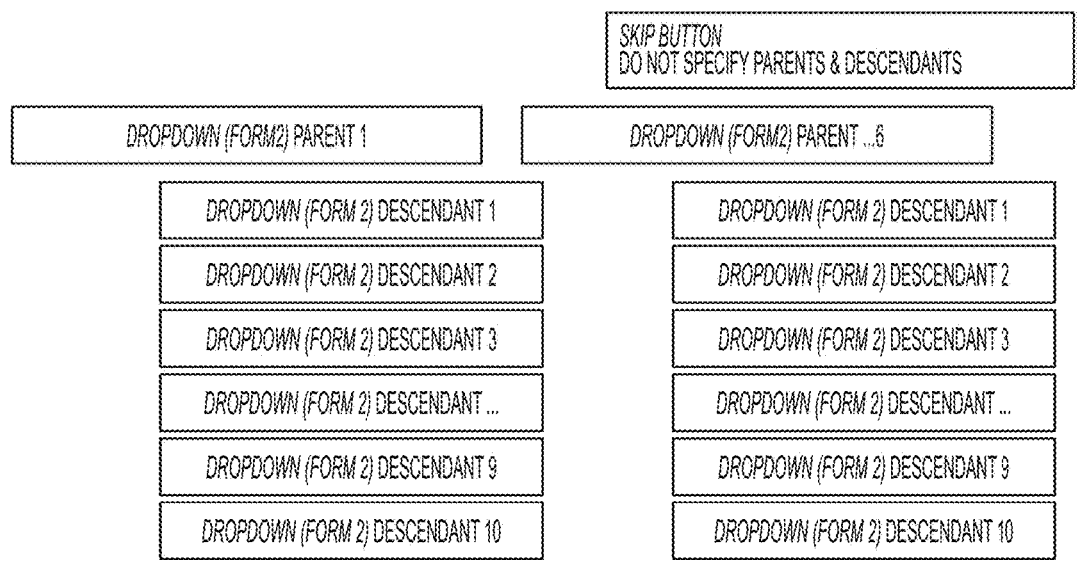
Figure 2D:
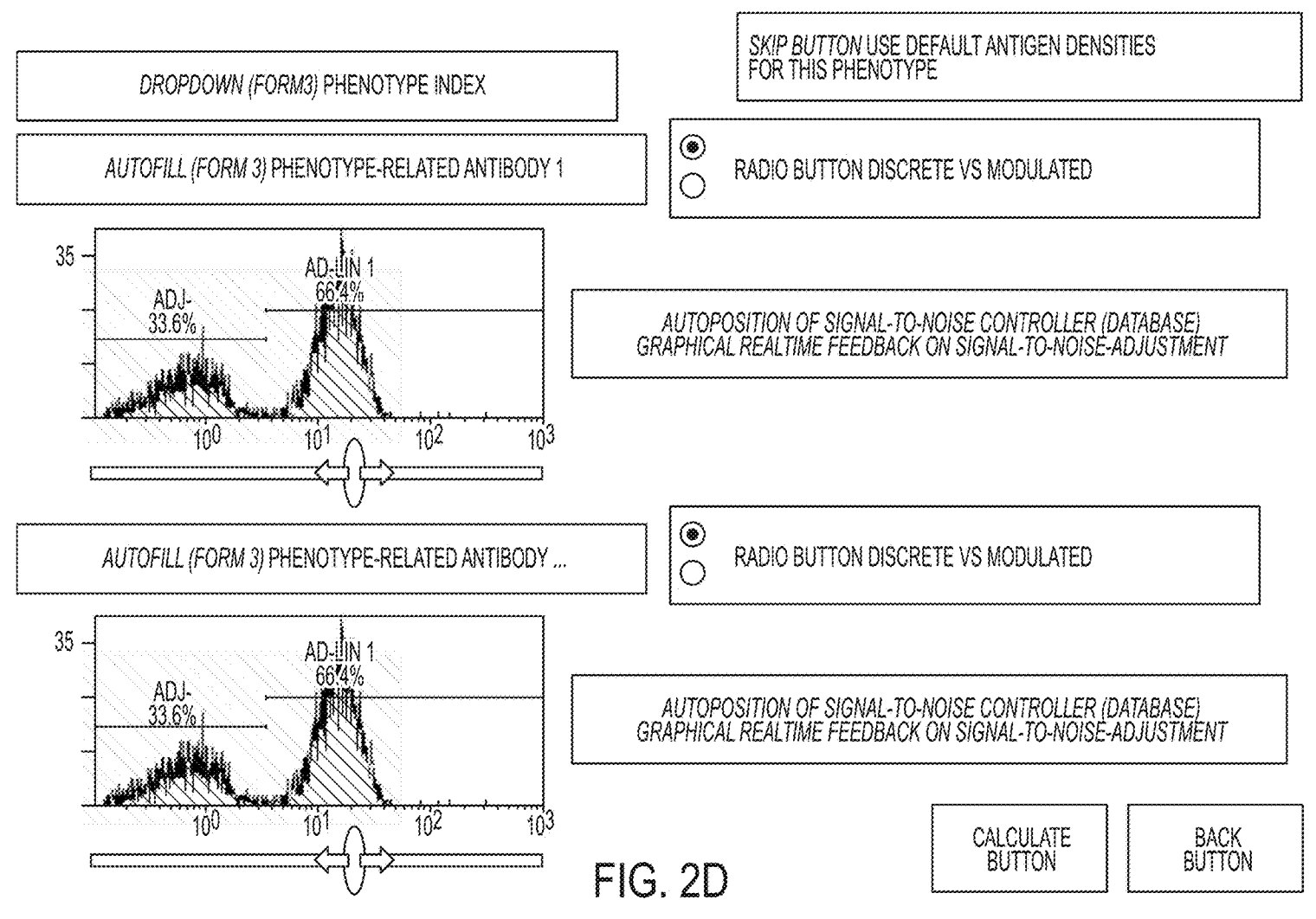

FIGS. 2A, 2B, and 2C illustrate similar operation selection features for target phenotype, phenotype exclusion, and parent/descendent schemes, respectively. FIG. 2D depicts operation selection features for antigen density parameters.

As shown in FIG. 2A, the user has the option to define various phenotypes, if desired, based on the selection of antibodies which may be contained in a database. In some embodiments, information on typical antigen coexpression patterns that matches the defined phenotypes can be included in a database as preselected or predefined typical antigen coexpression patterns. The database can include default information on the antigens' coexpression patterns that usually occur. This is less specific than predefined cellular phenotypes and allows for combinations of antigens that do not occur in the same gate. As one example, the T cell is a prominent type of cell phenotype that is used in cytometry. Optionally, a user may define their own phenotype. In some cases, a user may assign a certain expression pattern to a phenotype. As shown here, the user also has the option of skipping this step, and not specifying a phenotype. When selecting a particular phenotype, the database can provide an associated set of antigen specific antibodies. According to some embodiments, the user can define the phenotype by directly choosing antibodies. For example, if a dye has been assigned to an antibody in FIG. 2 then the formula can display this pre-selection in the right column in response to choosing the respective antibody in the left column of FIG. 2A. The column on the right side may allow the user to preselect dyes, in an autofill manner. According to some embodiments, at this stage in the process the user may not be able to assign dyes to antibodies any more (e.g. as has been done in FIG. 2). However, if the user has assigned dyes to antibodies in FIG. 2 then these dyes will be displayed in the right column upon choosing the respective antibodies in the left column. In some cases, it is possible to select between different phenotypes, or to prioritize phenotypes. For example, phenotypes can be prioritized based on a target population, or based on a particular antigen that should be detected on a particular phenotype. In some cases, the system may prioritize an antigen based on expression density. For example, an antigen with a low expression density can be given a high priority.

As shown in FIG. 2B, the user has the option to select various phenotype exclusions, if desired, which may be contained in a database. For example, a database can contain information indicating that a certain antigen never occurs on the same cell surface with another certain antigen. Optionally, the user may define certain exclusions. As depicted here in the left column, the user may define a first exclusion, which corresponds to an antibody that was selected earlier as discussed in relation to FIG. 2 and is displayed in the header section of the left column. The user may select multiple exclusions in this manner, for multiple antibodies of the panel. For instance, the user may indicate that an antigen CD-X is to be exclusive of antigens CD-Y and CD-Z. Such selections can have an impact on a graphic display for a probe panel, as discussed elsewhere herein. According to some embodiments, the exclusion of a particular antigen may not influence a respective detection limit, because only labels that are on the same cell surface can influence each other's channel detection limits. That is, once the antigens are not on the same cell surface, the label dyes will also not be on the same cell surface, and hence there can be no interference between their respective emission spectra. As shown in FIG. 2B, the user also has the option of not specifying exclusions.

In some instances, a user may select two antigens that are never expressed together. Optionally, the database may make certain assumptions regarding exclusions. For example, the system may assume that a particular T cell marker and a particular B cell marker are exclusive from one another. In some cases, a system may allow a user to indicate that there are no exclusions. Accordingly, the user may be presented with various options, including (a) accepting exclusions provided by the database, (b) actively assigning exclusions, and/or (c) assigning no exclusions, such that any antigen can occur with another antigen, on any cell.

As shown in FIG. 2C, the user has the option to select various parent-descendent relationships, if desired, which may be contained in a database. For example, a database can contain information indicating that a certain antigen has a parent or descendent relationship with another antigen. Optionally, the user may opt not to specify such a relationship. As depicted here in the left column, the user may define a first parent and any related descendents, which may correspond to antibodies that were selected earlier as discussed in relation to FIG. 2. As an example of one parent-descendent scheme, a parent-descendent relation can mean that a parent marker expressed on parent cell, and that cell A expresses the parent protein in addition to subpopulation/descendent A protein, and that cell B expresses the parent protein in addition to a subpopulation/descendant B protein. For instance, a parent T cell may include a CD3 antigen, and some T cell dependents may express CD3 antigen along with a child cell antigen CD4, and some T cell dependents may express CD3 antigen along with a child cell antigen CD8. The expression of CD4 and CD8 in the child cells can be mutually exclusive. For example, the child cells may be either CD4+/CD8− or CD4−/CD8+. In some cases, every CD4+ child cell is CD3+, every CD8+ child cell is CD3+. In this way, parent-descendent relationships can be considered to have an effect on expression patterns. Relatedly, parent-descendent relationships can be considered to have an impact on the relevance of associated distortion. As an example, if a descendent antigen is labeled with a dye that would cause a distortion in the channel where the parent labeled antigen is detected, then it may not be necessary to account for this distortion. For example, where all CD4+ cells are also positive for CD3, there may be no CD4+ that will be in the background (e.g. there is no CD4+ that is also CD3−). In some cases, a parent CD3 label may cause distortion in a child CD4 channel.

Hence, the parent-descendent relationships can have an effect on background distortion. Where distortion is applied to a positive population, it could be described as a population that is on a higher range of the logarithmic scale. In some related instances, such a measurement error may not be substantially relevant with regard to the detection limit of the channel in which the positive population is detected. According to some embodiments, there is no effect caused by a parent-descendant relationship other than making a spillover and related distortion irrelevant if the spillover occurs from descendant channel to parent channel. If the spillover occurs from parent into the descendant channel the "normal" distortion applies.

As discussed elsewhere herein, the primary detection channel for a particular fluorochrome is the channel where the user intends to detect the signal associated with that fluorochrome. Relative to a single primary channel, there may be one or more secondary channels (e.g. where a fluorochrome for the primary channel has emission spectra that spills over into the other channels). For example, a system may be configured to primarily detect PE dye at an FL2 channel, yet the PE emission spectra may spillover to other channels, such as FL3, FL4, FL5, and the like. In this sense, the secondary channels can indicate where unwanted signal intensities are detected. Such spillover characteristics can be used along with parent-descendent relationships to evaluate or configure probe panel designs. In some cases, a probe may be assigned to a primary channel, while having strong spillover to a secondary channel, where the secondary channel represents a parent channel. As also described elsewhere herein, parent/descendent schemes for typical populations can be represented in a database. In some cases, the user may opt to proceed with a default parent-descendent scheme. In some cases, a user may opt to define their own parent-descendent scheme. In some cases, a user may opt to specify that there are no parent descendent-schemes. For example, with regard to analysis of blood cell disorders, certain expression patterns may be unusually aberrant. In such instances, it may be desirable for the user to indicate that there are no parent-descendent relationships.

As shown in FIG. 2D, the user has the option to select certain antigen density parameters, if desired, which may be contained in a database. For example, default antigen densities may be contained in the database. Such defaults may refer to typical populations that are present in human peripheral blood. Other types of defaults may be implemented. Hence, depending on whether a user is interested in evaluating material associated with cell culture cells, or material associated with bone marrow, for example, different defaults and/or expression densities may be available.

As also depicted in FIG. 2D, for individual antibodies, it is possible to select a phenotype as indexed according to FIG. 2A. Each antibody selected for a particular phenotype can be represented in a histogram. Further, a user may have the option to accept or modify what is considered a typical expression density. With reference to the bar below the histogram, a button can be moved to shift the positive population vs. the negative population. Thus, it is possible to influence the signal to noise ratio that may be assumed for a particular population. Changes in signal-to-noise ration can influence the crosstalk or spillover that may be expected to be present in other channels. According to some embodiments, the terms crosstalk and spillover may be used interchangeably. Hence, where are brighter signal is assumed, or where a brighter signal is selected or adjusted, a greater amount of crosstalk or spillover may be assumed to be present in other channels. In some instances, a user may opt to proceed with a default (e.g. antigen density and/or signal intensity). In some instances, a user may modify signal intensities according to the expected characteristics of a particular desired phenotype, such as a T cell population or a monocyte population or a non-human cell population or a population not related to human peripheral blood or bone marrow or others.

Figure 3:
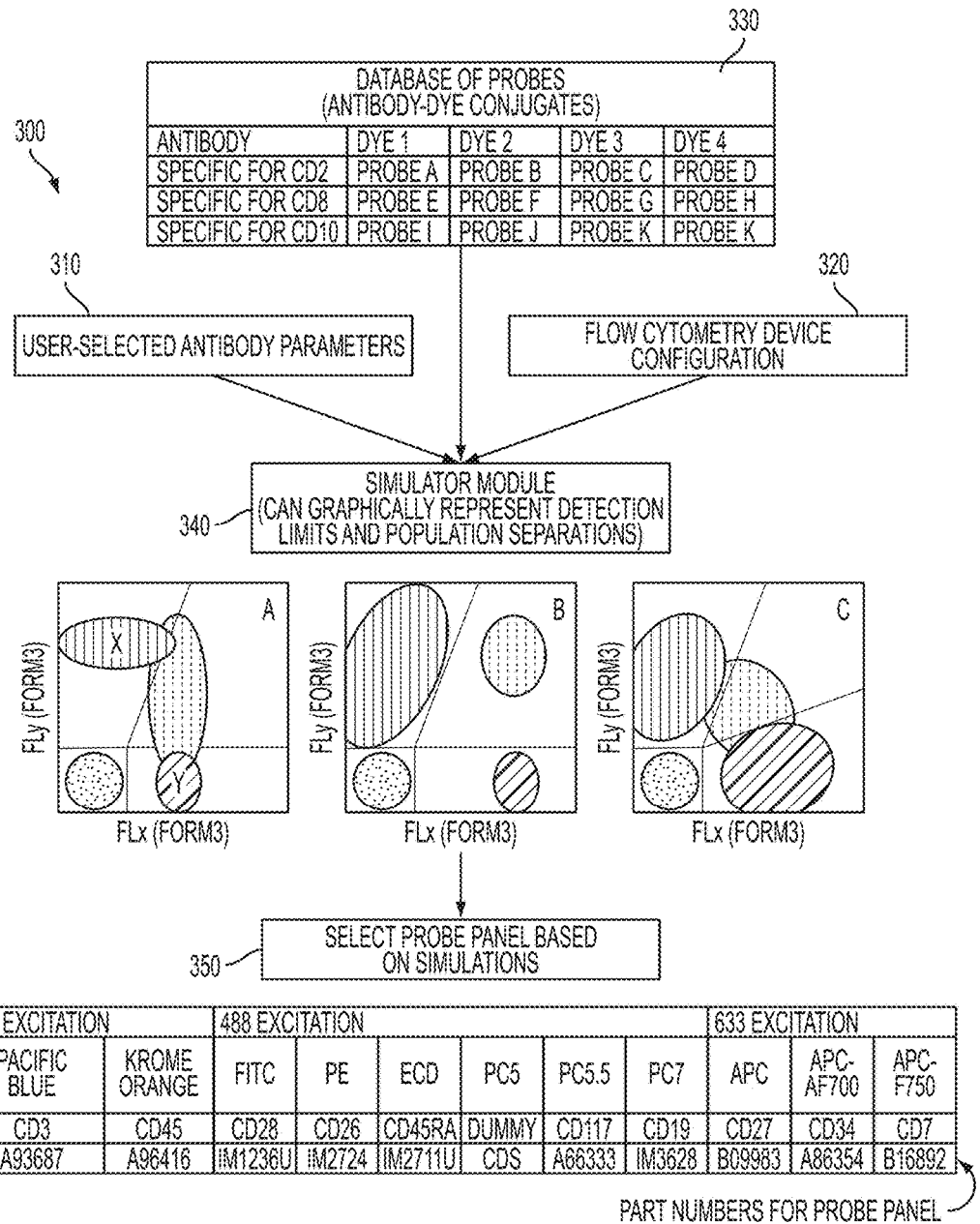
FIG. 3 depicts aspects of a probe panel selection technique, according to some embodiments.

FIG. 3 depicts aspects of a probe panel selection technique 300 according to embodiments. As shown here, data such as user-selected antibody parameters 310 (e.g. as described in FIG. 2), a flow cytometry device configuration 320 (e.g. as described in FIG. 1), and an antibody database 330, can be input into or accessed by a simulator module 340, which operates to proposed optimal combinations according to prioritized phenotypes and/or antigen expressions, and to produce graphs (e.g. A. B, and C) showing detection limits and population separations based on simulated probe panels. As illustrated by step 350, it possible to select a probe panel based on the simulations. In the embodiment depicted here, the selected probe panel is for flow cytometry device configuration having three lasers and ten color detection channels (PC5 and PC5.5 can be detected by the same channel). The panel includes antibody-dye conjugates specific for ten CD antigens.

Table 1 below depicts aspects of an exemplary probe roster which may be associated with or part of the database probes. As depicted here, individual probes can include an antibody or other binding agent specific to a particular antigen, conjugated with a dye.

TABLE 1

Probe Roster

| Probe Number | Dye | Antibody |
| --- | --- | --- |
| Probe 1 | Dye (a) | Binds to Antigen (i) |
| Probe 2 | Dye (a) | Binds to Antigen (ii) |
| Probe 3 | Dye (b) | Binds to Antigen (i) |
| Probe 4 | Dye (b) | Binds to Antigen (ii) |

It is understood that a cellular or surface structure such as a cluster of differentiation (CD) and the antibody directed against the structure or cluster can be referred to interchangeably. For example, an antibody that recognizes cluster of differentiation 3 (CD3) can also be referred to as CD3 or CD3 antibody. In some cases, the term anti-CD3 antibody may be used. In some cases, there are cellular structures that have not been assigned a CD number. In such cases, the name of the structure itself can also be used to name the antibody. In some cases, the nomenclature of an anti-"structure" antibody may be used.

As discussed elsewhere herein, according to an expression pattern that is retrieved from a database (or assumed or assigned by a user), a particular expression pattern may correspond to a coexpression scheme, a specific exclusion scheme, or a parent-descendent scheme. In some cases, selected antigens may be assigned to a certain phenotype. Based on these categories of information, it is possible to graphically display data in bivariate dot plot representations such as those shown in Panels A, B, and C. In some cases, the representations may also incorporate estimates of background distortion.

As shown here, the population X may reflect instances where the intent is to detect antigen X on a particular population. In panel A, there is a sharp hinge of the straight line delimiting the upper left quadrant from the upper right quadrant, indicating a strong increase in a detection limit for antigen Y for the population expressing antigen Y depending on the antigen Y density. These detection limit characteristics are very different from that for antigen X for the population expressing antigen Y. The line delimiting the lower right quadrant from the upper right quadrant has no hinge but is parallel with the outline of the diagram thus indicating that there is no dependency of the detection limit for antigen Y from the expression density of antigen X on respective cells. Hence, this graphical output may indicate to the user that this particular choice may not be optimal.

Hence, where are user selects or inputs for a particular antigen expression pattern (e.g. as associated with antibody parameters 310), the system may retrieve certain antibody-dye conjugates from a database based on the user selection or input. The user can then observe the various graphical outputs associated with the antigen expression pattern. According to some embodiments, the system can generate an optimized probes panel proposal according to antigen selections made by the user. According to some embodiments, a user may select a particular antibody specificity profile or antigen expression pattern, and the system may return a permutation of all conjugate combinations possible for the profile or pattern. In some cases, the system may display selected conjugate combinations according to prioritized antigens. Hence, there may be a priority ranking for certain antigens, and the ranking can be used for determining which conjugate combinations are expected to deliver optimal results with regard to sensitivity and which conjugate combinations to display in a graphic output. According to some embodiments, the system can return optimized conjugate combinations according to prioritized conjugates/phenotype related to fluorochrome brightness expression patterns and the like. In some cases, antigens can be prioritized on the basis of sensitivity. For example, it may be desirable to have a higher sensitivity for one antigen, while a lower specificity for a second antigen is considered as sufficient.

As discussed elsewhere herein, the graphic output can be influenced by various factors. For example, the display may depend on the expression pattern, the flow cytometry device configuration, and/or the probes characteristics (e.g. whether dyes considered as optimal for a given specificity within a given antibody combination, or specifically selected dyes).

According to some embodiments, some or all entries retrieved from the database may be default. Relatedly, some or all proposals for probes panels as recommended by the system can be calculated based on a whole set of antigens inclusive of expression patterns. For example, ten default sets for ten antigens may result in a different probes panel recommendation when, for example, different expected expression patterns are chosen by the user. The modification of certain parameters, such as an expression pattern or a signal intensity, can result in a change in the display. In some cases, a simulation display may indicate a particular recommendation of the system. In some cases, a simulation display may show output according to pre-set dyes. In some cases, a simulation display may show output according to a mixed case, where some dyes are selected by the user and some dyes are selected by the system. According to some embodiments, systems can return optimized conjugate combinations according to prioritized conjugates/phenotype related to fluorochrome brightness expression patterns and the like. Antigens relevant for a certain phenotype can be shown on bivariate dot plots or other representations. In FIG. 3, there are three plots shown. Embodiments of the present invention encompass the display of any number of plots. For example, where five antigens are selected, there may be ten plots, as depicted in Table 2.

TABLE 2

|   | 1 | 2 | 3 | 4 | 5 |
|---|---|---|---|---|---|
| 1 | — | plot 1 | plot 2 | plot 3 | plot 4 |
| 2 | — | — | plot 5 | plot 6 | plot 7 |
| 3 | — | — | — | plot 8 | plot 9 |
| 4 | — | — | — | — | plot 10 |
| 5 | — | — | — | — | — |

According to some embodiments, the user can review the display output plot, and take into account any antigens which have been prioritized, any knowledge of target populations, and/or any knowledge of target coexpression antigens, and then evaluate the detection limits and determine whether a large distortion is expected or not. In some cases, a system may recommend a particular probe panel, and the user may select the recommended panel without taking into account what is shown in a graphical display.

For example, in the instance where CD3 is coexpressed with a particular antigen, and there is a significant distortion on the population because there are many antigens overspilling into the detection channel, the user may decide not to proceed with such a probe panel. The user then may return to any step as seen in FIGS. 2-2D and modify their inputs and/or the default inputs as retrieved from the database.

Detection Limits

One objective in flow cytometry, for example where cells are stained with immunofluorescent dyes, is to analyze proteins or markers which are expressed on the surface of or inside the cell. In this way, it is possible to categorize cells (or subsets of cells) as being either positive or negative for a particular antigen or marker. Hence, for example, some cells may be considered "negative" for a particular marker or antigen, and other cells may be considered "positive" for a particular marker or antigen. In order to determine whether a cell is negative or positive, it may be helpful to define a threshold of signal intensity, whereby cells which express minimal or nonexistent antigen levels so as to produce a signal intensity below the threshold are considered "negative" and cells which express sufficient antigen levels so as to produce a signal intensity above the threshold are considered "positive". Such a threshold of signal intensity may also be referred to as a detection limit.

Hence, in some instances, a detection limit may refer to a threshold between a negative event and a positive event on a particular scale. That is, there may be a positive/negative cut-off, whereby an undetectable or low level of signal or fluorescence corresponds to a negative event. In some cases, unspecific fluorescence may correspond to a negative event. In contrast, a sufficiently high level of signal or fluorescence can be considered as a positive event.

As discussed elsewhere herein, a particular detection limit can be based on a formulation involving isotype data, fluorescence intensities, distortion factors, and the like.

Isotype Control Staining

A typical immunophenotyping protocol involves labeling cells of a biological sample with antibody-dye conjugates which specifically bind to proteins on the surface of the cells. In this way, proteins expressed by the cells can be analyzed. Due to the nature of the conjugate probes however, unwanted non-specific binding may occur between probes and cells. That is, a particular probe may bind to a certain cell, even though that probe is not designed to bind to the cell.

Isotype control antibodies can be used to provide a negative control for such non-specific binding or fluorescence. Typically, the isotype control is generated from the same host from which the probe antibody is generated. For example, if an antibody of a conjugate probe is generated from a mouse, then the isotype antibody used to control for that probe is also generated from a mouse. Moreover, the isotype can be generated so that is has a specificity for an antigen which is known not to occur in the sample (or that otherwise does not occur on a target cell).

When staining a sample with an isotype control, the resulting signal can be an indication of non-specific binding of an antibody-dye conjugate to a cell surface. In this way, an isotype control can be used to evaluate the level of background intensity which may occur in a conjugate staining procedure. For example, the isotype control can signify the level about which fluorescence intensity obtained with a probe can be considered to be specific. That is, if when staining with the designed probe, a detected signal exceeds the background intensity level provided by the isotype control, then it is possible to infer that the detected signal corresponds to a positive event.

In practice, an isotype control can be used to distinguish specific binding from nonspecific binding, to set specificity or gating controls, to designate the location of gates or graphical regions or boundaries used to classify cells, to determine positivity or negativity for particular antigens, to assign positive/negative boundaries in the data, and the like. Isotype antibody controls can be used in flow cytometry procedures. It may be particularly helpful to use isotype antibody controls when employing multiple stains in a flow cytometry procedure.

In some instances, for example where an antigen has a distinct bimodal expression, with no overlap between positive and negative population (e.g. CD4 and CD8 on T cells), it may be possible to proceed without use of a control.

Isotype controls can help to address signal to noise issues in a cell analysis protocol. When determining whether an expression pattern or cell of interest may be positive for a given marker, an isotype control can help to optimize the resolution sensitivity without unduly sacrificing specificity. When using an isotype control, it is possible to evaluate whether a detected signal may correspond to only nonspecific binding, or to some combination of nonspecific and specific binding. As discussed elsewhere herein, isotype controls can be useful for determining a detection limit. Isotypes may contribute to background, and spectral overlap or spillover can contribute to background spread, both of which can play a role in sensitivity.

Figure 4:
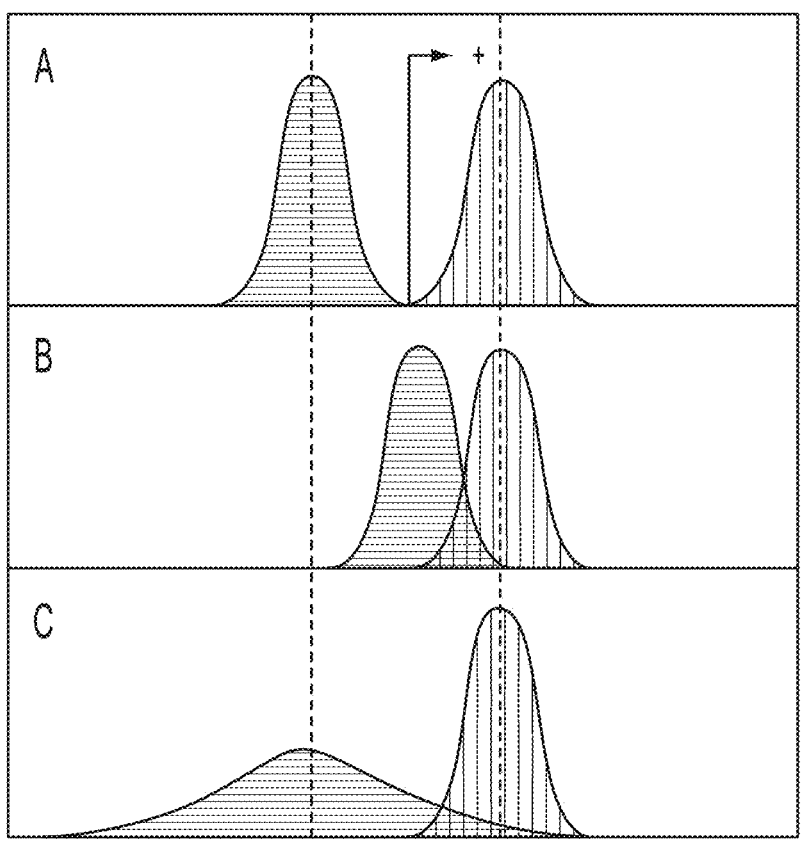
FIG. 4 certain aspects of isotype signaling and resolution sensitivity, according to some embodiments.

FIG. 4 depicts certain aspects of isotype signaling and resolution sensitivity. For example, as shown in panel A, the isotype signal on the left corresponds to a negative event, and the detected signal on the right corresponds to a positive event. Here, the negative population has a low background relative to the positive population, and the populations can be resolved easily (e.g. with a well-defined detection limit). In contrast, panel B shows a situation where the negative population has a high background relative to the positive population, and therefore it may be difficult to resolve the populations. Relatedly, panel C shows a situation where the negative population has a low background (relative to the positive population) and a high coefficient of variation (CV), and therefore it may be difficult to resolve the populations. Such a situation may be present where an isotype control presents significant spillover. Hence, in order to be able to resolve negative and positive populations, it is helpful to have a negative signal with low background relative to the positive signal, and to have a negative signal with a low spread or variance.

As discussed elsewhere herein, a dye on one probe can present an emission which spills over into a specific channel intended to detect emission from a dye of another probe. In such cases, the spillover may be analogous to the data spread of the negative population as described above.

In some cases, the broadness of the population in a secondary channel can increase due to data spread as caused by spillover from another fluorescent label on the same population detected in a primary channel, which can contribute to an increase in a detection limit in the secondary channel. For example, as the measurement error for a negative population increases, the distribution broadness can also increase. In some cases, there may be a large measurement error, and a detected signal in a secondary channel in the presence of spillover from a primary channel may be beyond an isotype control signal in a secondary channel in the absence of a spillover from a primary channel, yet may still correspond to a negative event. In some cases, spillover can contribute to an increase in detection limit. For example, an increase in the amount of spillover into a particular detection channel can operate to increase the detection limit for that channel. This may be associated with a larger measurement error which is caused by a more intense fluorescence detection on that particular channel.

In some cases, an isotype antibody can be used to obtain a baseline. In some cases, an unstained cell can be used to obtain a baseline. The greater the number of wash steps applied after staining during the process, the more likely the isotype functionality is to approach the functionality of the unstained cell population, with respect to the background fluorescence. That is, extensive washing can operate to equalize the background, such that even though isotype stain has been added, the washing acts to remove all of the nonspecifically bound isotype.

Following a staining protocol with a multicolor probe panel, there may be various fluorochromes associated with the cell surface. In order to assess specific positivity for an antigen as detected by a single certain conjugate on those cells, it may be helpful to take into account the emission of all other fluorochromes on those cells, which can operate to increase the detection limit for that particular single fluorochrome.

Fluorescence Intensity

Typically, flow cytometry involves the use of dyes or fluorochromes having certain properties, such as fluorescence intensity or brightness values. For example, the PE dye may have a brightness intensity of 3420000, whereas FITC may have a brightness intensity of 39000. These intensities can be measured as relative to each other, with one dye being chosen as a reference for maximum intensity. As discussed elsewhere herein, the intensity of individual fluorochromes can be considered when evaluating probe panels.

Distortion

A distortion of a background population and hence an increase of a detection limit can correspond to the number of overspilling fluorochromes on the cell surface or inside the cell or to the intensity of the related spillover signal into the respective detection channel. Hence, for example, a greater amount of spillover can correspond to a broader background distortion. In some cases, it is possible to consider the number of antibodies bound to the cell surface, such a greater number of antibodies labeled with that particular overspilling fluorochrome are considered to contribute more to the background distortion. In some instances, a database may contain estimates of the distortion of the background, for example based on assumed intensities that are typical for a certain cell type. In other words, the distortion can be based on the number of antibodies labeled with overspilling fluorochromes that are bound to this cell type.

As an example, it is possible to consider a T cell that expresses CD3 antigen along with some other coexpressed antigen Z. Typically, T cells have a very strong expression of CD3 on the surface. Hence, when staining with an anti-CD3 probe which is intended to provide emission signal to a particular channel, it is possible that the CD3 antibody dye conjugate probe in fact cross talks to the channel which is intended to detect for the Z probe, then the detection limit for the Z probe may be increased. When carrying out a multicolor experiment, complex spillover patterns may occur. For example, for a ten color experiment, it may be necessary to take into account spillover from nine other colors when considering one particular detection channel. That is, each of the other nine colors may contribute to an increase of the detection limit for that particular channel. In some cases, the distortion may be dependent on the cell type and the related expression patterns being analyzed. In some cases, the distortion may be dependent on the number of antibodies bound on the cell type which carry an overspilling fluorochrome.

Returning to the example of the anti-CD3 probe, it is possible to consider a T cell (high antigen density of CD3) and a B cell (absence of CD3 antigen), where both the T cell and B cell express a Z antigen. When staining a T cell with the CD3 probe, that dye can provide a spillover into the Z channel detector, thus increasing the detection limit of the Z channel. In contrast, when staining a B cell with that same CD3 probe, there is no (specific) binding because CD3 is absent on the B cell, and hence there is no spillover from the CD3 probe dye, and the CD3 probe is not considered to cause an increase in the detection limit on the Z channel. Hence, it can be seen that distortion factors may vary depending on the cell type and related antigen expression patterns. For example, a particular probe channel may result in one set of detection limits for one type of cell, and another set of detection limits for another type of cell. Relatedly, the set of detection limits for a particular probe channel may depend upon what types of antigens are expressed on the cells being analyzed.

For example, where a cell type is free of antigen A (and hence no binding by a probe specific for that antigen), an increase in detection limit may not be observed at a detection channel which is specific for antigen B. In contrast, where a cell type abundantly expresses antigen A (which is bound by a probe for antigen A, that also provides spillover to the detection channel for antigen B), then there may be an increase in the detection limit at the detection channel which is specific for antigen B. In this way, the increase in detection limit (or lack of increase) can be based on the expression pattern of the stained cells.

The distortion factor thus can have an impact on the detection limit. For example, where there is an increase in the detection limit (e.g. a one decade increase due to spillover), it may be necessary to observe or detect a greater signal at that channel in order to conclude that there is a positive event.

Figure 8:
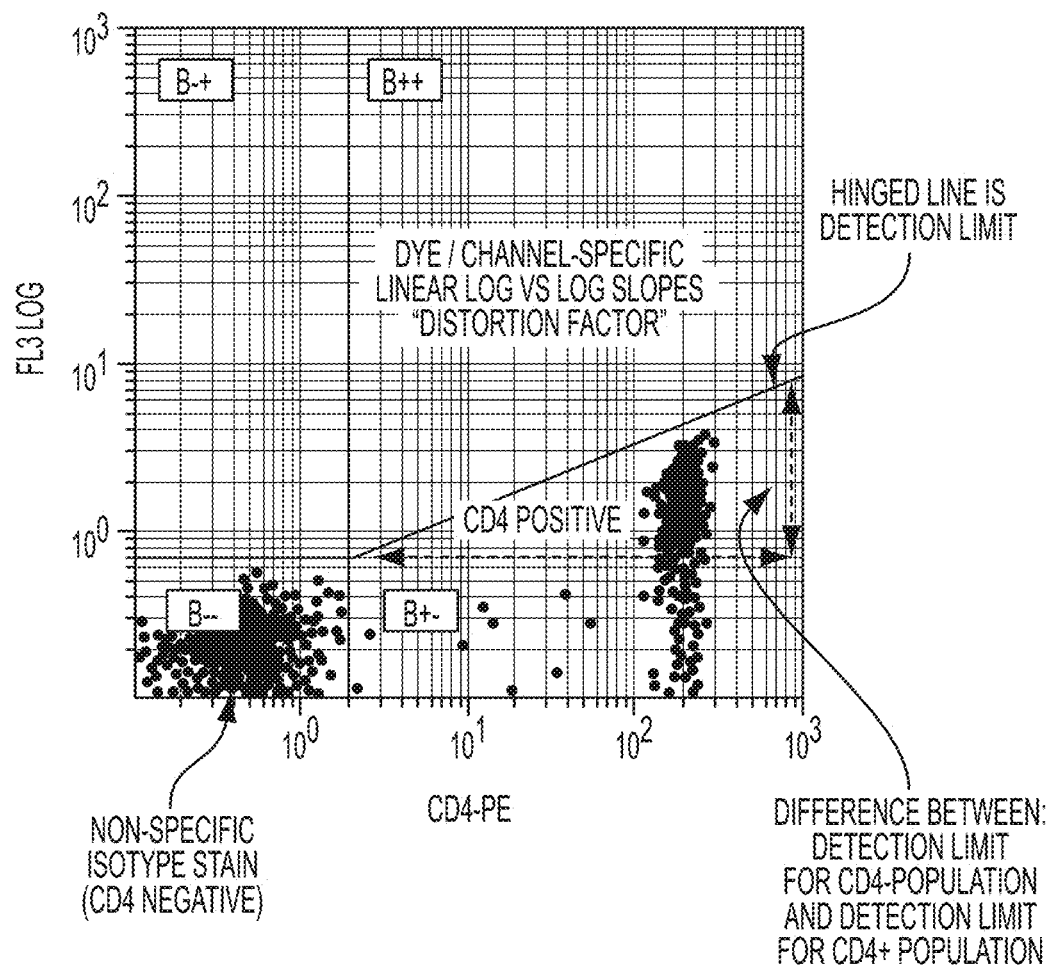
FIG. 8 depicts aspects of real data results from a staining protocol using a single antibody-dye conjugate, according to some embodiments.

For example, with reference to FIG. 8, it can be seen that there is strong spillover from the PE dye (of the CD4-PE probe) to the FL3 channel which detects ECD. Because of the spillover, the uncompensated ECD signal of the specifically PE-labeled population is a few hundred times brighter than the uncompensated ECD signal of the non-specifically PE-labeled background population, as compared to a non-specific isotype stain.

In some cases, with an increase in the signal, there is an increase in the spreading of the CD4+ population. Hence, there may be a larger PE signal on this population. Accordingly, for the FL3 label (y-axis) there may be an increase in the detection limit.

Compensation

Typically, a higher fluorescence signal may be accompanied by a higher absolute measurement error. For example, with reference to FIG. 5, the PE positive population causes a signal in the FL3 detection channel for ECD, due to spillover of the PE dye emission into the FL3 ECD detection channel, and hence the absolute errors may be much higher for this population. This can be represented as a standard deviation. In some instances, measurement errors may be affected according to Poisson distribution characteristics and cannot be reduced by compensation procedures, as these can only correct for the mean intensity of a population specifically labeled with overspilling conjugates versus a population non-specifically labeled with overspilling conjugates. If a comparison of relative measurement errors (as represented by respective coefficients of variation CV) indicates a sufficient degree of similarity, this can be a sign of linearity of detection.

In some instances, there may be a factor of two between coefficients of variation, such that the CVs are relatively similar and of same magnitude, and yet the standard deviation may be greater than 100 times different, or more.

Figure 6A:
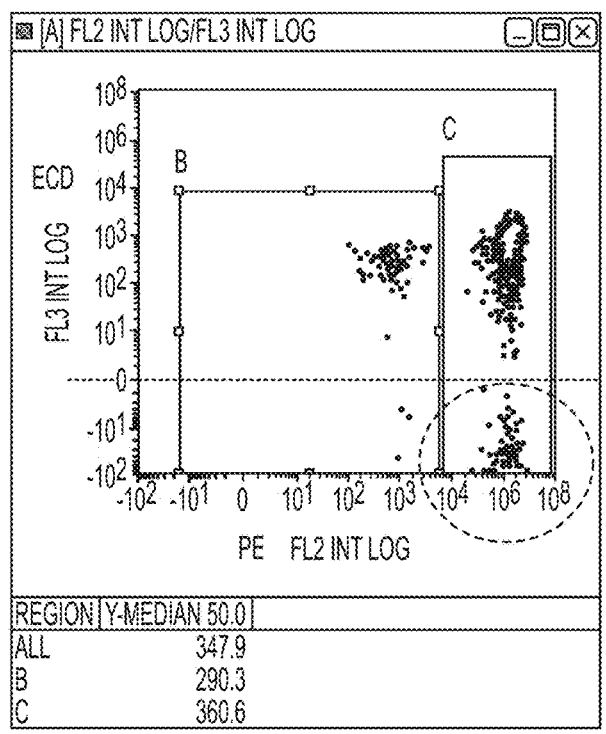
FIGS. 6A-6B depict aspects of a bimodal distribution for determining negative singal events, according to some embodiments.
Figure 6B:
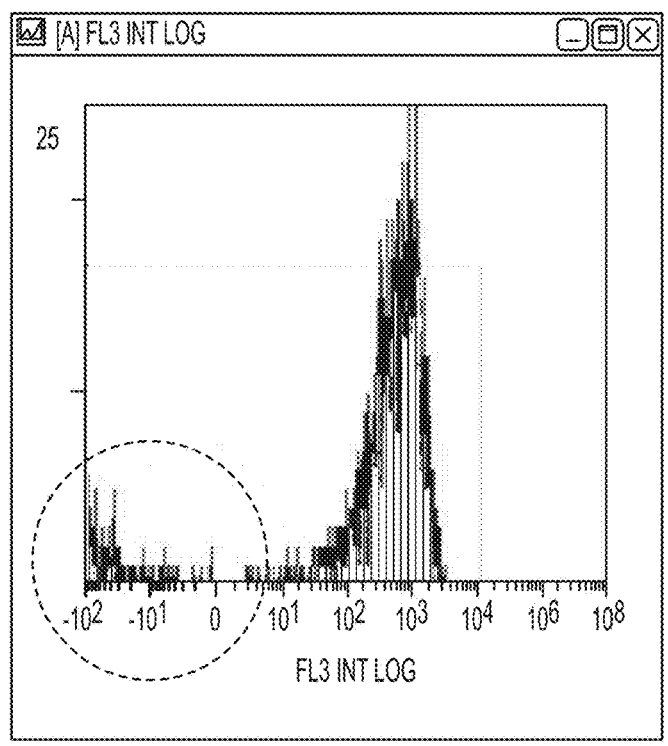
Figure 7:
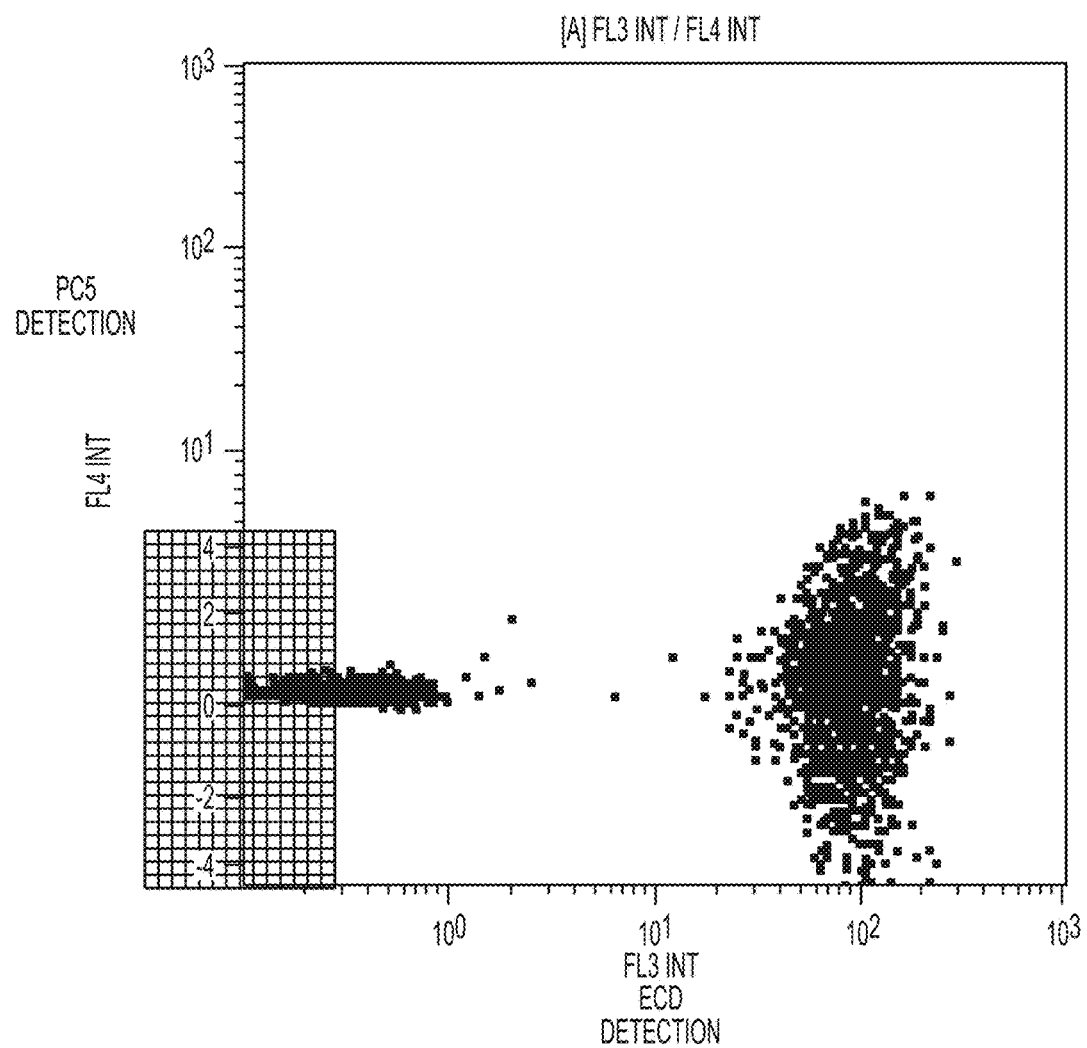
FIG. 7 depicts aspects of a broadened distribution of signal events, according to some embodiments.

As depicted in FIGS. 6A and 6B, negative fluorescence values, for the expression signal events measured by an PE detection PMT and by a ECD detection PMT, plotted against each other, can be artificially generated in a bimodal distribution through computational compensation. The bimodal calculation as shown can operate to distinguish events that are negative for the first of the two measured antibody-dye conjugates, the second of the two measured antibody-dye conjugate, or both of the two measured antibody-dye conjugates. FIG. 7 shows an increase in distribution broadness for the expression signal events measured by an ECD detection PMT and by a PC5 detection PMT, plotted against each other. FIG. 7, in part, reflects the fact that coexpression can affect the spread of a negative population into a spillover channel Although not shown in these figures, the spread for the positive events is equal to the spread for the artificially negative events.

Figure 5:
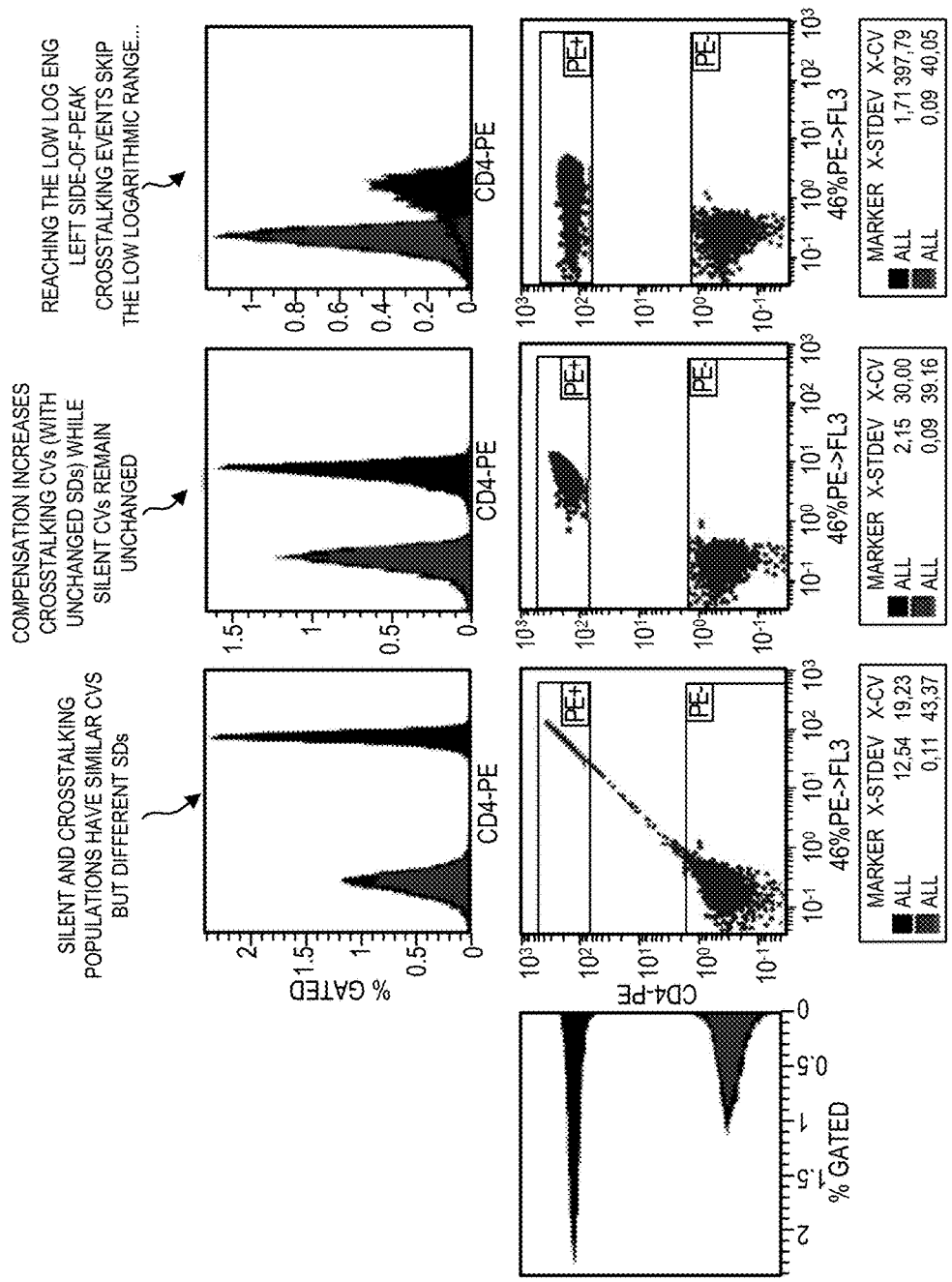
FIG. 5 depicts a comparison between coefficience of variance and standard deviation for expression events, according to some embodiments.

As shown in FIG. 8, there may be an increase in detection limit due to strong spillover. In some instances, calculations implemented via software and/or hardware can operate to correct for spillover, in a compensation procedure. At a certain point of compensation, the PE negative and the PE positive may have the same mean on the ECD axis, which may refer to a correct compensation (see, e.g. FIG. 5). As depicted in FIG. 5, the compensated PE positive population may have a larger measurement error, such that there is a greater data spread as compared to the PE negative population. Hence, there may be a certain range of ECD signal that is less intense than the increase of measurement error. Such signals may no longer be detectable as positive events. In some cases, there may also be a bifurcation of the compensated population.

When transforming a certain portion of the Y scale to linear scaling (see, e.g. FIG. 7), it is possible to compress the lower end of the logarithmic scale. Such transformation can indicate that the measurement error (e.g. broadness, or spread) of the ECD positive population is greater than that of the ECD negative population. In some cases, spillover from an FL3 (ECD) positive population to an FL4 (PC5) detection channel can translate to a larger measurement error after computational correction of mean intensities referred to as compensation. In some instances where there are cell-bound fluorophores that have spillover to an FL4 (PC5) detection channel, such dyes as ECD and PE that may be attached to antibodies which detect cellular structures on the same cells resulting in FL3 (ECD) and FL2 (PE) double-positive cells, there may be superposed spillover to the FL4 channel. This may translate to a superposed measurement error. It may be possible to account for such error. For example, each of the contributions to the overall data spread can be estimated as a linear value, and the linear values can be summed. The result may then be transformed to log value again. Further, a database may contain information regarding which antigens may be expressed on the same cell surface. Such information can be used for a basis for the selection of which of the spillover signals are to be combined for this population that is FL3 positive. Hence, there may be dyes that also have a spillover into the FL4 channel such as PE, however the antigens associated with such dyes may not be expressed on the same cell type that is FL3+, and thus do not contribute to the overall measurement error in this channel.

According to some embodiments, the cell type, or expression pattern or profile may have an impact on the results. For example, the results may depend on the pattern of antigens which is expressed on the cell, and which is recognized by the antibody dye conjugate probes. Because of potential spillover of some dyes into secondary channels, the detection limits for each of the fluorochromes may be influenced. In some instances where there is spillover, the population in the negative range of the scale may be spread or distorted, and the detection limits may increase. Typically, a particular expression pattern will be unique to a cell type. For example, it is unlikely that two different cell types would have identical expression patterns. In order to provide an estimation on the increase in a detection limit, it may be useful to identify which fluorescence signals will be present on the cells. Accordingly, techniques as discussed herein encompass identifying an expression pattern for use in evaluating probe panels.

The graph in FIG. 8 depicts results from a staining protocol using an antibody specific for CD4 antigen, conjugated with a PE dye. As shown here, the FL3 detection channel (sensitive to ECD dye emission) is registering spillover and hence background distortion from the PE fluorochrome.

As an example, it is helpful to consider a T helper cell which is positive for CD3 and CD4. In some cases, it may be desirable to evaluate the cell to see if a cytokine receptor such as CD25 (IL-2 receptor) or CD184 (CXCR4) is present. Often, a cytokine receptor will have a low copy number, and thus be dimly staining, on the surface of T helper cell. Hence, where it is desirable to assess cytokine receptor staining on the FL3 (ECD) channel, it may not be desirable to assign a T helper cell marker (e.g. CD4) on the PE channel. That is because the CD4+ cells which are stained with the PE label will present an increase in the detection limit at FL3 (ECD) where the cytokine detection is desired.

As depicted in FIG. 8, there is an increase in the detection limit, associated with the difference between the detection limit for the CD4− population and the CD4+ population. The line at the lower part of the y-axis delimits the CD population by limiting the negative population. This particular graph depicts a significant amount of spillover and hence background distortion from the PE emission spectrum to the ECD detection channel. Hence, the increase in detection limit is considerable. Comparing this result to the negative population on the left side of the graph, it can be seen that a substantial amount of sensitivity (e.g. about half of a decade) is lost. Accordingly, the number of copies that would be detected with the ECD label would need to be multiple times (e.g. 6×) higher (e.g. brighter signal) on a CD4+ population, as compared with a CD4− population, in order to be detected or registered as a positive event.

In a related example, it is useful to consider a different detection channel, such as the FL5 channel which is intended to detect emission spectra from the PC7 dye. In this example, the FL5 channel detects a certain wavelength that is more distant to the emission of the PE fluorochrome. Hence, there will be less spillover of the PE emission spectra into the FL5 channel, and thus the slope of the hinged line (e.g. as shown in FIG. 8) would be less steep. Put another way, the lower the amount of spillover into a particular channel, the lower the slope of the hinged line (e.g as shown in FIG. 8) associated with that channel.

The particular wavelength value is another parameter which may impact the result. Often, the wavelength range associated with a particular PMT or detector is at least in part determined by a bandpass filter that is in front of the filter. Typically, the larger the wavelength being detected by a particular PMT, the less sensitive the PMT will be, and hence the PMT will have a larger intrinsic error. For example, a PC7 detection channel may be configured to detect light larger than 755 nm wavelength, whereas a PE detection channel may be configured to detect light at a 575+/−15 nm wavelength. Accordingly, there may be more distortion associated with the PC7 channel. These effects can be factored into the database or table. Another factor which may be considered involves the amount of light spilling over into a secondary channel. For example, it may be useful to take into account the amount of light a particular dye would typically spillover over into another secondary channel. The properties of the secondary channel, with respect to intrinsic measurement error, which may depend on wavelength, can be considered.

As depicted in FIG. 8, the distortion factor is provided by the slope of the hinged line (detection limit). The distortion factor can be based on an intensity parameter (e.g. intensity of the PE dye signal). Further, a larger wavelength on the secondary channel on the y-axis can correspond to a larger slope. Hence, the distortion factor may increase with the wavelength. In some cases, this can be applied to the intensity of the PE signal. For example, the distortion factor of PE spillover to an ECD channel may be different from the distortion factor of PE spillover to an infrared channel, in that the distortion factor for the infrared channel will be larger. Relatedly, because the infrared channel may be at a greater spectral distance from the PE channel, the amount of spillover light may be less. Typically, PMT detectors can provide a good range of linearity, and hence a linear approach is useful. The overall distortion factor can be approximate to or correlate with the increase in the detection limit. As shown in FIG. 8, the distortion factor can be the slope of the hinged line the quadrant, and hence the detection limit can be determined in a linear fashion.

In one embodiment of a detection limit calculation, it is possible to obtain (i) the X value on the X-axis and (ii) the distortion factor or slope, and thereby generate the Y value or detection limit.

For instance, it is possible to provide the relative expression density FL(x) of a signal that would spillover (e.g. based on CD4 antigen density), and this value may be obtained from empirical data. It is also possible to provide the relative expression fluorochrome intensity FL(x), for example of the PE label, corresponding to the brightness of the fluorochrome.

An exemplary empirical approach may involve staining a T cell population with a CD4-PE probe, and evaluating the positive population (e.g. separated by 2.5 decades from a negative population). A table of results can be generated based on the data.

Hence, by inputting an X value (e.g. an estimate according to a typical expression density and dye brightness) along with a slope or linear relation, it is possible to determine the Y value or detection limit. Considering a probe panel that includes multiple antibody-dye conjugates, it is possible to obtain a distortion factor for each of the labels that provide a spillover to the FL3 channel. Results may vary according to the dye selected. For example, a CD4-PE probe may provide a greater degree of separation, and a CD4-FITC probe may provide a lesser degree of separation.

In some instances, the values may be linearized, added, and the sum of the linearized values subsequently transformed to a log value, so as to obtain a log distance. For each of the dyes, different distortion factors may apply. What is more, there may be different signal/noise ratios between positive and negative populations.

According to some embodiments, for a given conjugate combination, for a population of CD-Y, where CD-Y is a specific antigen of interest being measured by a single channel, an estimate of the "untouched" signal-to-noise ratio (S/N) distances can be given by:

$$FL(y) = \text{relative expression density } FL(y)*\text{relative fluorochrome intensity } FL(y)$$

where in the case of a modulated marker, the S/N distance FL(y) can be set to zero (0). For the given conjugate combination, an estimate of spillover from one or more populations of CD-X causing distortion into the channel measuring for CD-Y for each individual CD-X population can be given by:

$$\text{Distortion } FL(x) \rightarrow FL(y) = \text{Distortion factor } FL(x) \rightarrow FL(y)*\text{rel. expression density } FL(x)*\text{rel. fluorochrome intensity } FL(x)$$

where in the case that CD-X is a subpopulation of CD-Y, or CD-Y is an excluding marker set for CD-X, the S/N distortion of FL(x) into FL(y) can be set to zero (0). The distortions from each channel in a system having a plurality of channels (for example, 10 total channels and thus 9 CD-X channels) can be accumulated as given by:

$$FL(x) \rightarrow FL(y)\_\text{tot} = \log \Sigma 10^{\wedge}(FL(x;1 \ldots 9) \rightarrow FL(y))$$

The set of estimates and aggregation can be performed for each channel in a system, for each antigen of interest individually, allowing for the calculation of an effective S/N distance for each antigen as given by:

$$\text{Effective S/N distance} = FL(y) - FL(x) \rightarrow FL(y)\_\text{tot}$$

where the effective S/N distance for each antigen in each channel can be used to further determine detection limits for the overall system and panel.

According to some embodiments, the detection limit (DL) for the specific positivity of a fluorescent member of CD-Y, represented by FL(y), is a near-to linear function of positive spillover from fluorescence from a member of CD-X, represented by FL(x) according to the equations:

$$DL(FL(y)) = DLIC(FL(y)) + 256*(DF(FL(x) \rightarrow FL(y))*RI(FL(x)))$$

where DLIC(FL(y)) is defined as the detection limit of the fluorescence of CD-Y for an isotype control staining stated as coordinates between 0 and 1023; where RI(FL(x)) defined as the intensity of the fluorescence of a CD-X above its DLIC(FL(x)) stated in decades of FL(x); and where DF(FL(x)→FL(y) is defined as the distortion factor, measured as the increase of DL(FL(y)) per RI(FL(x)), stated in decades FL(y) divided by decades FL(x).

In some aspects. DF(FL(x)→FL(y)) can be calculated from the positive/negative compensation procedures and correlated according to the equation:

$$DF(FL(x) \rightarrow FL(y)) = (FL(y,x)*FLIC(x))/(FL(x)*FLIC(y))$$

where FL(y,x) is defined as the FL(y) intensity of FL(x) positive events, and where FLIC(x) and FLIC(y) are defined as the intensity of isotype control stainings for their respective antigens. The accumulation effects of overspilling compensated intensities from CD-X members, FL(x1, x2, . . . x(n−1)) into CD-Y can be given by:

$$DL(FL(y))\text{total} = DLIC(FL(y)) + 256 \log \Sigma 10^{\wedge}((DF(FL(x1,x2, \ldots x(n-1)) \rightarrow FL(y)*RI(FL(x1,x2 \ldots x(n-1))))$$

Such calculations are also described in the second paragraph of FIG. 1D.

According to some embodiments, isotype control data can be provided per patient gated on a scatter or "silently" stained (leukocyte) population. In other embodiments, compensation data can be generated per application (or per panel) by a positive/negative algorithm, where a mathematical or an experimental procedure for the calculation of a distortion factor can be established. In further embodiments, distortion matrix can be generation based on either or both of isotype and compensated data. Following compensation, a distortion matrix can be applied on every single event. In some embodiments, knowledge of compensation factors may not be sufficient to complete calculations as described herein. In other embodiments, knowledge of a distortion matrix, which can be determined experimentally on a given instrument or an instrument configuration and a set of dye, may be sufficient to complete calculations as described herein. In yet further embodiments, specifically positive gated values can be displayed in a way such as prism, a tree, a three dimensional overlay, a comparison plot, a profile plot, or the like.

With reference to FIG. 8, it can be seen that techniques can involve inputting or selecting a value for the X-axis, corresponding to expression density multiplied by the fluorescence intensity. Such data can be implemented in an antibody table module (and read or retrieved therefrom) as discussed elsewhere herein. In some cases, the values may be estimated. In some cases, the values can be based on experimental data. For example, it is possible to analyze CD4-PE staining experiments to obtain such data. Further, methods may involve multiplying the distortion factor by the intensity (real or estimated) of the marker. In some instances, the expression densities or marker patterns (e.g. for target cells) can have default parameters or values. Such information can be implemented in an antibody database module. As described elsewhere herein, the second paragraph of FIG. 1D provides additional details for exemplary detection limit calculations.

Figure 9:
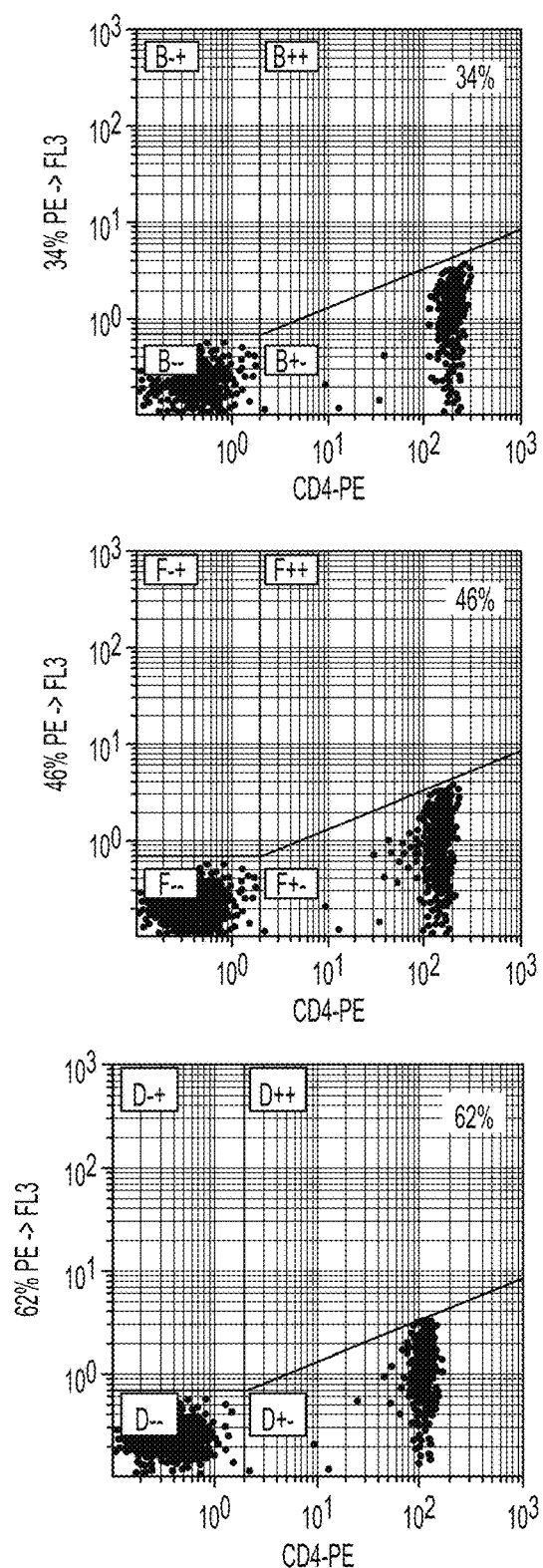
FIG. 9 depicts aspects of detection limits that are can be independent of, or adjusted for, compensation factors, according to some embodiments.

As depicted in FIG. 9, an increase of detection limits can be independent of compensation factors and/or PMT voltages. Rather, the detection limit and/or increase thereof can depend on emission spectra and filter configuration. As illustrated, configurations for how results are depicted can be tailored to remove distortion (or in other words, to apply a compensation factor) that may be caused by sensor readings from a desired PMT being incorrectly measured in combination with sensor readings from a separate PMT channel. Specifically, FIG. 9 displays detection results, sought from an ECD channel, with a percentage of sensor readings from a PE channel subtracted from the detection results. Three exemplary variations of PE channel subtraction are shown: one with 34% of the PE channel signal subtracted, one with 46% of the PE channel signal subtracted, and one with 62% of the PE channel signal subtracted. In each plot of detection limit results, the number of events identified as positive or negative changes, but the detection hinge line between the two compared populations remains the same. The removal of distortion provides for a more accurate and sensitive result set.

FIG. 10 shows aspects of an exemplary spillover pattern distortion matrix for certain dyes, according to some embodiments. The spillover may be independent of PMT settings and compensation factors, and may be dependent on fluorochromes, filters, and precision of alignment. In aspects as illustrated, the spillover matrix can be qualitative, to quickly display to an operator the effect at the interface of particular dyes or PMT detectors.

Figure 11:
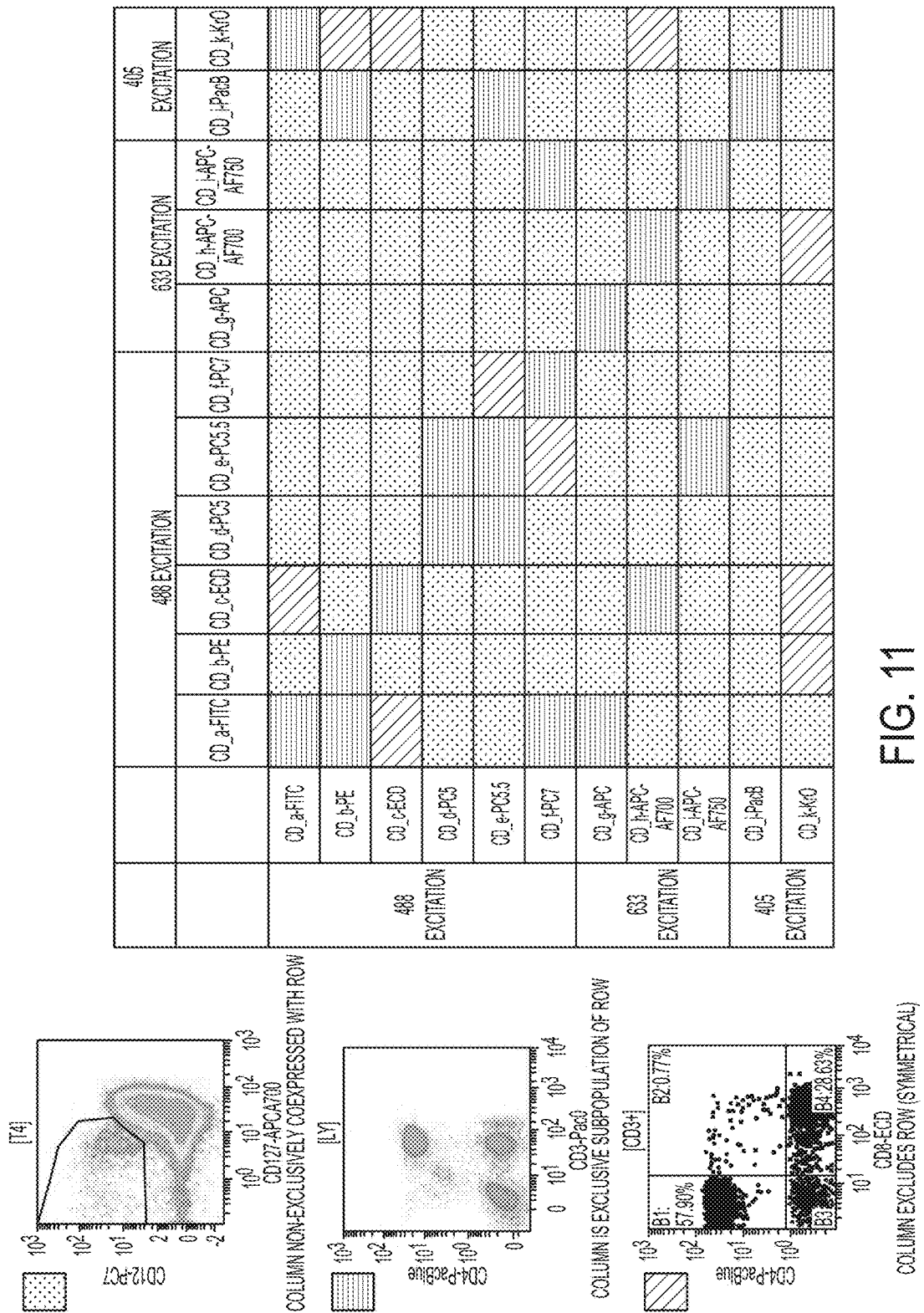
FIG. 11 depicts aspects of a coexpression matrix, according to some embodiments.

FIG. 11 shows aspects of a coexpression matrix according to some embodiments. In aspects as illustrated, the coexpression matrix can be qualitative, to quickly display to an operator the effect at the interface of particular antigens, dyes, or PMT detectors. As illustrated in FIG. 11, a coexpression matrix can indicate interactions where: a column is non-exclusively expressed with a row, a column is an exclusive sub-population of a row, or where a column is mutually exclusive of a row (providing for a symmetrical plot of expression events).

Figure 12A:
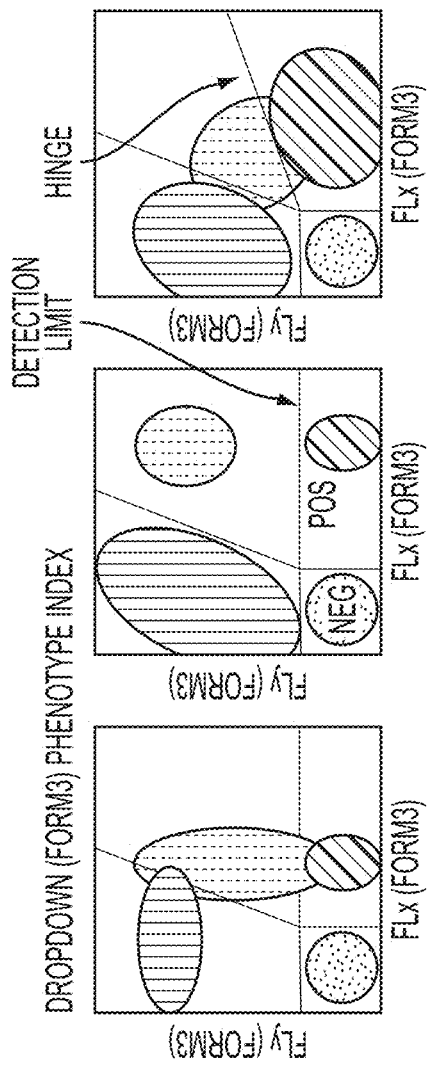

FIG. 12A depicts estimates of schematic staining patterns according to some embodiments. Where there is positivity for a certain marker overspilling to another channel, a hinge may be observed, as shown in the right graph. The user may change certain inputs into a simulation, so as to vary the output shown. For example, a user may select or change various dyes or antibodies contained in a probe panel, so as to obtain an improved sensitivity for a certain coexpressed antigen. The situation shown in the middle graph of FIG. 12A is particularly desirable, as the detection limit of the FL(x) positive population is not influenced by the FL(x) positivity, as compared to the negative.

Figure 12B:
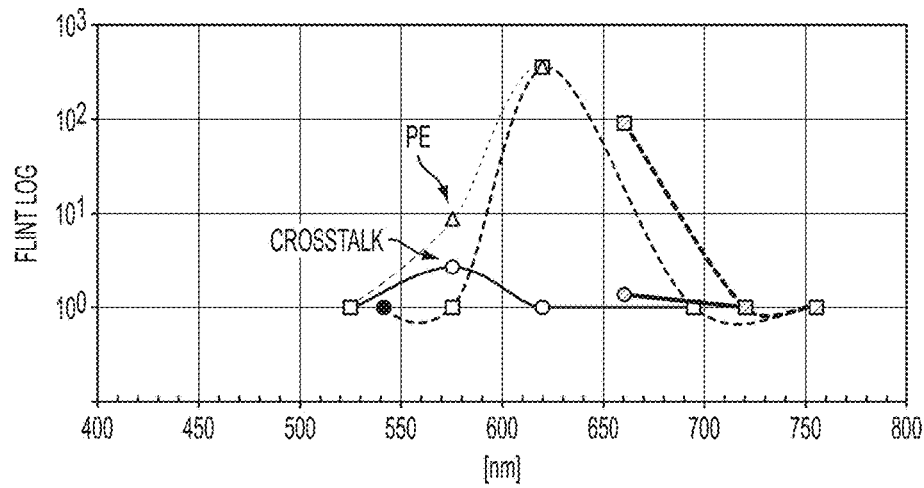
Figure 12C:
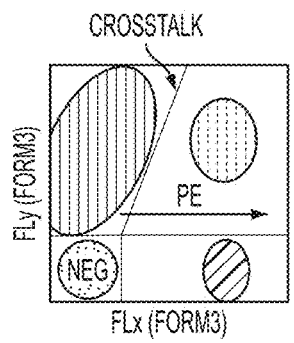

FIG. 12B depicts a variable PE detection limit signal according to some embodiments. The PE signal of FIG. 12B can correspond to the horizontal direction depicted in the graph of FIG. 12C. That is, the spillover that is manifested in FIG. 12B can also be manifested in FIG. 12C resulting in a variable PE detection limit that depends on the fluorescence intensity of the overspilling dye whose intensity is scaled along the y-axis. In comparison, in FIG. 12D the overspilling antigen has been moved to a position where it exerts no spillover to the PE channel (e.g. CD45 moved from ECD excited the blue laser to APC excited by the red laser with a very strong signal), such that the CD45-APC signal does not impact the background at the PE channel. Further, the PE and APC fluorophores are excited by different laser wavelengths. Such non-spillover situations may be rare, particularly in multi-color (e.g. 10) panel configurations, because typically there will be fluorescent labels on the cells which influence detection limits at various channels.

Figure 12E:
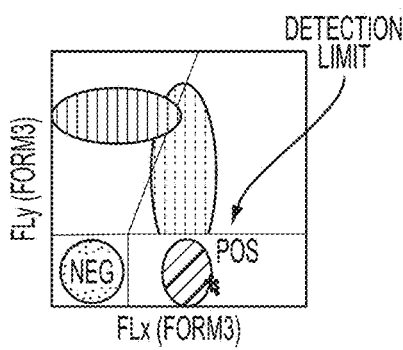

In FIG. 12E, there is a high sensitivity for the expression of antigen Y on cells that are positive for antigen X. This may be a desirable situation where the expression of Y is prioritized. When comparing the negative and positive populations, the detection limit is not altered. There is a low detection limit for FLy, on the FLx population. According to some embodiments, FIG. 12E may refer to a special situation involving high expressing cells of a non-exclusive co-expressed antigen that are at risk to be specifically detected. In some cases, it may be helpful to refer to an uncommented doublet of FIG. 12C.

Figure 12F:
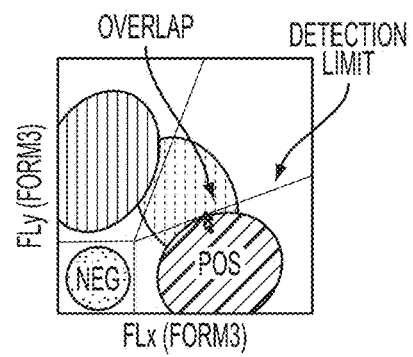

In comparison, in FIG. 12F it can be seen that the detection of antigen X labeling on the cell involves a fluorochrome emission that influences the detection limit on FLy. An overlap of populations is also shown. In contrast, there is no such overlap in FIG. 12E (or an uncommented doublet of FIG. 12C). Hence, a user that obtains results such as those depicted in FIG. 12E may decide to proceed with that particular probe panel. In contrast, if this coexpression is prioritized, a user obtaining results such as those depicted in FIG. 12F may decide not to proceed with that particular probe panel.

Figure 12G:
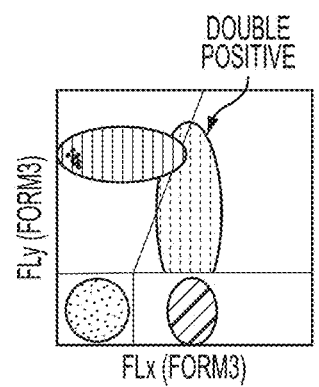
Figure 12H:
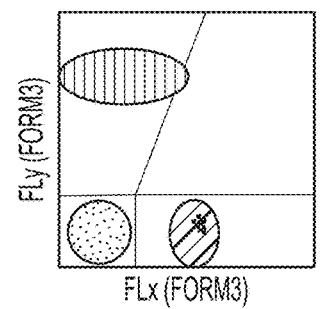

FIG. 12G (as well as an uncommented doublet of FIG. 12C) depicts a bivariate dot plot showing a double positive event. FIG. 12H depicts a similar bivariate dot plot, where there is no double positive event. The plot of FIG. 12H is representative of a result for an exclusion.

Figure 12I:
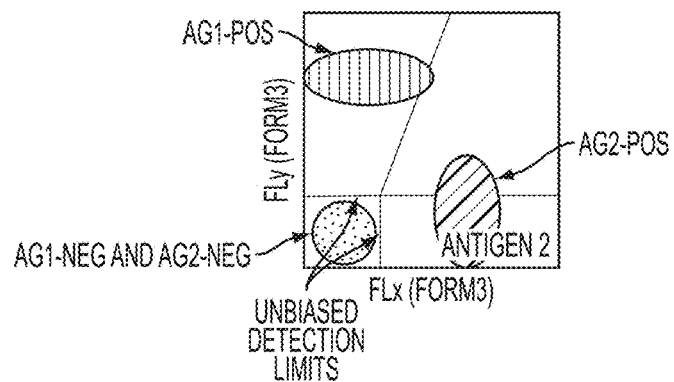

FIG. 12I depicts another exclusion situation, where there are no double positive events, which may present an acceptable result for the user. Considering the negative for Antigen 1, which excludes Antigen 2, it can be seen that these two antigens do not occur on the same cell type. Hence, a user that is interested in evaluating for Antigen 2 on a cell characterized by the lower left quadrant can observe an unbiased detection limit. The user would not look to a cell expressing Antigen 2, because due to the biological characteristic of the cell, a double positive population does not occur. Hence, a double positive may not be a target population in the analysis. The discrimination between the Antigen 2 positive (AG2-POS) and the Antigen 2 negative (AG2-NEG) can, however, be a target of the analysis. Similarly, the discrimination between the Antigen 1 positive (AG1-POS) and the Antigen 1 negative (AG1-NEG) can also be a target of the analysis. In each of these situations, the detection limits are unchanged.

Because there is no expression of Y antigen on X positive cells, nor any expression of X antigen on Y positive cells, the upper right quadrant is not populated.

Figure 13:
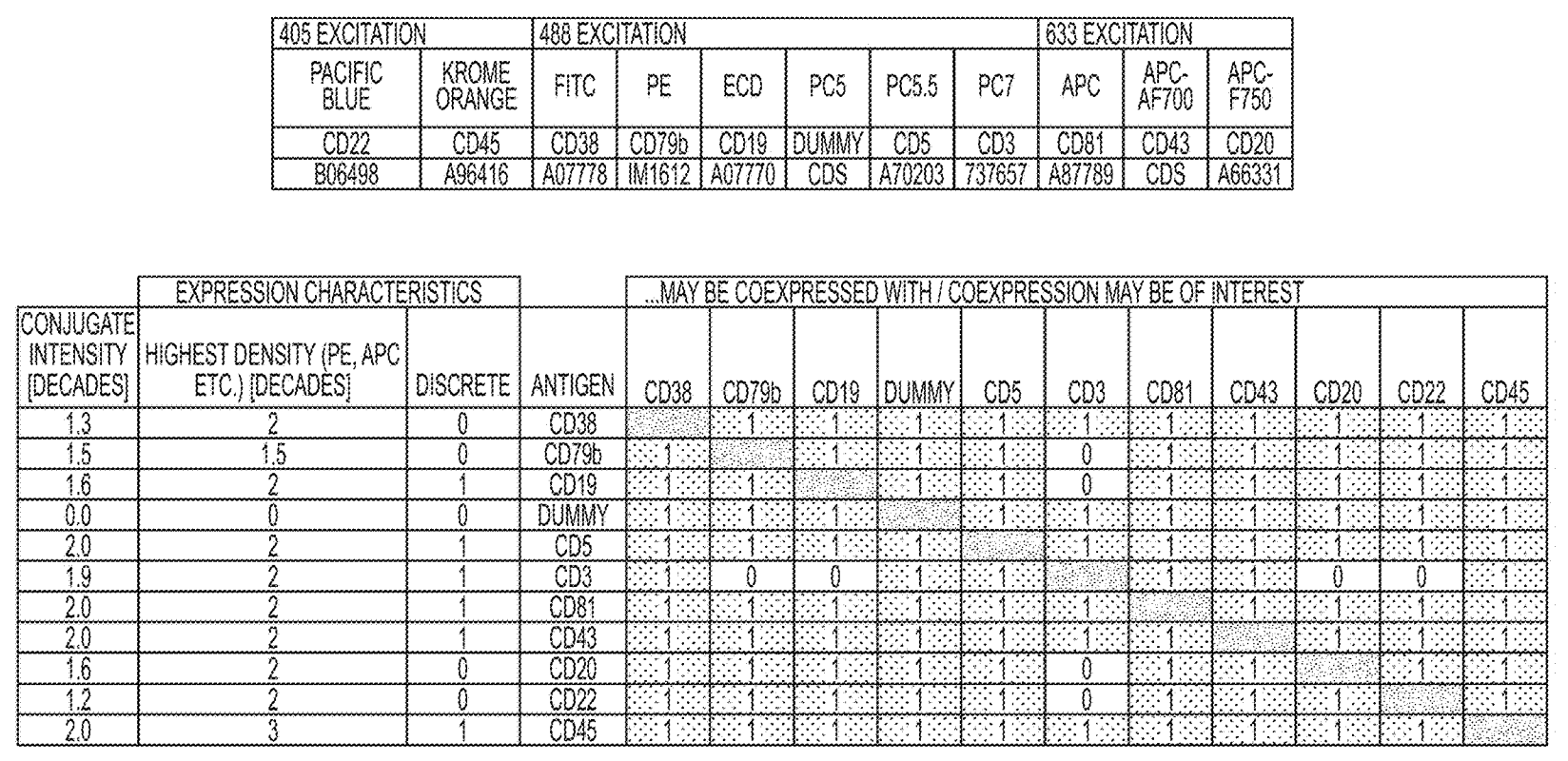

FIG. 13 depicts aspects of probe panel evaluation systems and methods according to some embodiments. In some cases, expression patterns can be categorized based on various criteria. For example, in some embodiments, expression patterns can be categorized as normal, lymphoproliferative, or immature blood cell disorders. As shown here, various factors can be taken into account for expression patterns, such as fluorescent intensity and the like. In some cases, the cells in the upper table of FIG. 13 identifying expression characteristics can be annotated with a "1" to represent marker coexpression, and with a "0" to represent the absence of marker coexpression. In some cases, the cells in the lower table of FIG. 13, also identifying expression characteristics, can be annotated with a "0" to represent descendant-to-parent marker coexpression, and with a "1" to represent the absence of descendant-to-parent marker coexpression. Accordingly, this data can be used to indicate whether a fluorochrome label may or may not result in an increase of detection limit for a secondary fluorophore label. For example, where there is no coexpression, then it may be possible to not take into account the fluorescent label on the cell. That is, there will be no production of a spillover signal, due to the absence on the same cell, and hence there will be no increase in detection limit. As discussed elsewhere herein, embodiments of the present disclosure encompass aspects of other expression patterns, such as parent-descendent patterns. Expression pattern information can be used to determine whether a measurement error at a certain channel for a certain population with a certain expression pattern will effectively be increased or not. Relatedly, expression pattern information can be used to estimate or determine distortion, and/or for superpositioning. In some cases, exemplary tables account for spillover that occurs so as to provide a combined distortion result.

Figure 14:
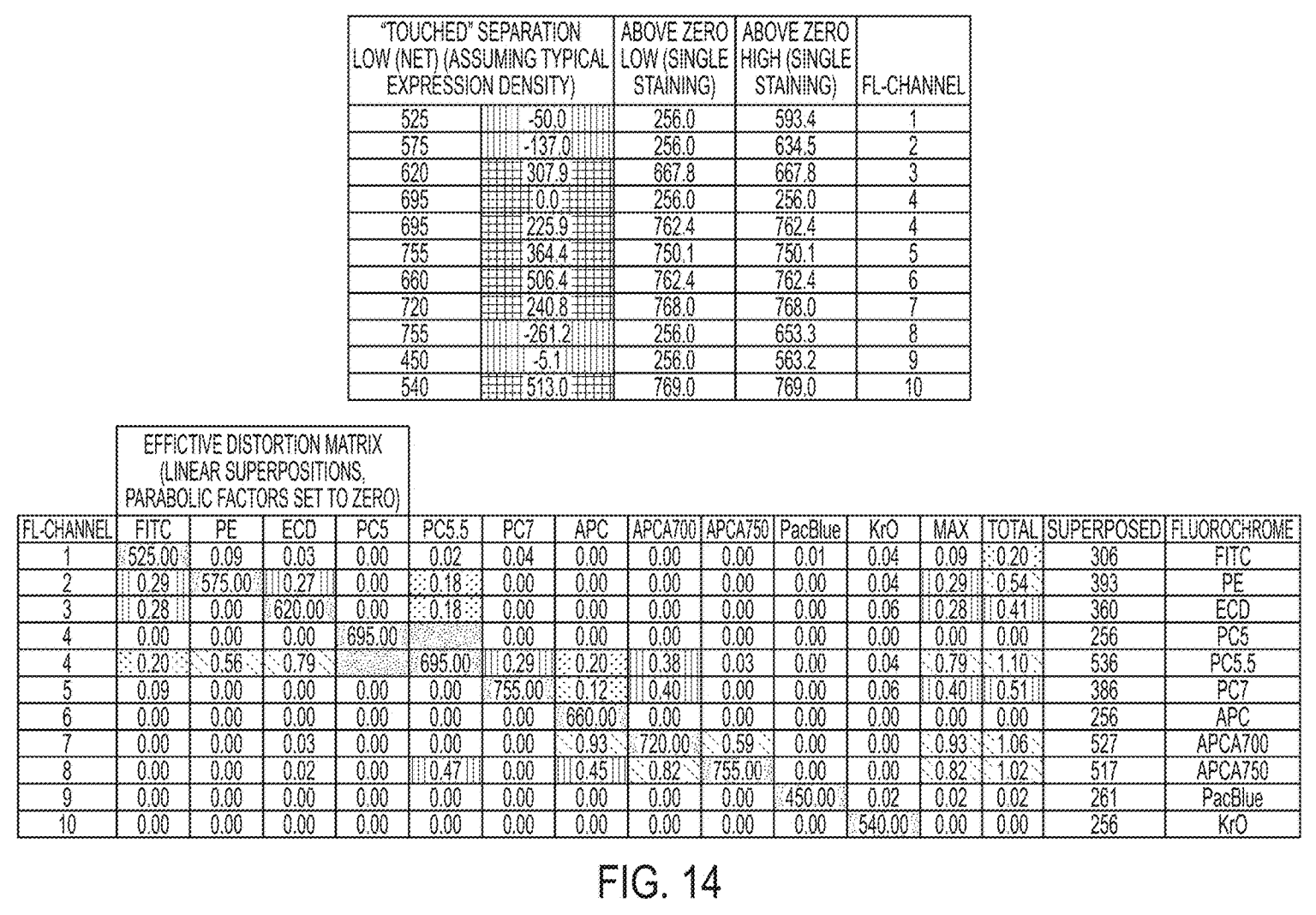

FIG. 14 depicts aspects of probe panel evaluation techniques, particularly numeric simulation techniques, according to some embodiments. The tables provided as FIG. 14 display, in part, the relative contributions of various fluorochromes, exited by one or more excitation lasers and detected in FL-channels (i.e. PMT channels). The relative contributions provide a basis for correction, the removal of parameters or events undesirably measured by a given PMT relating to fluorochromes to be measured by another PMT detector and channel. An effective distortion matrix can be calculated to determine such relative contributions for any given combination of excitation lasers, fluorochromes and PMT detectors.

FIG. 15 depicts aspects of probe panel evaluation techniques, particularly spillover pattern techniques, according to some embodiments. The tables provided as FIG. 15 display, in part, the relative brightness of the given fluorochromes in relation to a single fluorochrome of the set, chose as the reference for 100% brightness or intensity in that panel of dyes. The spillover pattern and relative brightness can be further classified as creating a particular level of distortion, indicating the relevance of a particular fluorochrome member in affecting the detection of other fluorochromes by related PMT detectors. These values can be used to calculate an increase of detection limits, per decade of distorting signal intensity, for each given combination of channel or dye.

Figure 16A:
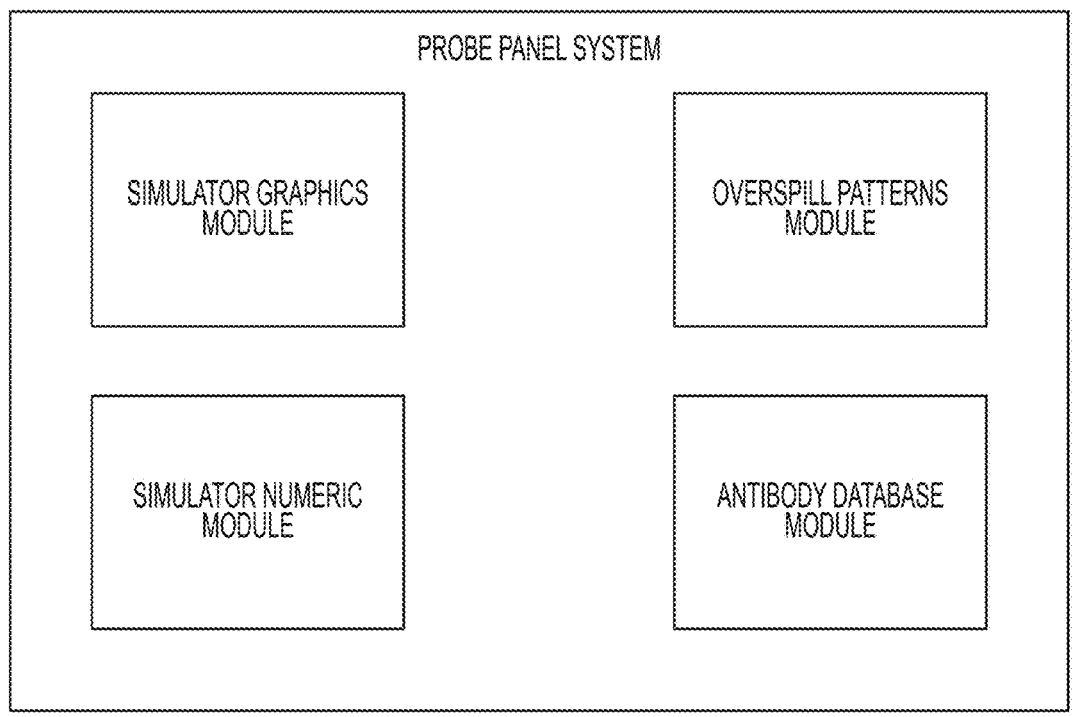
FIG. 16A depicts an exemplary schema for a probe panel system, according to some embodiments.

FIG. 16A illustrates an exemplary schema for a probe panel system according to some embodiments. As depicted here, the system includes a simulator graphics module, a simulator numeric module, an spillover pattern module, and an antibody database module. The simulator graphics module can be used for user input of aspects of a desired antibody panel, for the graphical output of simulation results, and for the modification of default simulation parameters. The simulator numeric module can be used for the numerical output of simulation results. The spillover patterns module can be used for default simulation parameters for fluorochrome properties and distortion factors according to standard optical filter sets. The antibody database module can be used for default simulation parameters for antigen expression densities, coexpression patterns, and parent-descendant schemes.

In some cases, for example as shown in FIG. 13, the simulator graphics module can be configured to implement user input related to an antibody panel, the display of default data on the coexpression of antigens (e.g. "may be coexpressed with/coexpression may be of interest"), the display of default data on subpopulation coexpression of (e.g. "(bright expressing) cells are not an (exclusive) subpopulation of"), the display of estimated data on conjugates' decades of mean signal intensity above positive-negative threshold, and the graphical output of simulation results.

FIGS. 16B and 16C depict aspects of a user input module for a probe panel according to some embodiments. Following user input of antigen specificity the respective part numbers (PN) can be retrieved from the Antibody Database module and displayed in the fields below the user input fields. For unoccupied channels, the user may input a dummy designation. Where antibody-conjugates are not available in the repertoire of the Antibody Database, and where the antigen specificity is available albeit conjugated to dye labels other than those desired, it is possible to designate such as Customer Design Service (CDS).

FIG. 16D depicts aspects of a simulator graphic module according to some embodiments. As shown here, the system may provide a display of default data on the coexpression of antigens (e.g. "may be coexpressed with/coexpression may be of interest"). In some cases, the source range (e.g. normal, lymphoproliferative, or leukemic disease, corresponding to expression pattern, can be switched or selected by entering 0, 1 or 2). The specificities as provided by a user can be displayed, for example as column and row headers. In some embodiments, the system can be configured to receive input from the user so as to override default data. In some embodiments, table entries can be overwritten by a user if needed or desired. In some cases, coexpression data (e.g. default entries) can be retrieved from the Antibody Database module. As indicated here, a value of "1" can represent a True case, such that coexpression occurs and is of interest. Relatedly, a value of "0" can represent a False case, such that antigens are not coexpressed, or their coexpression is not of interest. Such coexpression data can be stored in the Antibody Database module and retrieved therefrom. There is symmetry along the diagonal axis of the blank fields.

FIG. 16E depicts aspects of a simulator graphic module according to some embodiments. As shown here, the system may provide a display of default data on the parent-descendant relationships of antigens (e.g. "(bright expressing) cells are not a descendant population of"). Again, a source range can be switched by entering 0, 1 or 2. As further shown here, antigen specificities according to user input can be displayed as column and row headers in the table. In some cases, entries may be overwritten by a user if needed or desired. In some cases, parent-descendant data (e.g. default) can be retrieved from an Antibody Database module. A value of "1" can represent a true case, where positive cells (column antigen) are not a descendant population, and therefore cause distortion in channel of row antigen. A value of "0" can represent a false case, where positive cells (column antigen) are a descendant population, and therefore do not cause distortion in channel of row antigen. For example, according to the table shown here, lambda is not a descendent of kappa, whereas FMC7 is a descendent of CD19. According to some embodiments, FMC7 may also be kappa negative.

Figure 16F:
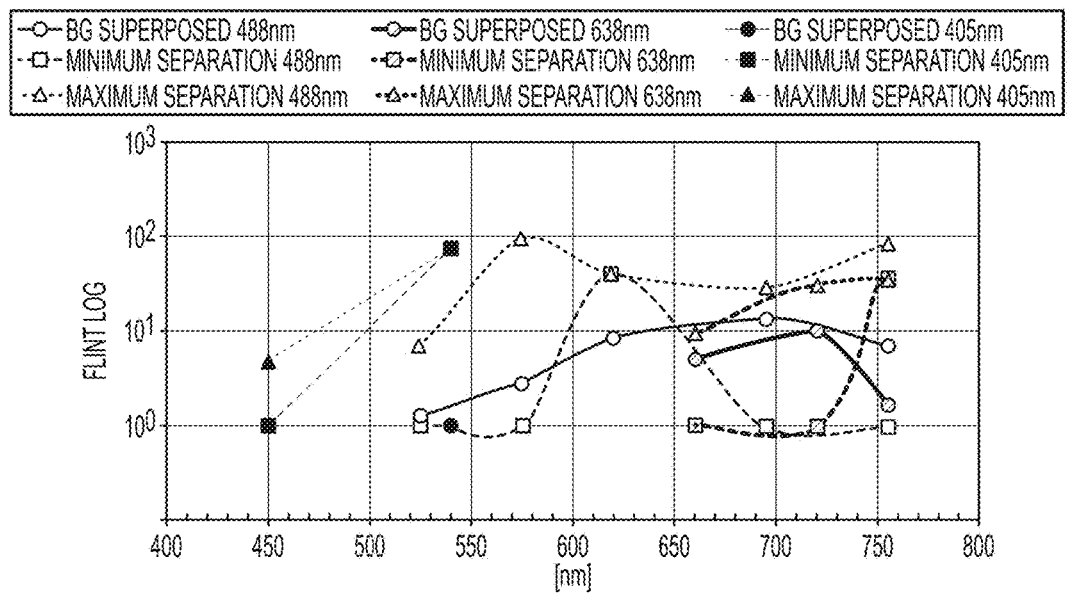
FIGS. 16F-16G depict aspects of simulator graphic modules for predicted result profiles, according to some embodiments.

FIG. 16F depicts aspects of a simulator graphic module according to some embodiments. As shown here, different curves or lines can correspond to different excitation wavelengths. Here, the wavelengths are 488 nm, 638 nm, and 405 nm. The circles, connected by solid lines, correspond to the background for most complex expression patterns. The squares, connected by dashed lines, correspond to the lowest expected fluorescence intensity for a conjugate. The triangles, connected by dotted lines, correspond to the brightest expected fluorescence intensity for a conjugate. Each individual indicator (i.e. circle, square, or triangle) is positioned above an X-axis value corresponding to a central wavelength for a particular bandpass filter or detection channel range. The Y-axis represents upper four log decades of fluorescent intensity, with a negative population centered in the lowest decade. As discussed elsewhere herein, for an antigen having discrete expression characteristics, the dashed and dotted lines will coincide for a respective X-axis location (bandpass wavelength). Further, as discussed elsewhere herein, it is possible to rank various probe panel designs based on distances between various indicators. For example, probe panel designs can be ranked based on a maximum distance between a triangle (dotted line) and a circle (solid line) and can also be based on a minimum distance between a square (dashed line) and a circle (solid line).

In some cases, ranking may involve prioritizing probe panels that correspond to complex spillover patterns and which are associated with dimly expressed antigens.

Figure 16G:
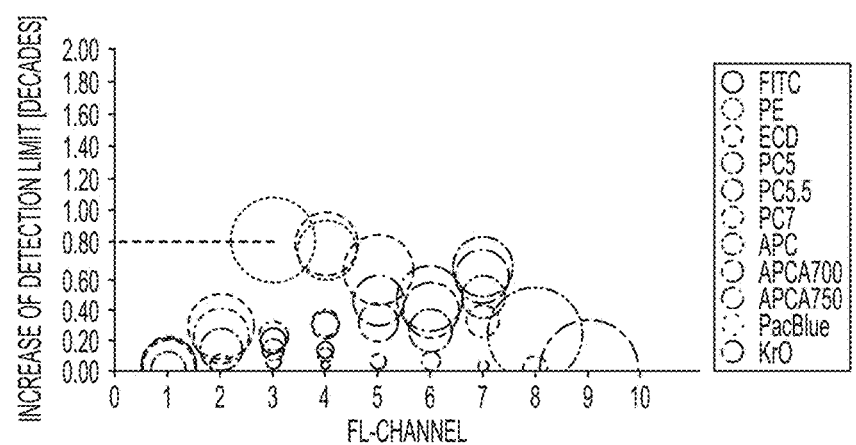

FIG. 16G depicts aspects of a simulator graphic module according to some embodiments. Here, a display of all distortion contributions for a particular detection channel are positioned above each individual channel. The circles or bubbles can be coded (e.g. color coded) according to the respective overspilling fluorochrome. The value or intercept on the Y-axis indicates an absolute increase of detection limit in decades caused by a conjugate in a respective channel. For example, the Y-axis can represent an increase of background, in decades, where 0.00 is a threshold between the first and second decades (e.g. negative population centered in first decade). The diameter of the circle can represent the relative contribution of a conjugate to the overall background distortion in a respective channel. As discussed elsewhere herein, in order to lower the background distortion for a given channel, it may be helpful to address for example the largest circle positioned above that particular channel. In some cases, it may be useful to minimize or reduce the number of circles for channels used for the detection of modulated antigens.

FIG. 16H depicts aspects of a simulator numerics module according to some embodiments. As shown here, the table includes values for all absolute distortions resolved per overspilling conjugate (column titles) and distorted channel, and also illustrates an increase in backgrounds in decades per decade of signal intensity of the spillover ing fluorochrome in its primary channel. Further included are columns for the size of maximal contributions to total background distortion and total distortions of the background. The superposed column indicates a quadrant or region position in a graphical scale of 1024 units of a positive-negative threshold according to a position parameter. Also shown is source data for the graphical representation of background distortion.

According to some embodiments, it is possible to determine an absolute distortion caused by a single spillover ing conjugate based on the following formula:

(conjugate intensity)*(distortion factor)*(coexpression index)*(parent-descendent index)

According to some embodiments, the conjugate intensity may be represented in decades, and can be determined as an estimate based on antigen density and fluorochrome brightness or by usage of emperical data on conjugate intensity.

According to some embodiments, it is possible to determine a total distortion in a given channel based on the following formula:

$LOG_{10}$(sum of linearized absolute distortions caused by each conjugate)

According to some embodiments, a positive-negative threshold region/quadrant position can be determined based on the following formula:

(decades of total distortion)*(256)+256 where 256 is the graphical threshold between the first and the second decade assuming that the negative population is delineated by this graphical threshold.

FIG. 16I depicts aspects of a simulator numerics module according to some embodiments. The table shown here includes linear relative distortion contributions resolved per crosstalking conjugate (column titles) and the distorted channel in decades. This table can provide source data for the graphical representation of background distortion (e.g. graphics, "distortion contributions"). Table values can be based on the following formula:

$$\text{relative contributions to distortion} = \frac{[\text{linear absolute distortion}]}{[\text{linear total distortion}]}.$$

FIG. 16J depicts aspects of an spillover pattern module according to some embodiments. The table shown here includes distortion factors, which can be applied per decade of crosstalking (i.e. overspilling) fluorescence intensity and can be determined experimentally or based on the following approximative equation:

distortion factor=[crosstalk index]*[bandpass temperature factor]

Figure 16K:
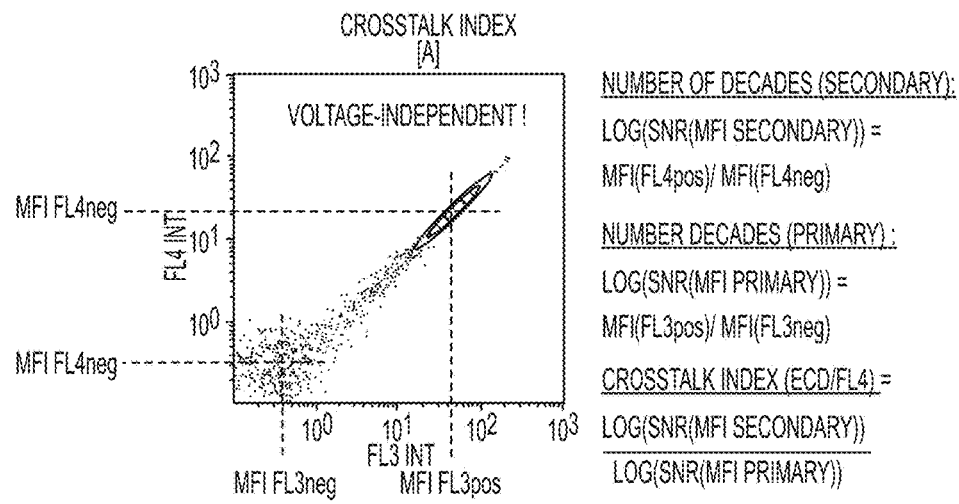
FIGS. 16K-16L depicts aspects of spillover pattern modules, according to some embodiments.

FIG. 16K depicts aspects of an spillover pattern module according to some embodiments. A definition of crosstalk index can be seen herein as:

Crosstalk index=LOG(SNR(secondary signal))/LOG(SNR(primary signal));

where: SNR=signal-to-noise ratio=MFI (positive population)/MFI (negative population);
and with MFI=mean fluorescence intensity.

Figure 16L:
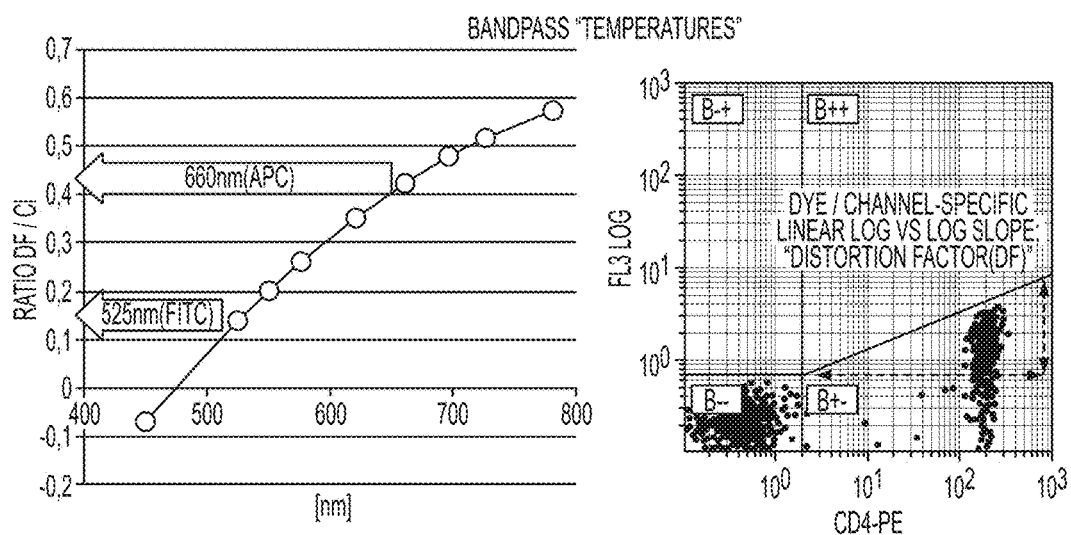

FIG. 16L depicts aspects of an spillover pattern module according to some embodiments. As shown here, for 525 nm (FITC) the absolute distortion can be calculated according to the following formula where the ratio of DF (distortion factor) to CI (crosstalk index) is 0.15:

absolute distortion=0.15×LOG(SNR(secondary))

That is, there are 0.15 decades of distortion per decade of secondary signal intensity. As also shown here, for 660 nm (APC) the absolution distortion can be calculated according to the following formula where the ratio of DF to CI is 0.42:

absolute distortion=0.42×LOG(SNR(secondary))

That is, there are 0.42 decades of distortion per decade of secondary signal intensity in the APC channel (660/20 bandpass).

FIGS. 16M and 16N depict aspects of an antibody database module according to some embodiments. The table in FIG. 16M includes data for antigen expression densities (e.g. scaled according to CD8-PE=2.5 decades of intensity above pos-neg threshold), part numbers, and expression characteristics (e.g. 0=modulated, 1=discrete). The table in FIG. 16N includes data for coexpression patterns (e.g. "may be coexpressed with/coexpression may be of interest"). As shown here, there is a symmetry in the table along the diagonal table cells.

Figure 16O:
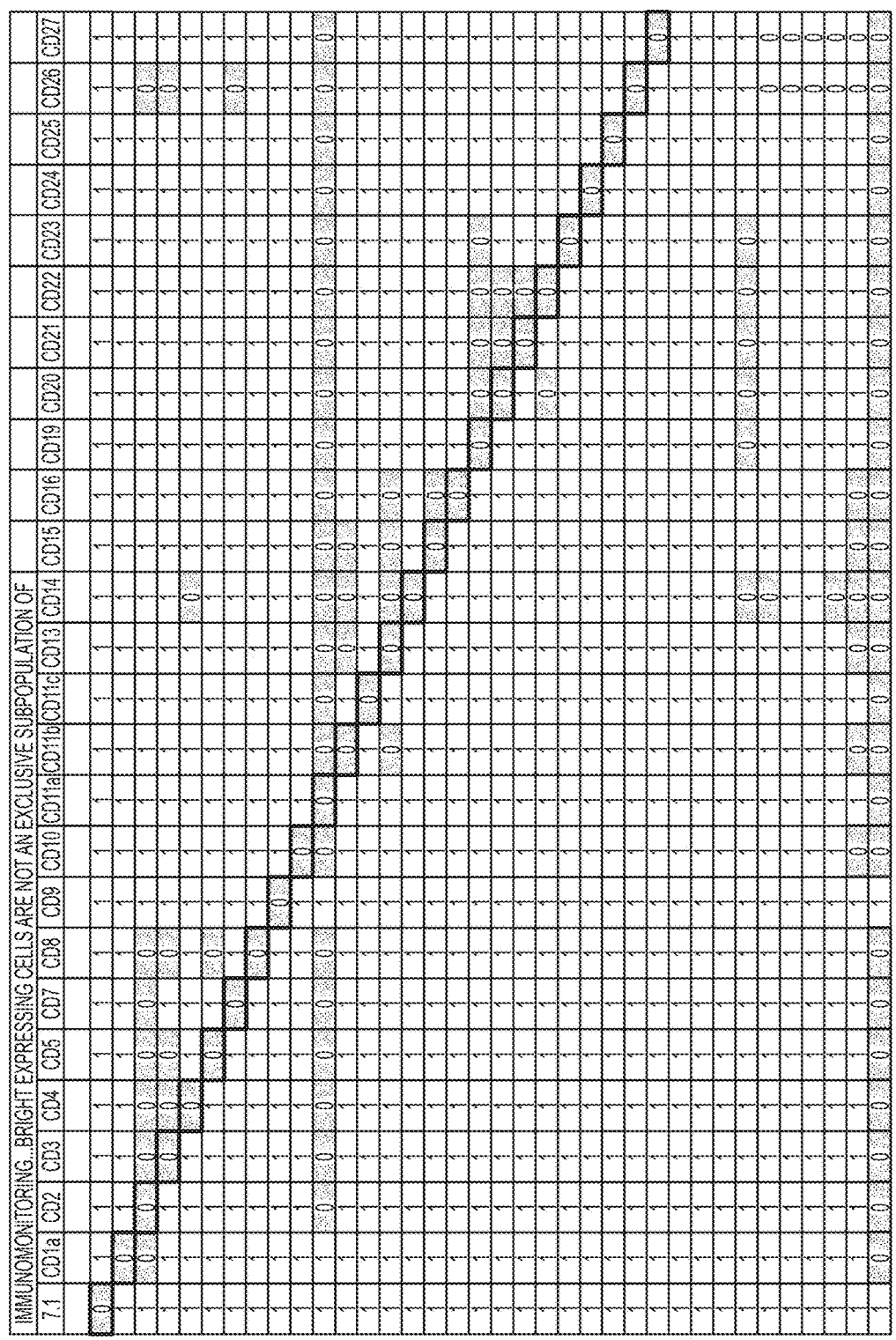

FIG. 16O depicts aspects of an antibody database module according to some embodiments. In some embodiments, antibody database modules can include information concerning parent-descendant patterns (e.g. "(bright expressing) cells are not a descendant population of"), and may be asymmetric. According to some embodiments, such database information can include estimated values. According to some embodiments, such database information can include emperical values.

FIG. 17 depicts aspects of a numerical approach to model spillover patterns, according to some embodiments. As shown here, the evaluation of spillover patterns may involve a detection radar approach to process a multivariate data set. As shown in FIG. 17, the multivariate radar representation can display detection limits for antigens according to their detection channels as they are arranged in their panel setup 1702. As shown in a first image layer 1704, each radial axis of the detection radar represents a fluorescence channel from the third to sixth decade of measured signal, each decade being a 20 bit segment. The first interior shaded portion 1706 represents untouched detection limits, within and below that decade, assuming that the isotype control is centered in the third decade. As shown in a second image layer 1708, a second interior shaded portion 1710 underlies the first interior shaded portion 1706, where the second image layer 1708 represents the estimated background distortion for each fluorescence channel. Values for the estimated distortion generating the second interior shaded portion 1710 are based upon the given combination conjugates according to their: spillover pattern, relative fluorochrome intensities, antigen densities, coexpression matrix, and distortion matrix.

A third image layer 1712 further includes a low limit 1714 representing the low limit of expected fluorescence intensity for each conjugate. All modulated or indiscrete expressions are set to zero as part of the low limit 1714 of expected fluorescence intensity. A fourth image layer 1716 further includes a high limit 1718 representing the high limit of expected fluorescence for each conjugate. Discrete expressions of a particular antigen and dye have equal low limit 1714 and high limit 1718 values for expected fluorescence intensity.

Figure 18A:
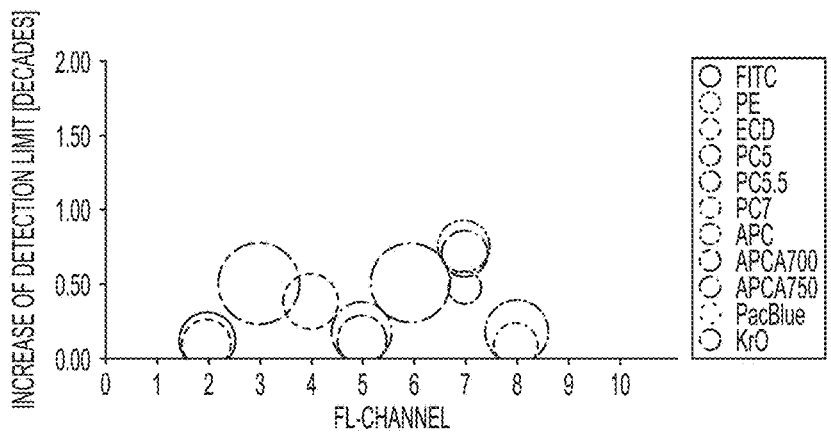
FIGS. 18A-18B depict further aspects of a numerical approach to model spillover patterns including detection radar graphics for multivariate analysis, according to some embodiments.
Figure 18B:
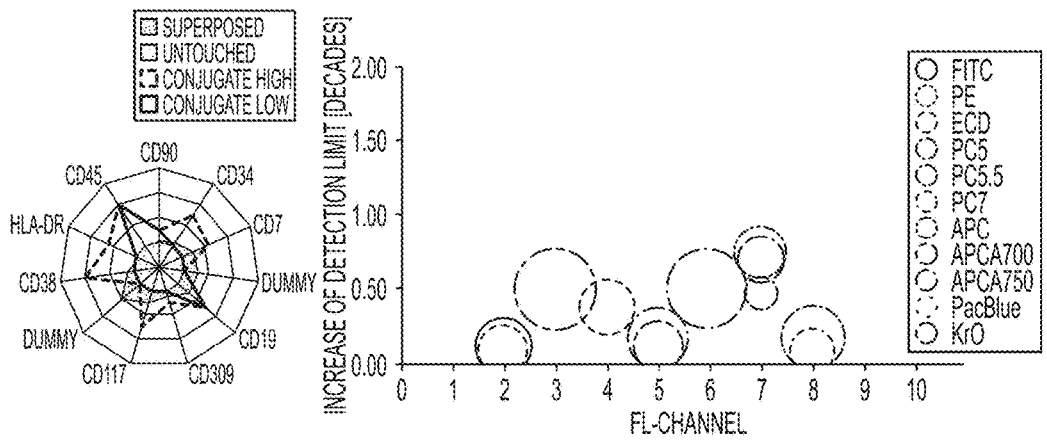

FIGS. 18A and 18B depict aspects of a numerical approach to model spillover patterns, according to some embodiments. As shown here, the evaluation of spillover patterns may involve a detection radar approach and/or a distortion indicator approach. In such distortion indicator representations, each DL can have a color that represents a distorting dye. The Y-axis can represent the amount of distortion, in decades, while the X-axis can represent each distorted FL channel. The diameter of a data point (i.e. the size of a DL) can represent the relative contribution of a single conjugate to the overall distortion.

Figure 19A:
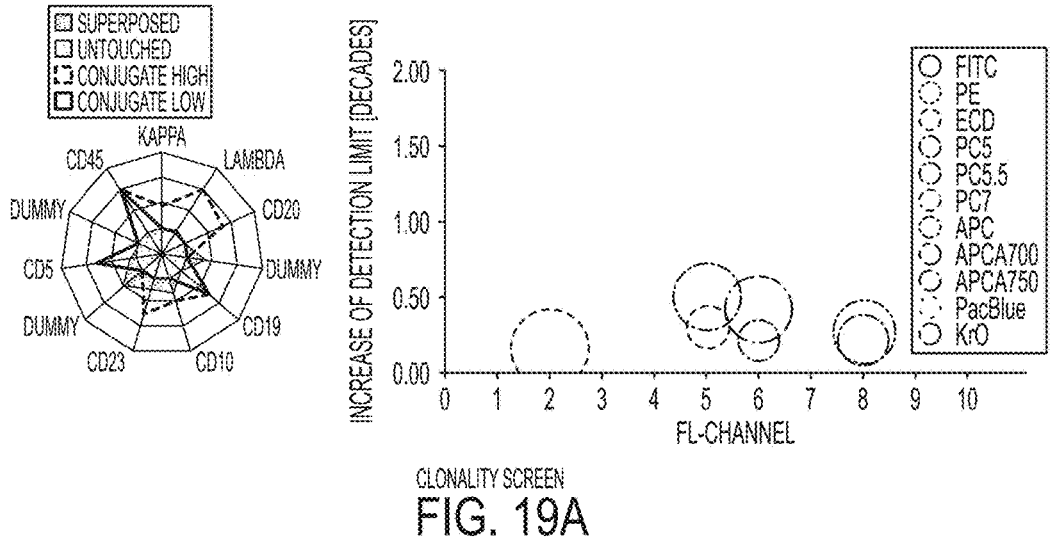
FIGS. 19A-19B depict further aspects of a numerical approach to model spillover patterns including detection radar graphics for multivariate analysis, according to some embodiments.
Figure 19B:
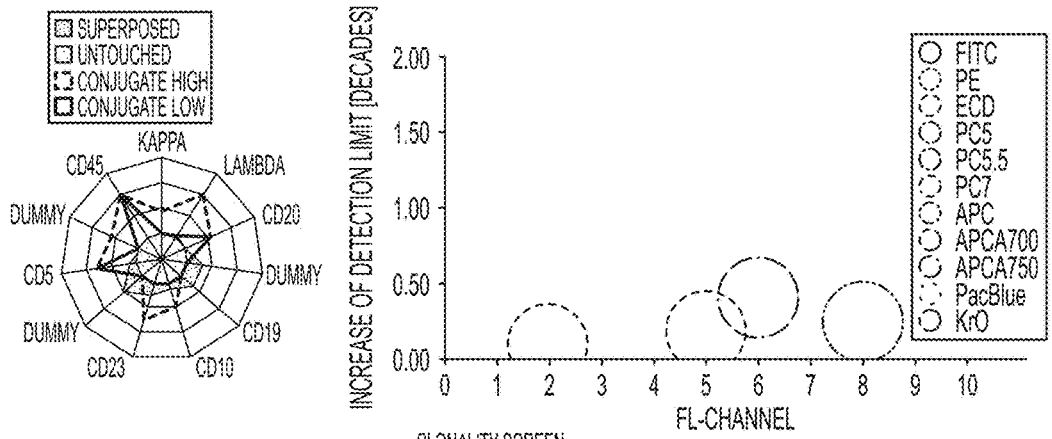

FIGS. 19A and 19B depict aspects of a numerical approach to model spillover patterns, according to some embodiments. As shown here, the evaluation of spillover patterns may involve a clonality screen approach, which can further be represented with a multivariate radar approach.

Upon simulation of a probe panel design as set forth herein, a flow cytometry device can be set up and operated using said probe panel design. In particular, a processor or system, which can be a non-transitory computer-readable media, can receive information regarding a flow cytometer hardware configuration, information regarding a roster comprising a plurality of probes, the individual probes of the roster being associated with respective individual channel-specific detection limits, and information regarding an antigenic coexpression pattern. The processor, or one or more additional, informationally linked processors, can evaluate combinations of individual probes as the probe panel, based on the flow cytometer hardware configuration, the individual channel-specific detection limits, and the antigenic coexpression pattern, the combinations being subsets of probes from the roster, and can further determine the probe panel for use with the flow cytometer hardware configuration, individual channel-specific detection limits, and antigenic coexpression pattern. Finally, a probe panel for use in a flow cytometry procedure can be output, and used by an operator for probe panel design for a flow cytometry instrument and experiment.

Interface and Selection of Parameters for Panel Design and Simulation

Determination of a probe panel can be presented in a web-based interface, allowing for a user to design a probe panel for a flow cytometry experiment using online databases and tools. Particular embodiments of systems and methods (as described above in FIGS. 2-2D) can be provided to an operator as shown in FIGS. 20A-20F. Aspects of the system or method can be provided to an operator as a single form, a transitional form, or as multiple forms representing steps in the method.

Figure 20A:
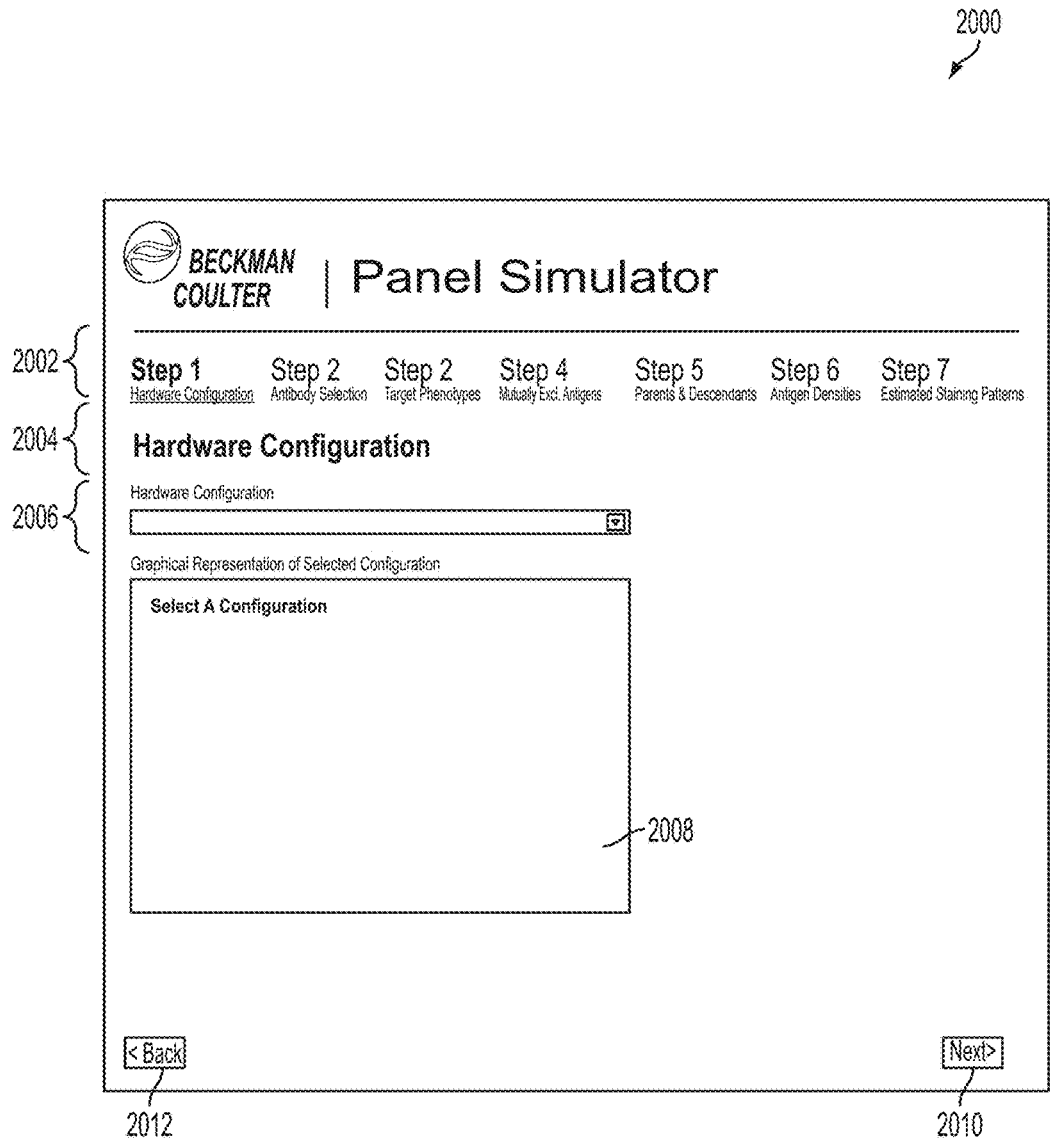
FIGS. 20A-20G depict aspects of a computerized interface for designing and simulating a probe panel, according to some embodiments.

FIG. 20A is an exemplary image of an interface screen that allows for the selection of a hardware configuration 2000 (also referred to as a Hardware Configuration screen 2000). A selection of tabs 2002 allows for the movement between various fields in which data can be entered, which as shown are tabs for steps of a method of simulating a panel. The tab title field 2004 can indicate which step of a method a user is viewing or editing, which in FIG. 20A is "Hardware Configuration", indicated as "Step 1" within the selection of tabs 2002. Drop down field 2006 allows for an operator to select a hardware configuration providing information from a database to establish parameters for performing a panel simulation. The hardware configuration graphical display 2008 can show an operator details of a hardware configuration, including but not limited to, one or more excitation lasers, the wavelengths of excitement of the one or more excitation lasers, voltages or other power values for the one or more excitation lasers, one or more PMT detectors, voltages or other power values for the one or more PMT detectors, or bandpass filters for each of the one or more PMT detectors. In some aspects, the selection of a hardware configuration may be automatically determined by the database and system. The hardware configuration selected can set parameters and values for a panel design and simulation described herein. A selectable "Next >" field 2010 is provided for advancing to a later step in the method. A generally selectable "< Back" field 2012 is provided for advancing to an earlier step in the method, however, in the shown Hardware Configuration screen 2000, there is no earlier step, and thus the "< Back" field 2012 is not selectable on the Hardware Configuration screen 2000.

Figure 20B:
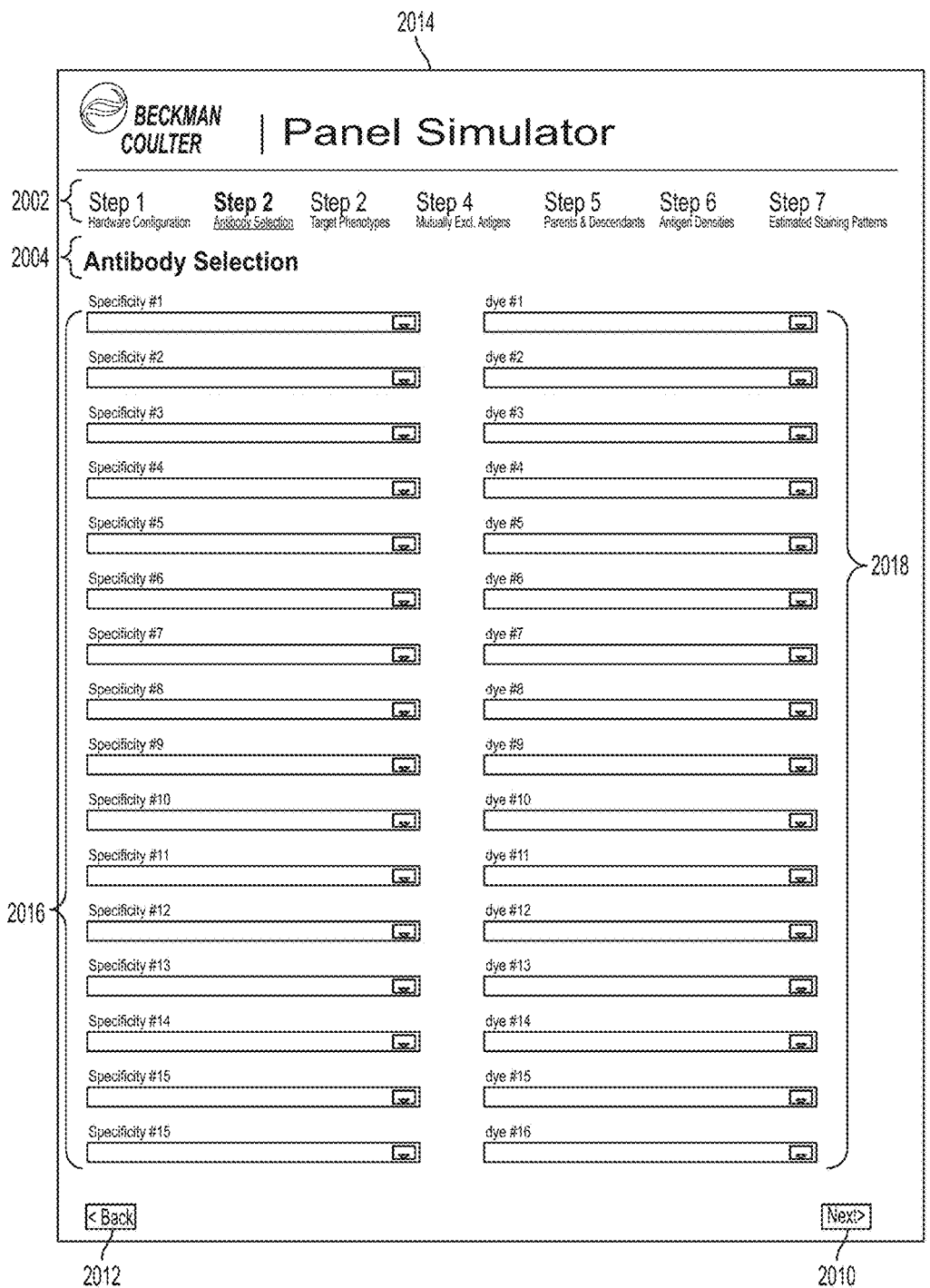

FIG. 20B is an exemplary image of an interface that allows for antibody selection 2014 (also referred to as an Antibody Selection screen 2014). The tab title field 2004 in FIG. 20B is titled "Antibody Selection", and is indicated as "Step 2" within the selection of tabs 2002. A plurality of specificity drop down fields 2016 allows for an operator to select a specificity, and a plurality of dye drop down field 2018 allows for an operator to select a dye. In some embodiments, the specificity to be selected in the specificity drop down fields 2016 can be a selection of antigens or antibodies. For each specificity selected in the specificity drop down fields 2016, a corresponding dye can be selected from the plurality of dye drop down fields 2018. In some aspects, the selection of specificity drop down fields 2016 and dye drop down fields 2018 may be automatically determined by the database and system. The antibodies selected can set parameters and values for a panel design and simulation described herein. A selectable "Next >" field 2010 is provided for advancing to a later step in the method. A selectable "<Back" field 2012 is provided for advancing to an earlier step in the method.

Figure 20C:

FIG. 20C is an exemplary image of an interface that allows for target phenotype selection 2020 (also referred to as an Target Phenotypes screen 2020). The tab title field 2004 in FIG. 20C is titled "Target Phenotypes", and is indicated as "Step 3" within the selection of tabs 2002. A target population drop down field 2022 allows for an operator to select a target population relating to specific antigens that do or should express a target phenotype. A plurality of "Unrelated Antigens" 2024 is provided, listing a selection of antibody and dye conjugates that are not, or may not be, related to a selected target population. Each antibody and dye pair in the plurality of Unrelated Antigens 2024 includes a selectable check-box to indicate that the antibody and dye pair is an antigen of interest. A plurality of "Antigens of Interest" 2026 is provided, listing a selection of antibody and dye conjugates that are, or are believed to be, related to a selected target population. The members of the plurality of Antigens of Interest 2026 can be populated by antibody and dye pairs originally provided in the plurality of Unrelated Antigens 2024, or may be autopopulated according to relationships data stored in the database and system. The indication that a particular antibody and dye pair is a member of the plurality of Antigens of Interest 2026 can be removed by deselecting a selectable check box for the antibody and dye pair. In some aspects, the selection of the plurality of Unrelated Antigens 2024 and the plurality of Antigens of Interest 2026 may be automatically determined by the database and system. In some aspects, an Antigen of Interest global selection field 2028 can be provided, having an activatable field to select all antibody and dye pairs as members of the plurality of Antigens of Interest 2026 and an activatable field to indicated all antibody and dye pairs as members of the plurality of Unrelated Antigens 2024. The target phenotypes, unrelated antigens, and antigens of interest selected can set parameters and values for a panel design and simulation described herein. Although not expressly shown in FIG. 20C, A selectable "Next >" field is provided for advancing to a later step in the method and a selectable "< Back" field is provided for advancing to an earlier step in the method.

Figure 20D:
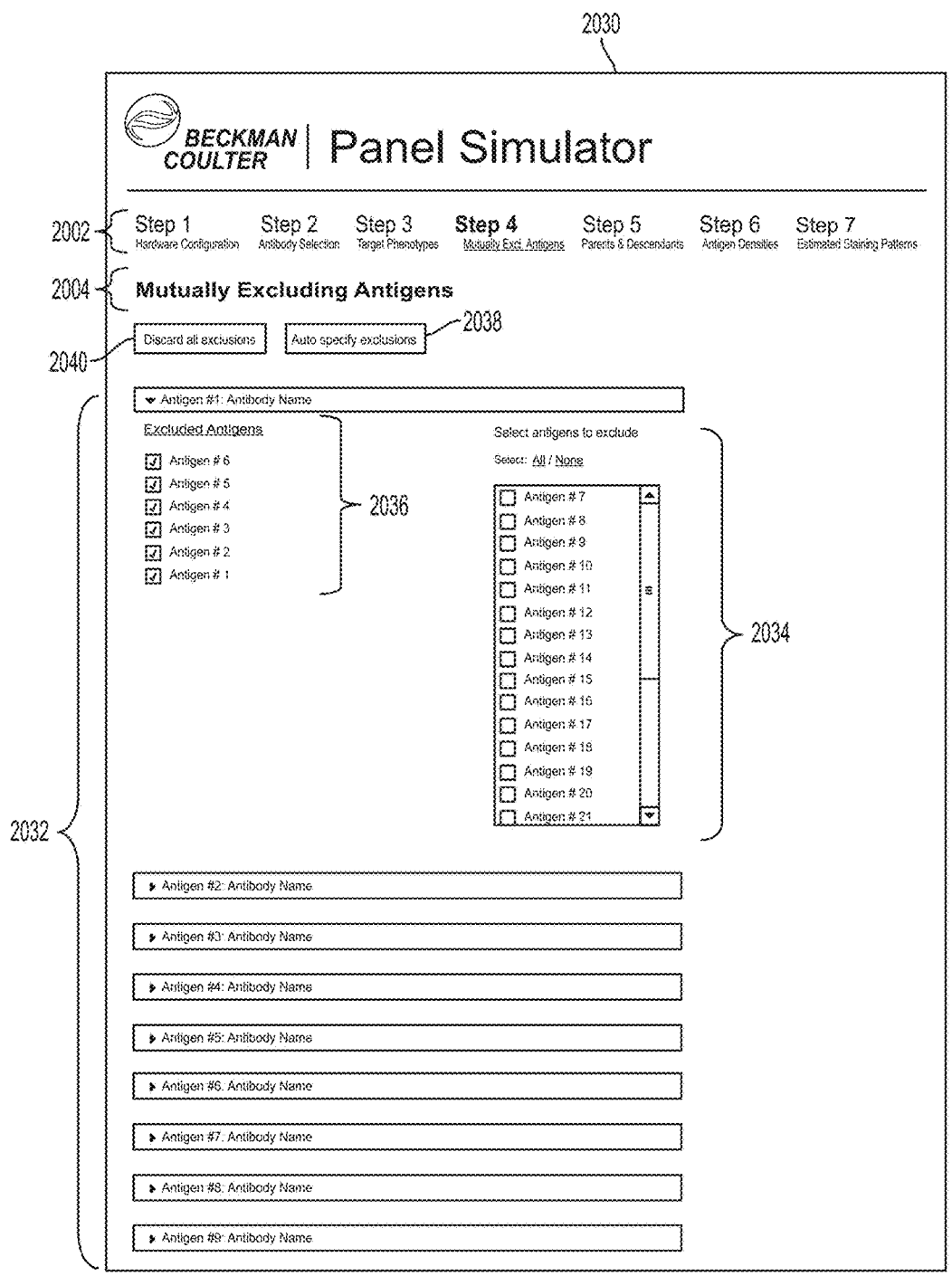

FIG. 20D is an exemplary image of an interface that allows for identification of mutually excluding antigens 2030 (also referred to as Mutually Excluding Antigen screen 2030). The tab title field 2004 in FIG. 20D is titled "Mutually Excluding Antigens", and is indicated as "Step 4" within the selection of tabs 2002. A selection of expandable antigen-antibody paring fields 2032 are provided, where when expanded, antigen-antibody paring field provides a listing of antigens to exclude 2034; this can be a list of potential antigens that may be mutually excluding with the antigen-antibody paring for an individual field. The listing of antigens to exclude 2034 can have a check-box by each listed antigen to select a particular antigen to indicate as excluded, which is an indication that the selected antigen or antigens does not coexpress with the antigen identified as the part of the antigen-antibody paring for that field. The listing of antigens to exclude 2034 can further include one or more selection links that can cause all antigens in the listing 2034 to be selected, or to de-select all antigens in the listing 2034. Antigens that are indicated as excluded can be listed in an identified excluded antigens list 2036. The listing of identified excluded antigens 2036 can have a selected check-box by each listed antigen, which can be de-selected to indicate that the particular antigen is not mutually excluded for a given antigen-antibody paring field. In aspects, the listing of antigens to exclude 2034 can be selected by an operator selecting one or more listed antigens based on an operator-generated rationale. In other aspects, the listing of identified excluded antigens 2036 can be specified by the database and system; a selectable "Auto Specify Exclusions" field 2038 is provided to allow an operator to indicate mutually excluded antigens according to data stored in the database and system. Conversely, a selectable "Discard All Exclusions" field 2040 is provided to allow an operator to de-select all previously indicated mutual exclusions for one or more antibody-antigen paring fields. The mutually excluding antigens selected can set parameters and values for a panel design and simulation described herein. Although not expressly shown in FIG. 20D, A selectable "Next >" field is provided for advancing to a later step in the method and a selectable "< Back" field is provided for advancing to an earlier step in the method.

Figure 20E:
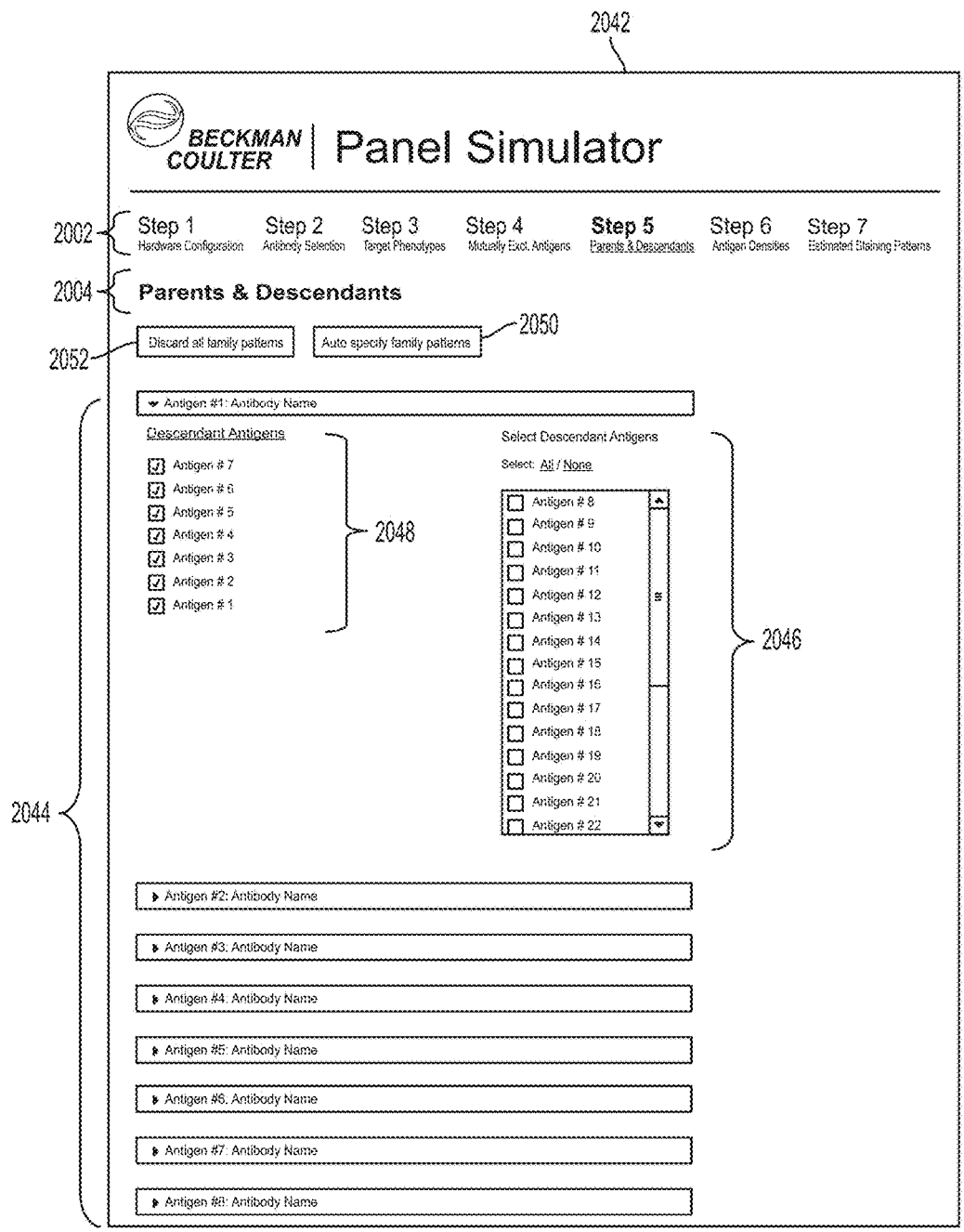

FIG. 20E is an exemplary image of an interface that allows for identification of parent and descendant antigens 2042 (also referred to as Parent & Descendent Antigens screen 2042). The tab title field 2004 in FIG. 20E is titled "Parents & Descendants", and is indicated as "Step 5" within the selection of tabs 2002. A selection of expandable antigen-antibody paring fields 2044 are provided, where when expanded, antigen-antibody paring field provides a listing of descendant antigens 2046; this can be a list of descendant antigens, being descendants a parent antigen indicated as the antigen of the antigen-antibody paring for an individual field. The listing of descendant antigens 2046 can have a check-box by each listed antigen to select a particular antigen to indicate as a descendant, which is an indication that the selected antigen or antigens is a cluster of differentiation later in a developmental progression or step than the cluster of differentiation indicated as the selected antigen of the antigen-antibody paring for that field. The listing of descendant antigens 2046 can further include one or more selection links that can cause all antigens in the listing 2046 to be selected, or to de-select all antigens in the listing 2046. Antigens that are indicated as descendants can be listed in an identified descendant antigens list 2048. The listing of identified descendant antigens list 2048 can have a selected check-box by each listed antigen, which can be de-selected to indicate that the particular antigen is not a descendant for a given antigen-antibody paring field. In aspects, the listing of descendant antigens 2046 can be selected by an operator selecting one or more listed antigens based on an operator-generated rationale. In other aspects, the listing of descendant antigens 2046 can be specified by the database and system; a selectable "Auto Specify Family Patterns" field 2050 is provided to allow an operator to indicate parent and descendant antigen relationships according to data stored in the database and system. Conversely, a selectable "Discard All Family Patterns" field 2052 is provided to allow an operator to de-select all previously indicated parent and descendant antigen relationships for one or more antibody-antigen paring fields. The parent and descendant antigen relationships selected can set parameters and values for a panel design and simulation described herein. Although not expressly shown in FIG. 20E, A selectable "Next >" field is provided for advancing to a later step in the method and a selectable "< Back" field is provided for advancing to an earlier step in the method.

Figure 20F:
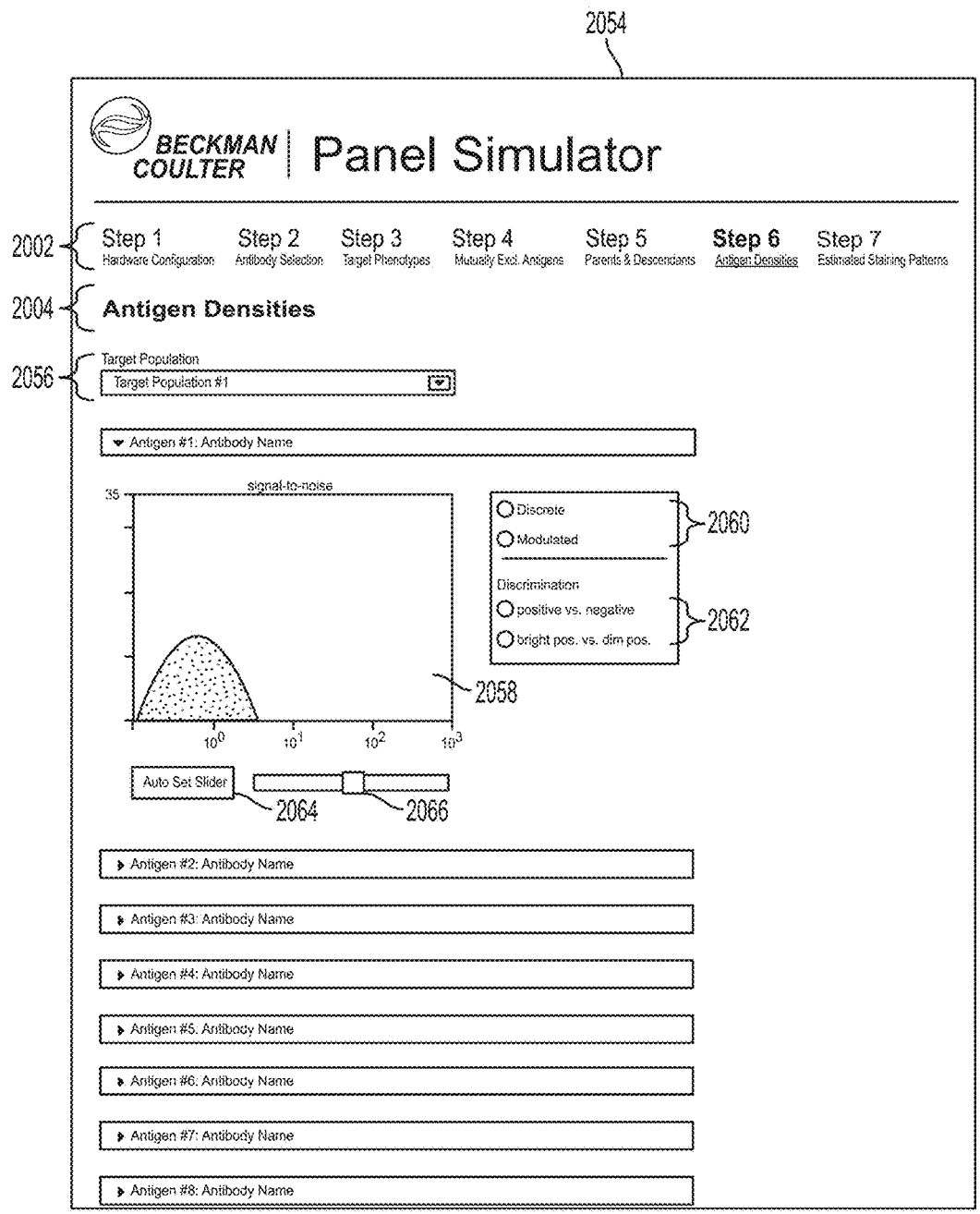

FIG. 20F is an exemplary image of an interface that allows for identification of and antigen densities 2052 (also referred to as Antigen Density screen 2052). The tab title field 2004 in FIG. 20F is titled "Antigen Densities", and is indicated as "Step 6" within the selection of tabs 2002. A target population drop down field 2056 allows for an operator to select a target population relating to specific antigens, and particularly the density of the specific antigen for a particular cell type or target population. The density of antigens in a region of a cell, or for a type of cell or target population, corresponds to the strength of expression of that antigen, and how it can interact or be measured with populations of other antigens. A signal-to-noise display 2058 can indicate across decades of expression the ratio of signal expected from a target population and corresponding antigen over background noise. A discrete/modulated selection field 2060 can be provided, which in aspects can be a radio button selection field, to configure the signal-to-noise display 2058 to display the expression of the target population when evaluated according to discrete or modulated parameters, as described above. Similarly, discrimination selection field 2062 can be provided, which in aspects can be a radio button selection field, to configure the signal-to-noise display 2058 to discriminate the results of the target population as either between positive and negative expression or as between bright positive and dim positive expression, as described above. A slider setting can be set for the signal-to-noise display 2058, to adjust the scale and scope of the region of the signal-to-noise display 2058 displayed. In some aspects, the slider setting can be chosen with a selectable "Auto Set Slider" field 2064, using the data of the antigen and target population display to automatically set the range of the signal-to-noise display 2058. In other aspects, an operator can direct the signal-to-noise display 2058 to have a specific scale by manually adjusting a slider interface 2066, which can be a radio slider interface. The target populations, discrete versus modulated display selection, discrimination selection, slider setting, and antigen densities selected can set parameters and values for a panel design and simulation described herein. Although not expressly shown in FIG. 20F, A selectable "Next >" field is provided for advancing to a later step in the method and a selectable "< Back" field is provided for advancing to an earlier step in the method.

Figure 20G:
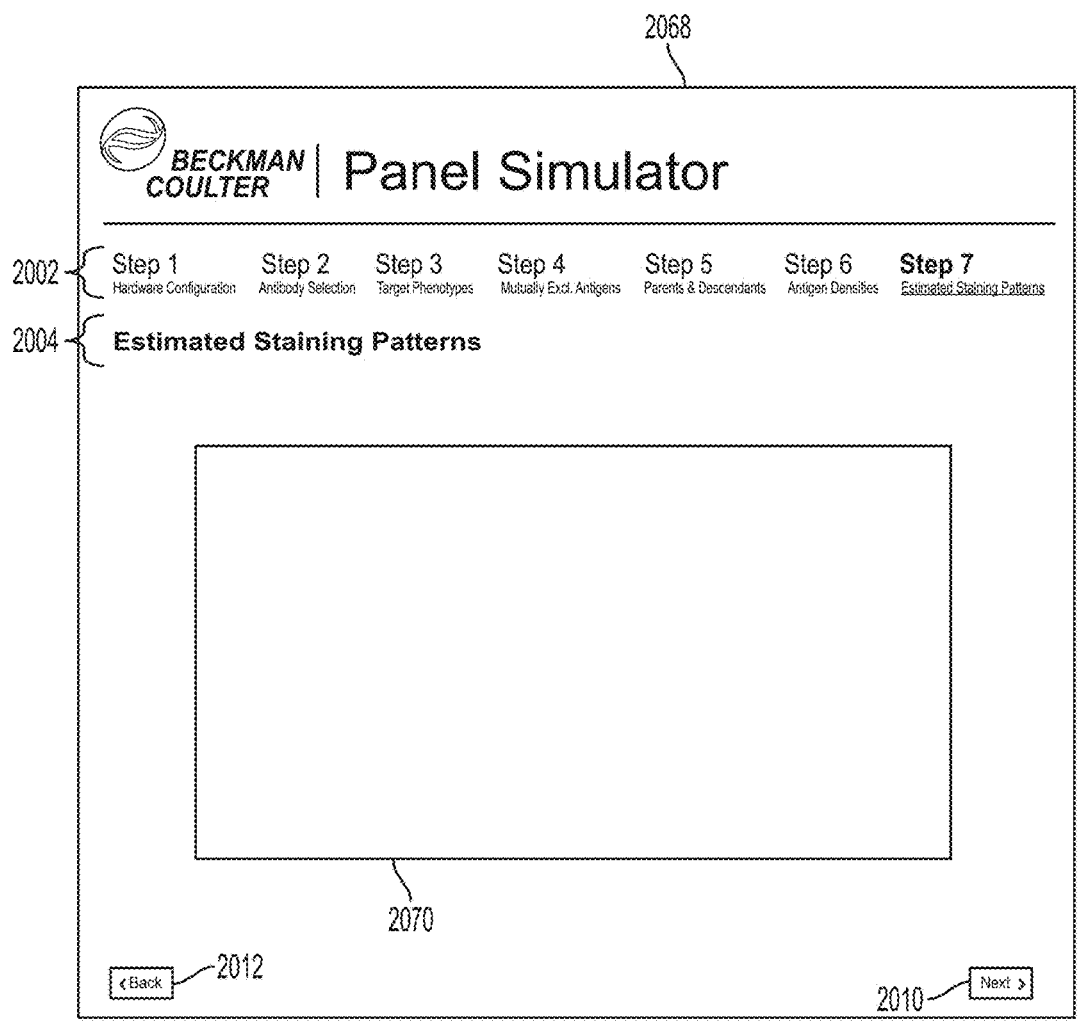

FIG. 20G is an exemplary image of an interface that displays a panel expression simulation estimate for a given antigen panel design 2068 (also referred to as Panel Simulation screen 2068). Information taken from the input into the Hardware Configuration screen 2000, Antibody Selection screen 2014, Target Phenotypes screen 2020, Mutually Excluding Antigen screen 2030, Parent & Descendent Antigens screen 2042, and Antigen Density screen 2052 can be collected and used to calculate an expected expression or staining pattern. The tab title field 2004 in FIG. 20G is titled "estimated Staining Patterns", and is indicated as "Step 7" within the selection of tabs 2002. A display field 2070 can provide either or both of numerical and graphical representations of estimated antigen expression for a given panel design, including but not limited to graphical representations discussed herein. The generally selectable "Next >" field 2010 shown is not selectable on the Panel Simulation screen 2068 because there is no later step in the corresponding method or evaluation to advance to. The selectable "< Back" field 2012 is provided for advancing to an earlier step in the method.

Figure 21A:
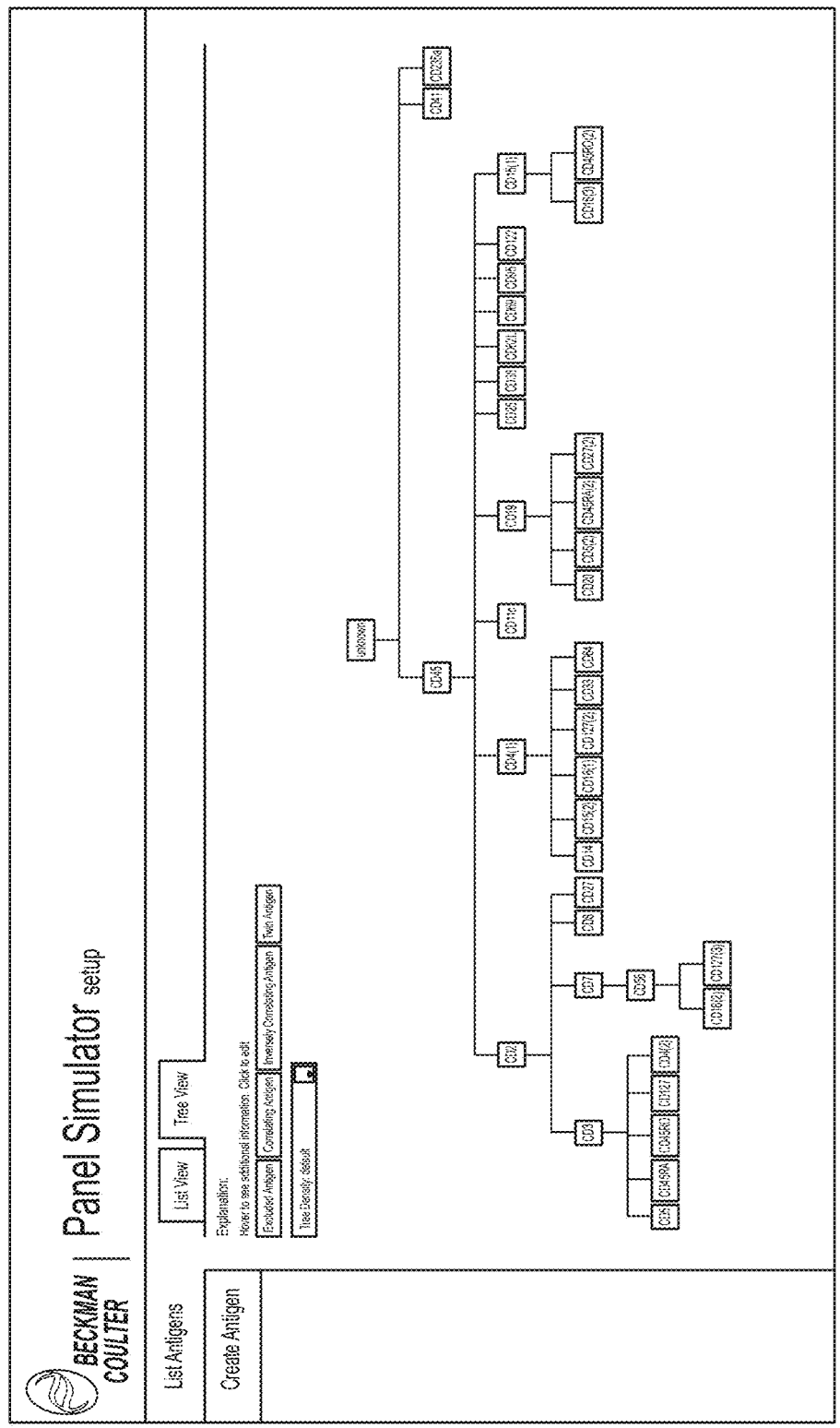
Figure 21B:
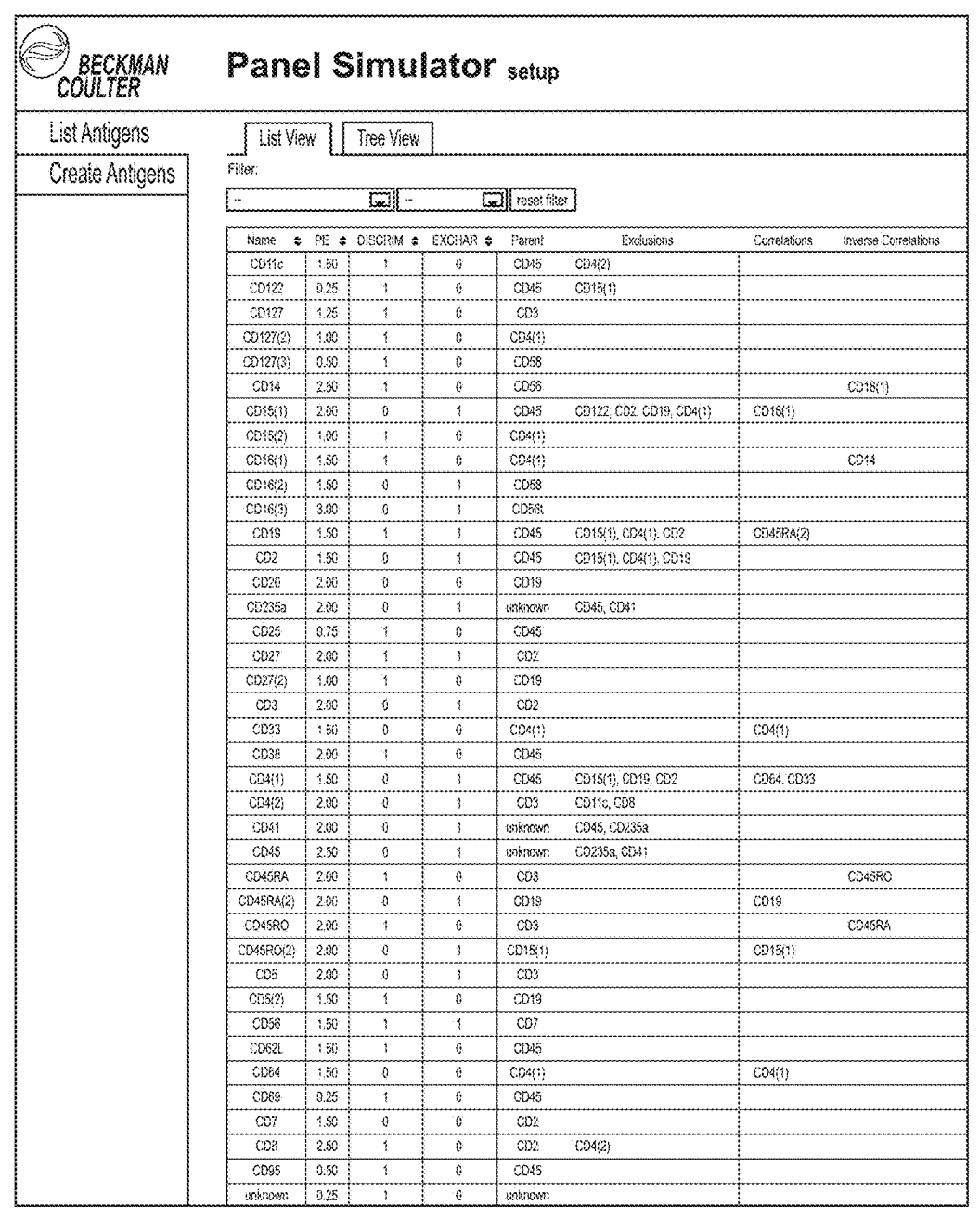

In some embodiments, a web-based interface can present information to an operator to further detail the relationships between various antigens for a cell phenotype. FIG. 21A is an exemplary developmental tree (similar in form to a geological tree) illustrating relationships between CD members (i.e. antigens) for a cell phenotype. Such a developmental tree can illustrate the parent-child relationships between antigens, and thereby further illustrate sibling relationships, cousin relationships, and aunt relationships between antigens. In some aspects, antigens can be identified as developing along more than one developmental path, and can be identified as a "twin antigen" along with occurrences of the same antigen on the developmental tree. In further embodiments, the selection or transient highlighting (e.g. hovering over a field defined by software to represent a CD member or antigen) of a particular antigen field can be used as a stimulus to further display expression relationships with other antigens on the developmental tree. For example, the selection or transient highlighting of an antigen field can indicate, for the indicated antigen, which other antigens on the developmental tree are mutually excluded from expression with the selected antigen, which other antigens on the developmental tree have correlating expression with the selected antigen, which other antigens on the developmental tree have inversely correlated expression with the selected antigen, which other antigens on the developmental tree are twins to the selected antigen, or which other antigens on the developmental tree otherwise coexpress with the selected antigen. In other aspects, the developmental relationship between antigens can be provided in a listing or tabular form, as illustrated in FIG. 21B, as an exemplary embodiment.

Multicolor Compensation with Measured Panel

Figure 22A:
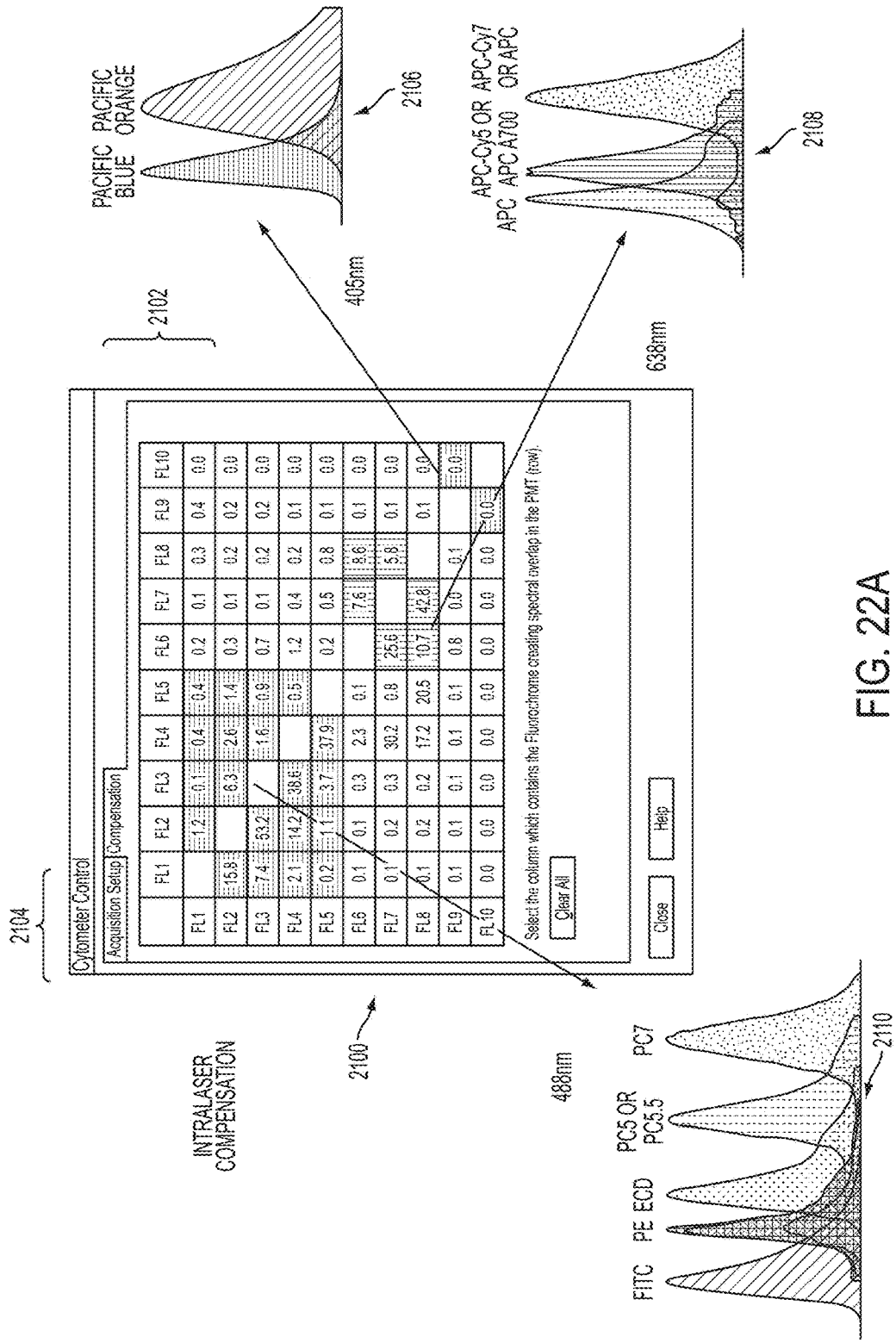
FIGS. 22A-22B depict aspects, according to some embodiments.
Figure 22B:
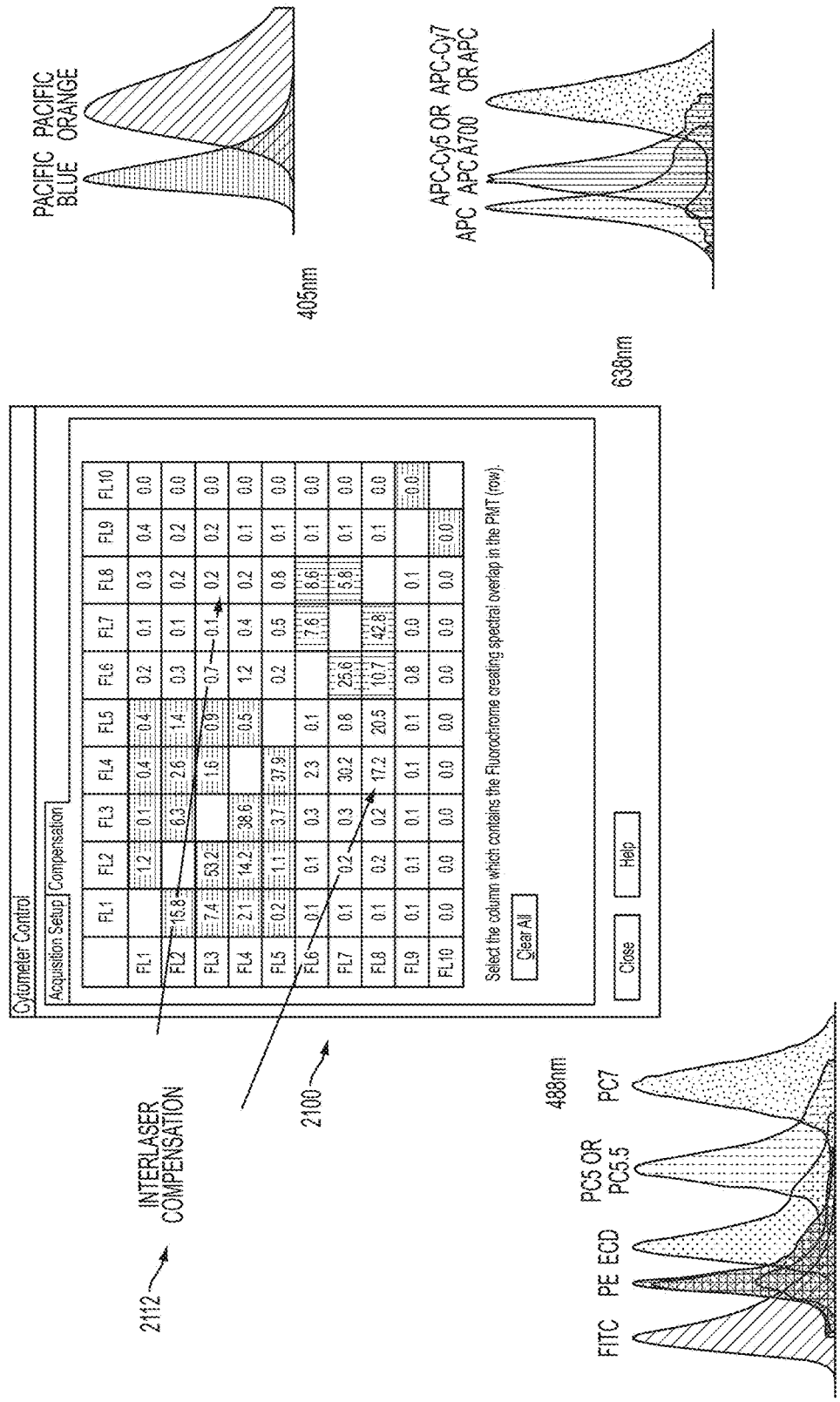

As noted above, the methodology to predict and simulate panel expression can also be applied to derive or extrapolate the magnitudes and sources of signal from measured panel and antigens in a sample. Distortion and coexpression matrices can be calculated and used to compensate for mutual coexpression or patent-descendant spillover, which in aspects may be enforced by setting appropriate gating parameters. In some aspects, the lasers used to excite dyes coupled to antibodies may excite more than an intended dye target, and compensation tables or matrices can be used to accommodate and correct for such spillover. FIG. 22A depicts aspects of intralaser compensation according to some embodiments. Similarly, FIG. 22B depicts aspects of interlaser compensation according to embodiments. Both FIG. 22A and FIG. 22B depict the same compensation table 2200, which sets forth a configuration of fluorochromes in the columns 2202 and a set of PMT in the rows 2204. The compensation table 2200 is determined by the individual identities of the fluorochromes in the columns 2212 and the PMT in the rows 2204, which is specific to each hardware configuration and panel design chosen. FIG. 22A focuses on the intralaser compensation values, values for which spillover from one fluorochrome triggered by a given excitation laser wavelength can affect a PMT for a separate fluorochrome also triggered by the same excitation laser wavelength. In contrast, FIG. 22B focuses on the interlaser compensation values, values for which spillover from one fluorochrome triggered by a given excitation laser wavelength can affect a PMT for a separate fluorochrome triggered by a different excitation laser wavelength.

As illustrated in FIG. 22A, fluorochromes triggered by excitation light having a wavelength ($\lambda$) of 405 nm are located in the FL9 and FL10 columns, with corresponding detection channels in the FL9 and FL10 rows. As shown, the FL9 and FL10 detection are for Pacific Blue and Pacific Orange fluorochromes, respectively. The 405 nm comparison plot 2206 reflects the region of overlap each fluorochrome, and is represented in the compensation table 2200 by the intersection region of FL9 and FL10 columns and rows. The intersection region of FL9 and FL10 columns and rows is populated with values or factors used to correct for distortion, as discussed above. Similarly, fluorochromes triggered by excitation light having a wavelength ($\lambda$) of 638 nm are located in the FL6. FL7, and FL8 columns, with corresponding detection channels in the FL6, FL7, and FL8 rows. As shown, the FL6, FL7, and FL8 detection are for APC, APC-Cy5 or APC-A700, and APC-Cy7 or APC-A750 fluorochromes, respectively. The 638 nm comparison plot 2208 reflects the region of overlap each fluorochrome, and is represented in the compensation table 2200 by the intersection region of FL6, FL7, and FL8 columns and rows. The intersection region of FL6, FL7, and FL8 columns and rows is populated with values or factors used to correct for distortion, as discussed above. Further, fluorochromes triggered by excitation light having a wavelength ($\lambda$) of 488 nm are located in the FL1, FL2, FL3, FL4, and FL5 columns, with corresponding detection channels in the FL1, FL2, FL3, FL4, and FL5 rows. As shown, the FL1, FL2, FL3, FL4, and FL5 detection are for FITC, PE, ECD, PC5 or PC5.5, and PC7 fluorochromes, respectively. The 488 nm comparison plot 2210 reflects the region of overlap each fluorochrome, and is represented in the compensation table 2200 by the intersection region of FL1, FL2, FL3, FL4, and FL5 columns and rows. The intersection region of FL1, FL2. FL3, FL4, and FL5 columns and rows is populated with values or factors used to correct for distortion, as discussed above.

As one would expect, the intersection between a given fluorochrome and the channel that is configured to detect that fluorochrome does not require any compensation value or factor, and is indicated on the compensation table 2200 as the diagonal without any numerical values populating the cells of the compensation table 2200.

As illustrated in FIG. 22B, fluorochromes can also be triggered by excitation light at a wavelength not configured or intended to excite the fluorochrome. The interlaser compensation region 2212 can include the two sections of the compensation table 2200 outside of the intralaser compensation regions. The two sections of interlaser compensation region 2212 indicate compensation values or factors for: fluorochromes FL1-FL5, affecting the detection channels for FL6-FL8 and FL9-FL10; fluorochromes FL6-FL8, affecting the detection channels for FL1-FL5 and FL9-FL10; and fluorochromes FL9-FL10, affecting the detection channels for FL1-FL5 and FL6-FL8. The two sections of interlaser compensation region 2212 is populated with values or factors used to correct for distortion, as discussed above.

Figure 23:
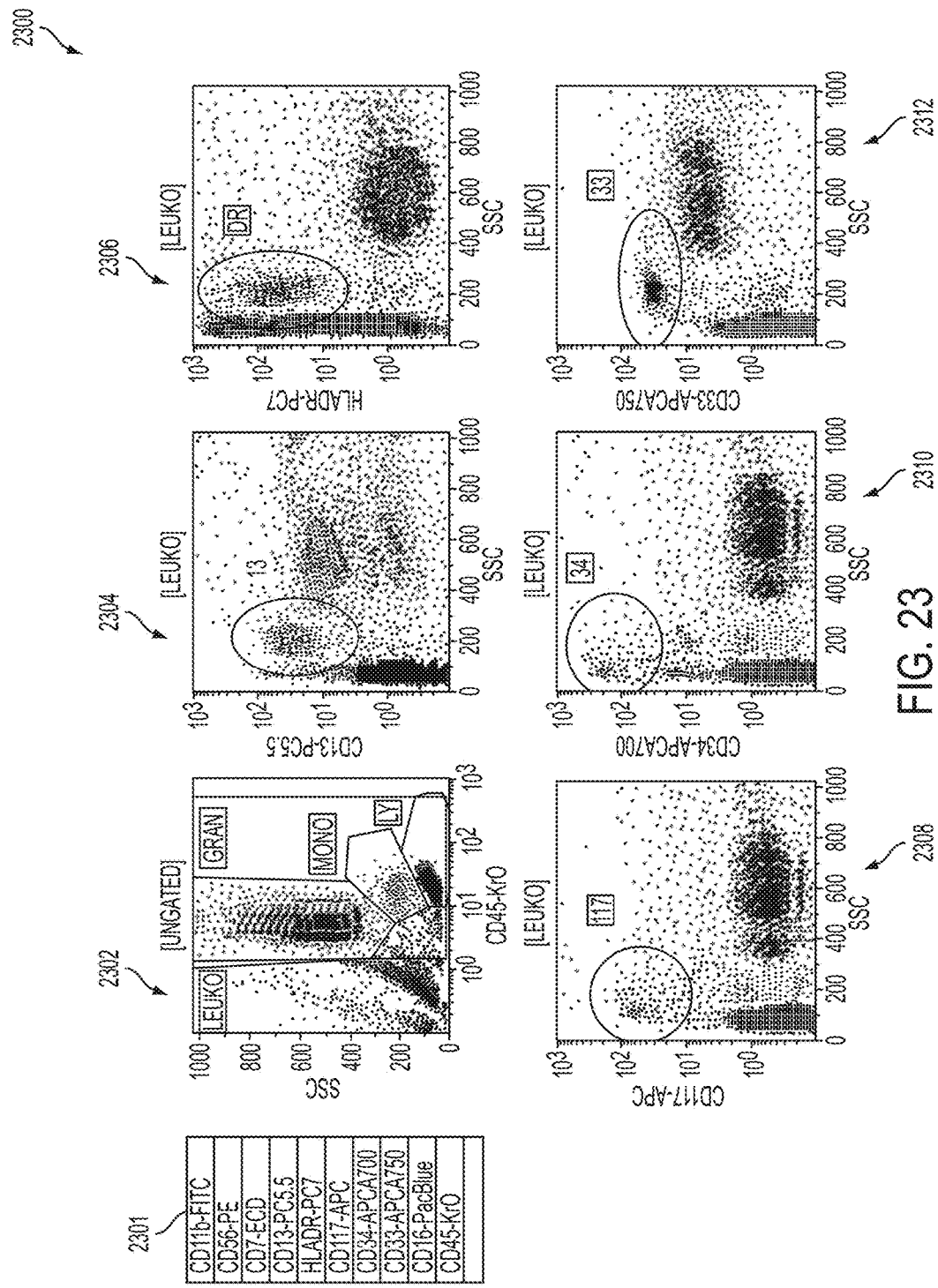
FIGS. 23-26 depict aspects of a computerized interface for designing and simulating a probe panel, according to some embodiments.

FIG. 23 depicts an approach to determining a distortion calculation according to some embodiments. In particular, FIG. 23 displays six result plots of fluorochrome expression measured using ten (10) dyes for a [LEUKO] cell phenotype. The table 2301 provides a listing of antibody-dye conjugates that can be detected and used to develop gating parameters and related plots, where FIG. 23 provides an exemplary selection of plots and gating techniques based on the listing of antibody-dye conjugates in table 2301. The plot 2302 displays the signal from a CD45-KrO antibody-dye conjugate against the general side scattered light (SSC) measured from a flow cytometry system. In the plot 2302, the expression signal in the first decade is identified as [LEUKO], relating to that phenotype. The remaining five plots are detail extrapolations, applying gating techniques, of signal in the first decade of [LEUKO] signal. The plot 2304 displays the SSC signal against CD13-PC5.5 (the signal of CD13 measured in the PMT for PC5.5) and identifies the expression region and density for CD13 therein. The plot 2306 displays the SSC signal against HLADR-PC7 (the signal of HLADR measured in the PMT for PC7) and identifies the expression region and density for HLADR therein. The plot 2308 displays the SSC signal against CD117-APC (the signal of CD117 measured in the PMT for APC) and identifies the expression region and density for CD117 therein. The plot 2310 displays the SSC signal against CD34-APCA700 (the signal of CD34 measured in the PMT for APCA700) and identifies the expression region and density for CD34 therein. The plot 2312 displays the SSC signal against CD33-APCA750 (the signal of CD33 measured in the PMT for APCA750) and identifies the expression region and density for CD33 therein. As evident from the six plots of FIG. 23, the result profile can appear different for any given antibody-dye conjugate measured for, and the density of any given antibody-dye conjugate can be isolated from signal for other antibody-dye conjugate combinations present in the cell or phenotype.

Figure 24:
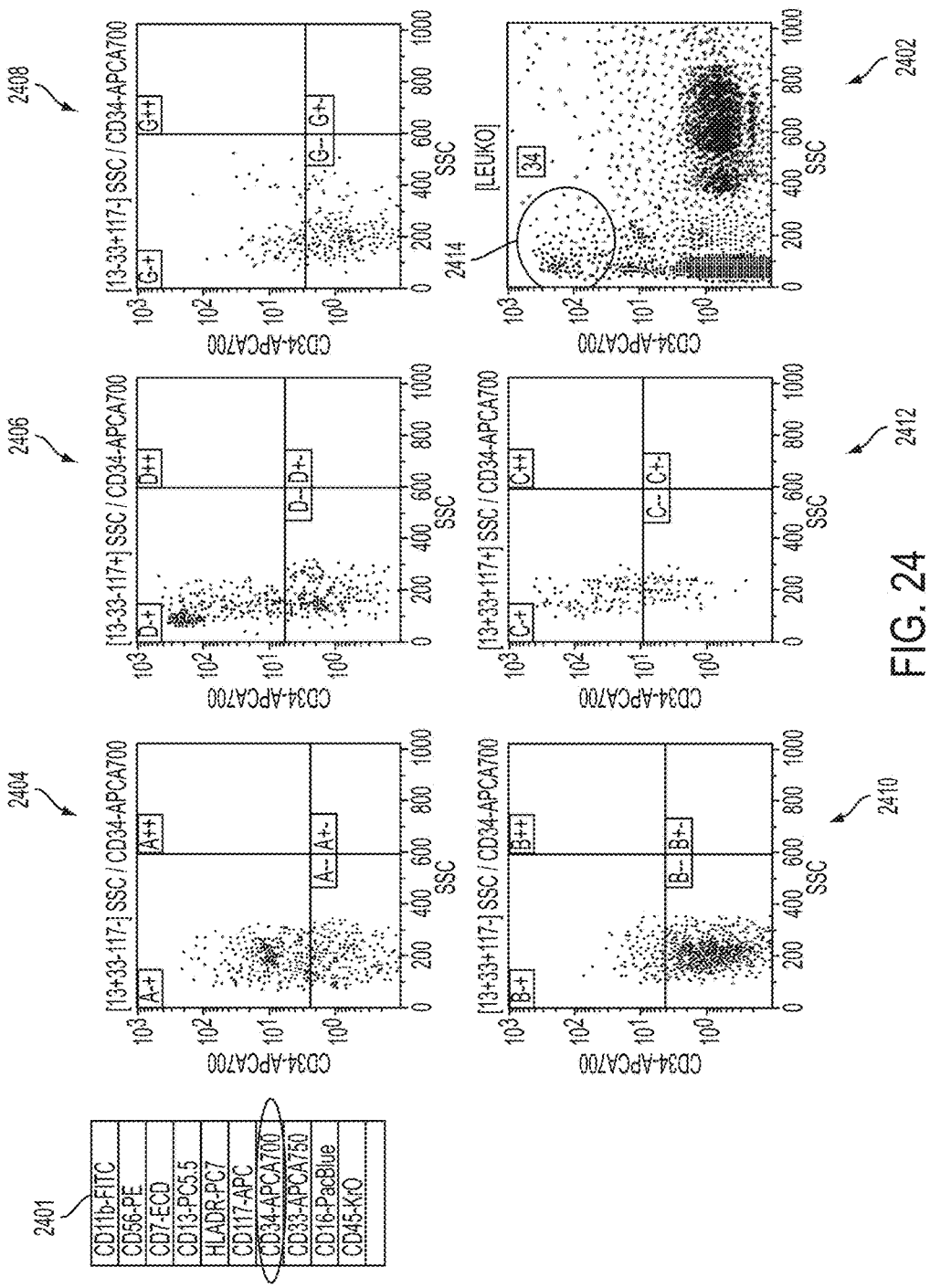

FIG. 24 depicts an approach to determining a distortion calculation according to some embodiments. In particular, FIG. 24 displays six result plots of fluorochrome expression measured using ten (10) dyes for a [LEUKO] cell phenotype, indicating quadrants for predicted detection levels for different gating parameters. The table 2401 provides a listing of antibody-dye conjugates that can be detected and used to develop gating parameters and related plots, where FIG. 24 provides an exemplary selection of plots and gating techniques based on the listing of antibody-dye conjugates in table 2401 The first plot 2402 displays the overall SSC signal against signal measured from a CD34-APCA700 antibody-dye conjugates for a [LEUKO] cell phenotype. The signal indicating the population of CD34 positive events is identified as the region 2414. The remaining five plots reflect application of gating techniques to identify positivity or negativity of signal in comparison to signal measured by the system from other fluorochrome conjugates. The plot 2404 displays the signal measured from CD34-APCA700 with gating parameters applied to further indicate positive signal measured from CD13 antigens, while remaining negative for CD33 and CD117 antigens. The plot 2406 displays the signal measured from CD34-APCA700 with gating parameters applied to further indicate positive signal measured from CD17 antigens, while remaining negative for CD13 and CD33 antigens. The plot 2408 displays the signal measured from CD34-APCA700 with gating parameters applied to further indicate positive signal measured from CD33 antigens, while remaining negative for CD13 and CD117 antigens. The plot 2410 displays the signal measured from CD34-APCA700 with gating parameters applied to further indicate positive signal measured from CD13 and CD 33 antigens, while remaining negative for CD117 antigens. The plot 2412 displays the signal measured from CD34-APCA700 with gating parameters applied to further indicate positive signal measured from CD13, CD33 and CD117 antigens.

Figure 25:
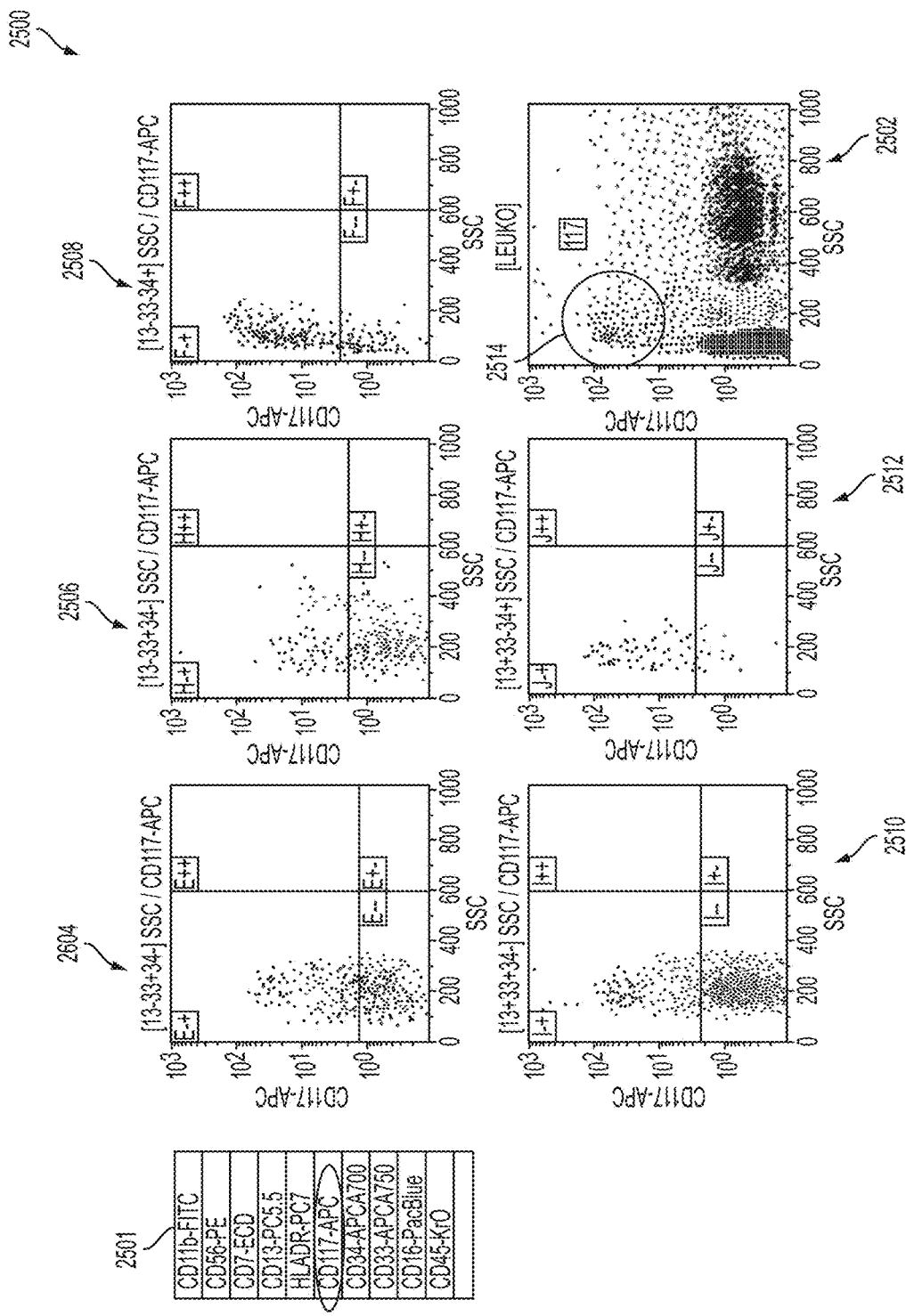

FIG. 25 depicts an approach to determining a distortion calculation according to some embodiments. In particular, FIG. 25 displays six result plots of fluorochrome expression measured using ten (10) dyes for a [LEUKO] cell phenotype, indicating quadrants for predicted detection levels for different gating parameters. The table 2501 provides a listing of antibody-dye conjugates that can be detected and used to develop gating parameters and related plots, where FIG. 25 provides an exemplary selection of plots and gating techniques based on the listing of antibody-dye conjugates in table 2501. The plot 2502 displays the overall SSC signal against signal measured from a CD117-APC antibody-dye conjugate for a [LEUKO] cell phenotype. The signal indicating the population of CD117 positive events is identified as the region 2514. The remaining five plots reflect application of gating techniques to identify positivity or negativity of signal in comparison to signal measured by the system from other fluorochrome conjugates. The plot 2504 displays the signal measured from CD117-APC with gating parameters applied to further indicate positive signal measured from CD13 antigens, while remaining negative for CD33 and CD34 antigens. The plot 2506 displays the signal measured from CD117-APC with gating parameters applied to further indicate positive signal measured from CD33 antigens, while remaining negative for CD13 and CD34 antigens. The plot 2508 displays the signal measured from CD117-APC with gating parameters applied to further indicate positive signal measured from CD34 antigens, while remaining negative for CD13 and CD33 antigens. The plot 2510 displays the signal measured from CD117-APC with gating parameters applied to further indicate positive signal measured from CD13 and CD 33 antigens, while remaining negative for CD34 antigens. The plot 2512 displays the signal measured from CD117-APC with gating parameters applied to further indicate positive signal measured from CD13, CD33 and CD43 antigens.

Figure 26:
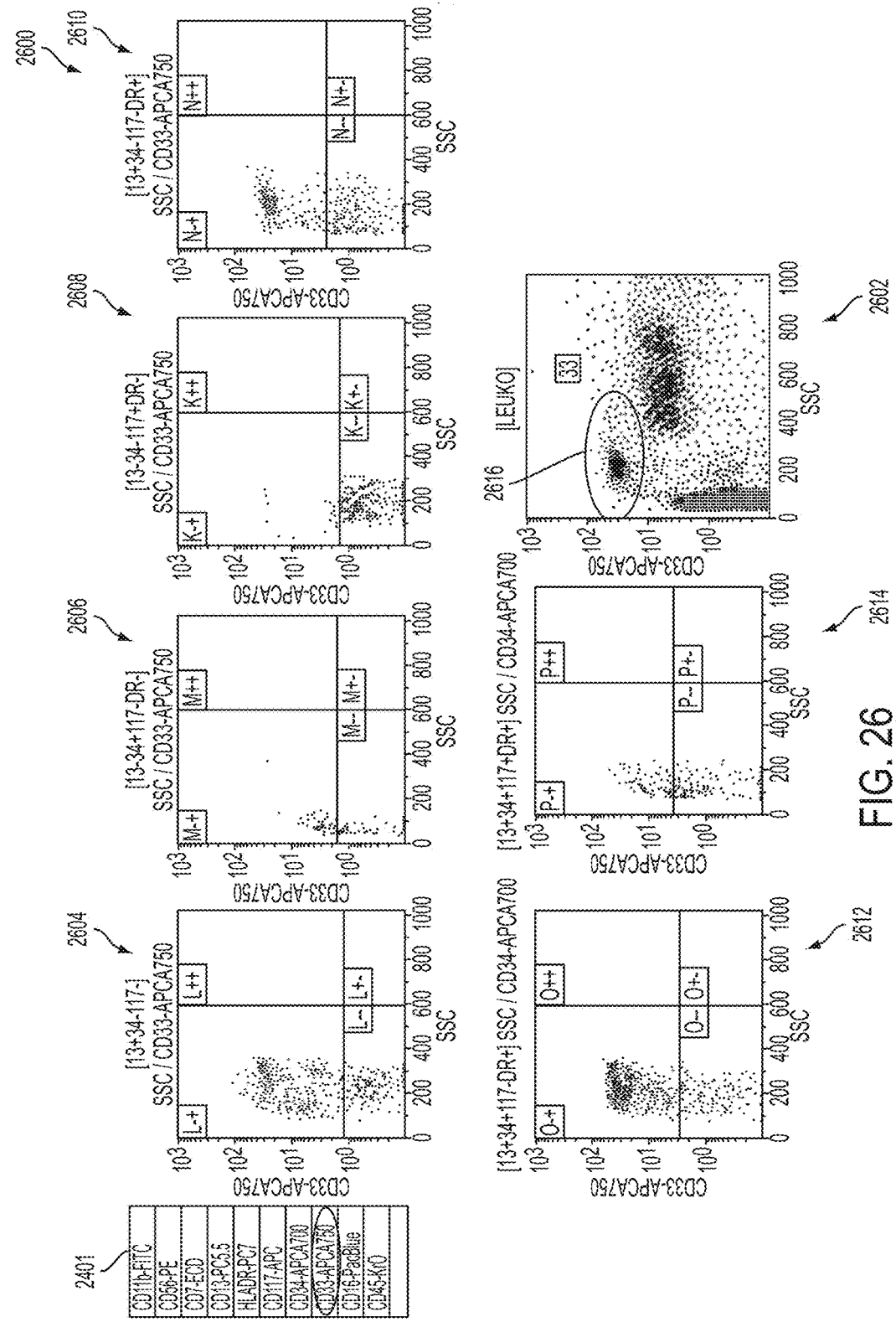

FIG. 26 depicts an approach to determining a distortion calculation according to some embodiments. In particular, FIG. 26 displays seven result plots of fluorochrome expression measured using ten (10) dyes for a [LEUKO] cell phenotype, indicating quadrants for predicted detection levels for different gating parameters. The table 2601 provides a listing of antibody-dye conjugates that can be detected and used to develop gating parameters and related plots, where FIG. 26 provides an exemplary selection of plots and gating techniques based on the listing of antibody-dye conjugates in table 2601. The plot 2602 displays the overall SSC signal against signal measured from a CD33-APCA750 antibody-dye conjugate for a [LEUKO] cell phenotype. The signal indicating the population of CD33 positive events is identified as the region 2616. The remaining six plots reflect application of gating techniques to identify positivity or negativity of signal in comparison to signal measured by the system from other fluorochrome conjugates. The plot 2604 displays the signal measured from CD33-APCA750 with gating parameters applied to further indicate positive signal measured from CD13 antigens, while remaining negative for CD34, CD17, and HLADR antigens. The plot 2606 displays the signal measured from CD33-APCA750 with gating parameters applied to further indicate positive signal measured from CD34 antigens, while remaining negative for CD13, CD117, and HLADR antigens. The plot 2608 displays the signal measured from CD33-APCA750 with gating parameters applied to further indicate positive signal measured from CD117 antigens, while remaining negative for CD13, CD34, and HLADR antigens. The plot 2610 displays the signal measured from CD33-APCA750 with gating parameters applied to further indicate positive signal measured from HLADR antigens, while remaining negative for CD13, CD34, and CD117 antigens. The plot 2612 displays the signal measured from CD33-APCA750 with gating parameters applied to further indicate positive signal measured from CD13, and HLADR antigens, while remaining negative for CD34 and CD117 antigens. The plot 2614 displays the signal measured from CD33-APCA750 with gating parameters applied to further indicate positive signal measured from CD34, CD117, and HLADR antigens, while remaining negative for CD13.

Figure 27:
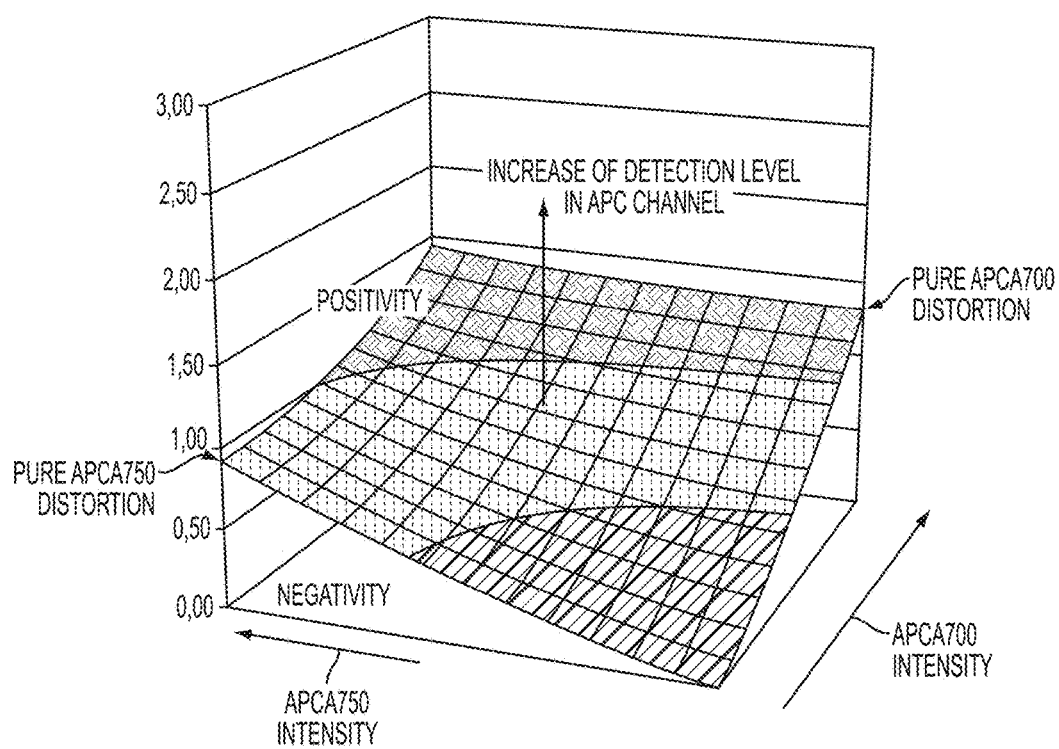
FIG. 27 depicts a three-dimensional graph modelling distortion in an PMT channel caused by the intensity of signal of two dyes that the PMT is not directed to detecting, according to embodiments.

FIG. 27 depicts aspects of a model of APCA700/A750 distortion in an APC channel, according to embodiments. The three-dimensional graph plots increasing intensity of APCA750 signal detected by an APC channel PMT, versus increasing intensity of APCA700 signal detected by the APC channel PMT, both plotted against the overall detection level measured by the APC channel PMT. At a selected reference point, for example, above 1.00 as detected by the APC channel, the event signals are predicted or calculated to be positive events. Conversely, below the selected reference point, the event signals are predicted or calculated to be negative events. At a point of maximum APCA750 intensity and zero APCA700 intensity, the event signal as measured by the APC channel is subject to "pure" or solely APCA750 distortion. Conversely, at a point of maximum APCA700 intensity and zero APCA750 intensity, the event signal as measured by the APC channel is subject to "pure" or solely APCA700 distortion. The model as shown in FIG. 27 can be expanded in further dimensions for an arbitrary number of distorting fluorochromes. Such models as shown in FIG. 27 can be used in calculations to remove the effect of event signal from distorting fluorochromes on the measurements recorded by a channel and PMT for a desired fluorophore.

FIG. 28 depicts an exemplary distortion table 2800, similar to the distortion table 2200 discussed in relation to FIG. 22A and FIG. 22B. As can be seen in distortion table 2800, the specific dyes used by a panel (or, alternatively, used in a panel design simulation) can be specifically identified. Similarly, the bandpass filter properties of the PMT channel detectors of the hardware used by an instrument measuring emission (or, alternatively, used in a panel design simulation) can be specifically identified. In aspects, the grouping of dyes of PMT channels can be based on the wavelength of the excitation laser for a given dye, however, the display of a distortion table can present the groupings of distortion values in any order that is useful or appropriate for an operator. As is evident in comparing the two distortion tables, distortion table 2200 and distortion table 2800, the identity of the PMT detectors and dyes used for any particular hardware configuration or panel design can change the distortion values used to make correction calculations.

Figure 29:
FIGS. 29-29E depict aspects of real data, plotting event data acquired from a flow cytometry instrument applying gating to the data where applicable, according to some embodiments.

FIG. 29 is a table 2900 identifying an exemplary arrangement of target antigens 2902, dyes 2904, and excitation lasers 2906 for activating the identified dyes. As indicated, the excitation lasers 2906 are operative to excite their respective dyes 2904, which are in turn conjugated with their target antigens 2902. In aspects, compensated data that is acquired using such arrangements can be exported to a processor and operable system or program, such as a 20 bit table to Excel, via software such as Kaluza 1.2 beta. Positive and negative event classification can be calculated for each event individually, particularly in the context of antibody-dye conjugates specifically evaluated. FIGS. 29A-29E depict aspects of real data according to embodiments, using the arrangement of target antigens 2902, dyes 2904, and excitation lasers 2906 as set forth in FIG. 29.

Figure 29A:
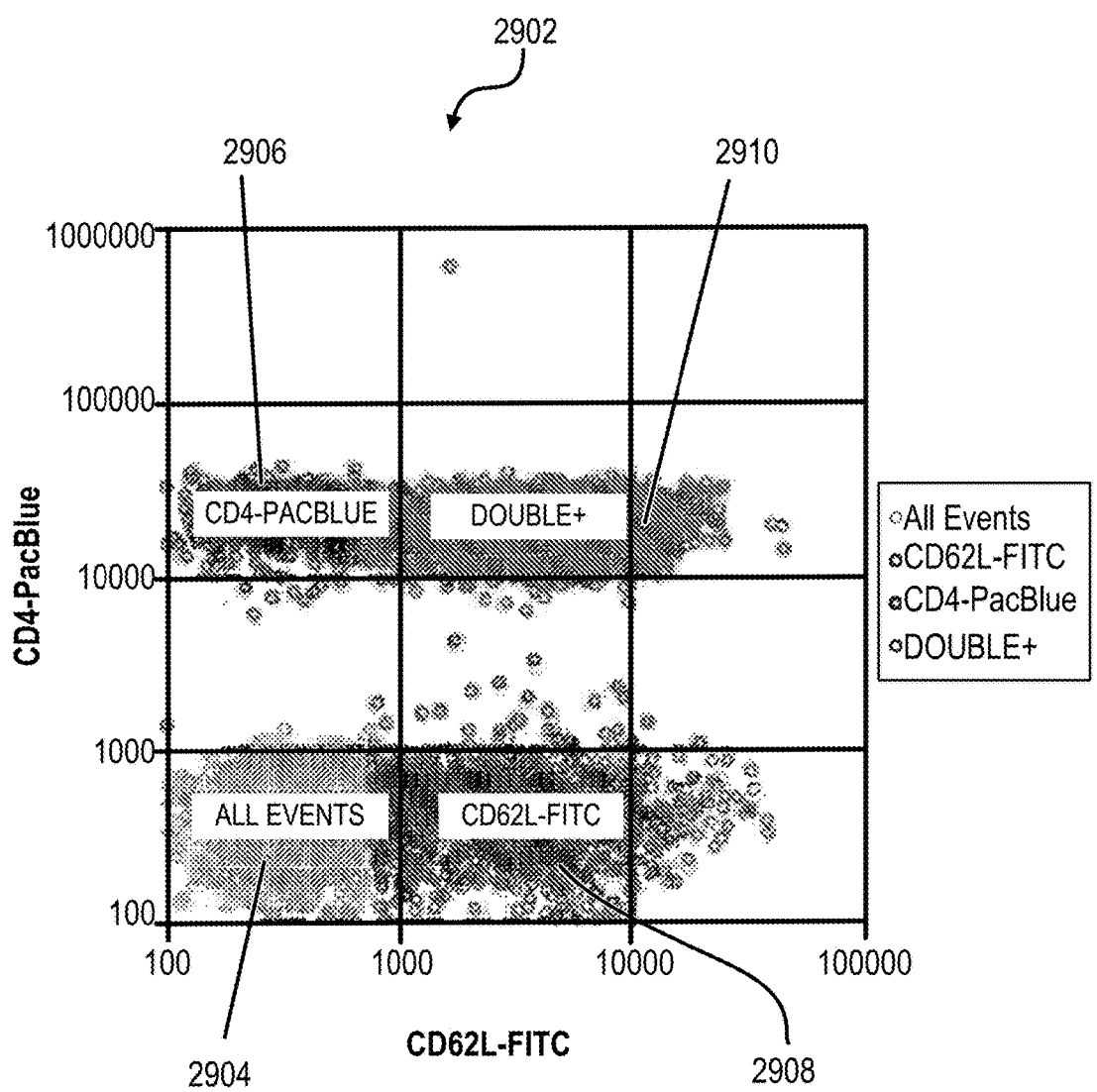

FIG. 29A depicts aspects of real data according to an embodiment of the present disclosure, particularly the plotting of event data acquired from a flow cytometry instrument, applying gating techniques for CD62L-FITC versus CD4-PacBlue event signal 2902. The plotting of CD62L-FITC versus CD4-PacBlue (Pacific Blue) event signal 2902 shows differentiation that is orthogonal, reflective of the untouched channels evaluated. Accordingly, the population of all events can be classified as distinct populations of events that are: a negative for both CD62L-FITC and CD4-PacBlue population 2904, a positive for CD62L-FITC and negative for CD4-PacBlue population 2906, a negative for both CD62L-FITC and a positive for CD4-PacBlue population 2908, and a positive for both CD62L-FITC and CD4-PacBlue population 2910.

Figure 29B:
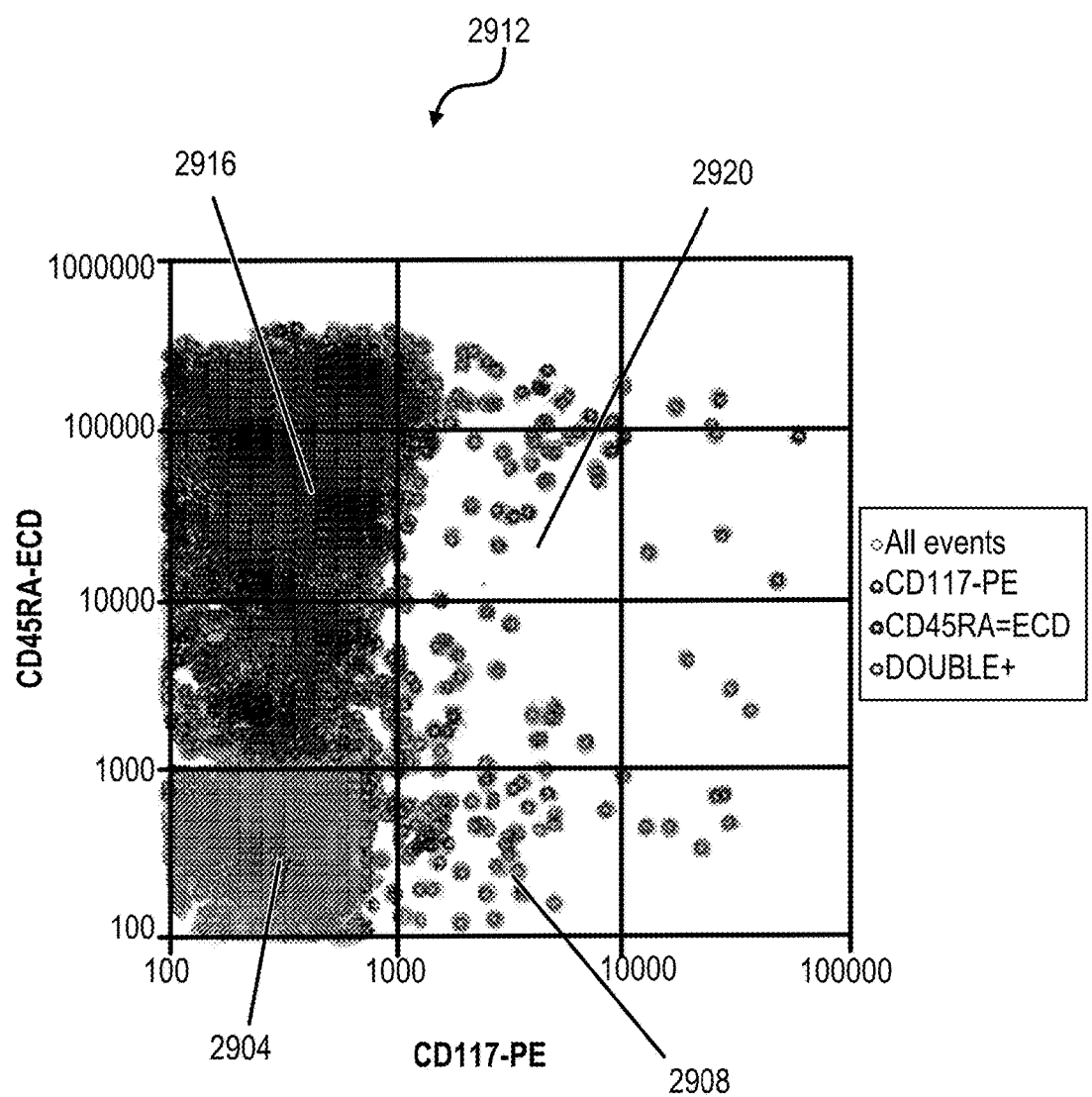

FIG. 29B depicts aspects of real data according to embodiments of the present disclosure, particularly the plotting of event data acquired from a flow cytometry instrument, applying gating techniques for CD117-PE versus CD45RA-ECD event signal 2912.

Accordingly, the population of all events can be classified as populations of events that are: a negative for both CD117-PE and CD45RA-ECD population 2914, a positive for CD117-PE and negative for CD45RA-ECD population 2916, a negative for both CD117-PE and a positive for CD45RA-ECD population 2918, and a positive for both CD117-PE versus CD45RA-ECD population 2920. The plotting of CD117-PE versus CD45RA-ECD event signal 2912 indicates at least one "hinge" that affects classification of individual events as positive or negative, reflective of the channels evaluated. A first hinge can be identified as in the region between the population of events 2914 and the population of events 2920, while a second hinge can be identified in the region between the population of events 2916 and the population of events 2920. These results can further reflect multiple superpositions of coefficients of variation (CV) between various populations.

Figure 29C:
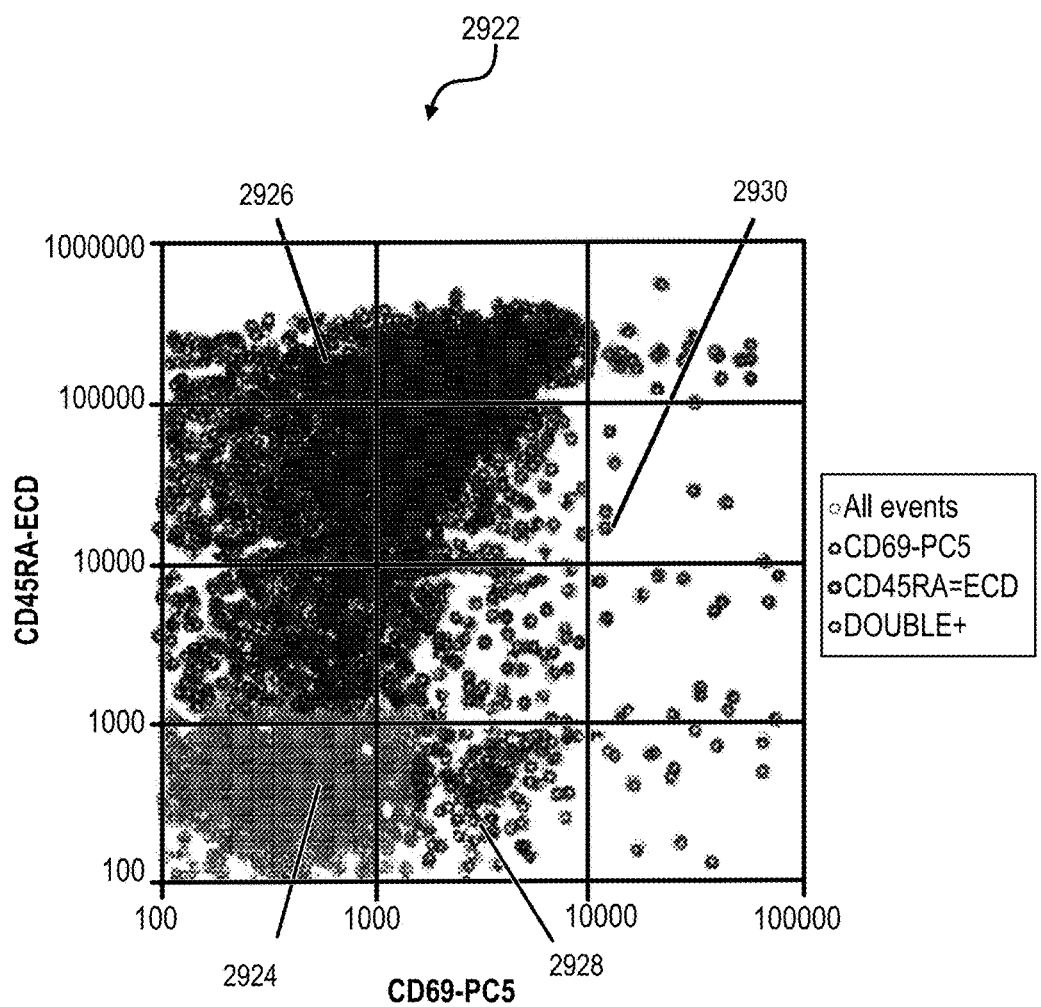

FIG. 29C depicts aspects of real data according to embodiments of the present disclosure particularly the plotting of event data acquired from a flow cytometry instrument, applying gating techniques for CD69-PC5 versus CD45RA-ECD event signal 2922. Accordingly, the population of all events can be classified as populations of events that are: a negative for both CD69-PC5 and CD45RA-ECD population 2924, a positive for CD69-PC5 and negative for CD45RA-ECD population 2926, a negative for both CD69-PC5 and a positive for CD45RA-ECD population 2928, and a positive for both CD69-PC5 versus CD45RA-ECD population 2930. The plotting of CD69-PC5 versus CD45RA-ECD event signal 2922 indicates at least one "hinge" that affects classification of individual events as positive or negative, reflective of the channels evaluated. A first hinge can be identified as in the region between the population of events 2924 and the population of events 2930, while a second hinge can be identified in the region between the population of events 2926 and the population of events 2930. These results can further reflect multiple superpositions of coefficients of variation (CV) between various populations.

Figure 29D:
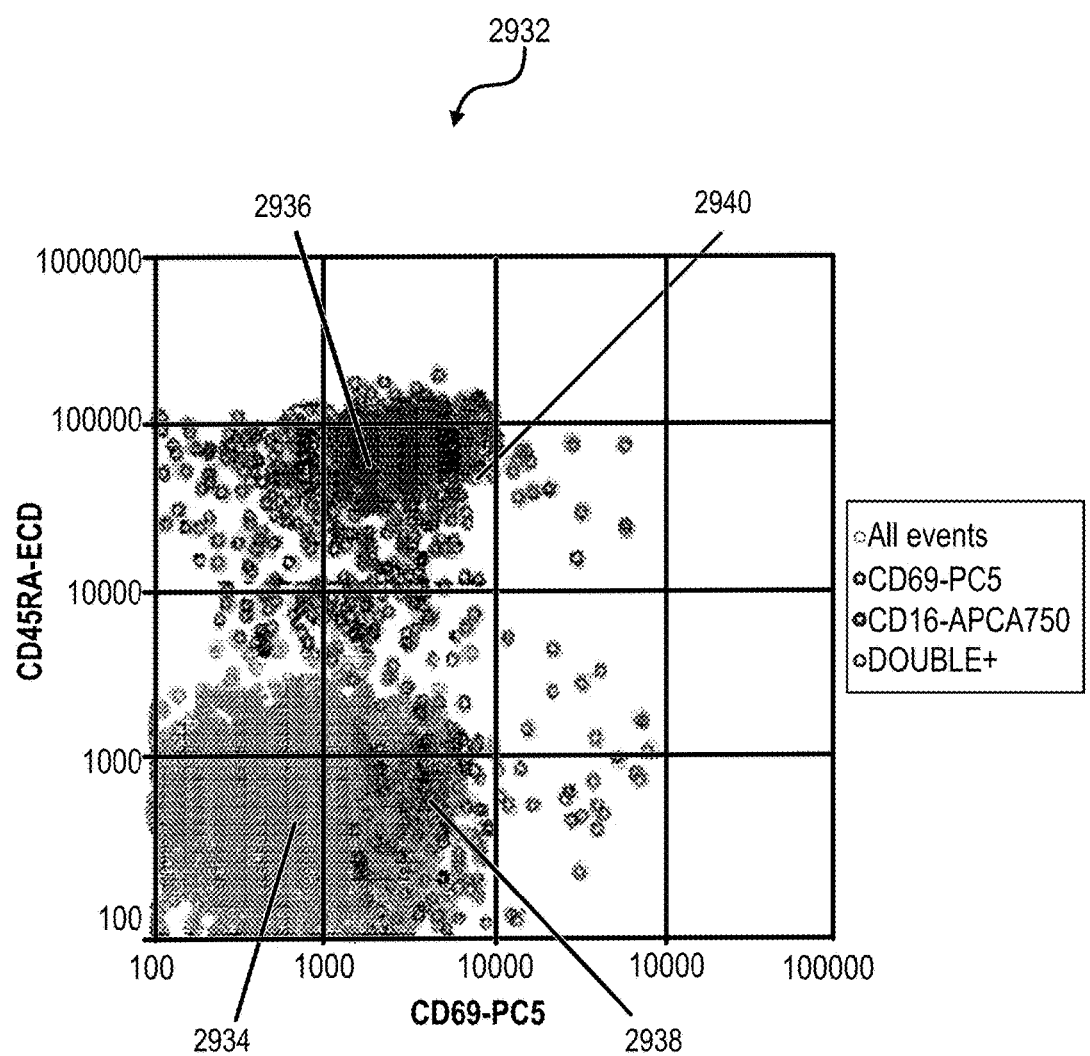

FIG. 29D depicts aspects of real data according to embodiments of the present disclosure particularly the plotting of event data acquired from a flow cytometry instrument, where the application of gating techniques may not be useful or possible. In particular, the plotting of event data acquired from a flow cytometry instrument for CD69-PC5 versus CD16-APCA750 event signal 2932 is shown. Accordingly, the population of all events can be classified as populations of events that are: a negative for both CD69-PC5 and CD16-APCA750 population 2934, a positive for CD69-PC5 and negative for CD16-APCA750 population 2936, a negative for both CD69-PC5 and a positive for CD16-APCA750 population 2938, and a positive for both CD69-PC5 versus CD16-APCA750 population 2940. The plotting of CD69-PC5 versus CD16-APCA750 event signal 2932, however, does not indicate a clear region that can define a "hinge" to reliably classify individual events as positive or negative relative to the channels evaluated. These results can reflect multiple superpositions of coefficients of variation (CV) between the various populations. Thus, in some aspects, analysis of CD69-PC5 versus CD16-APCA750 in combination may be considered ungateable, and can be avoided in further analysis or panel design.

Figure 29E:
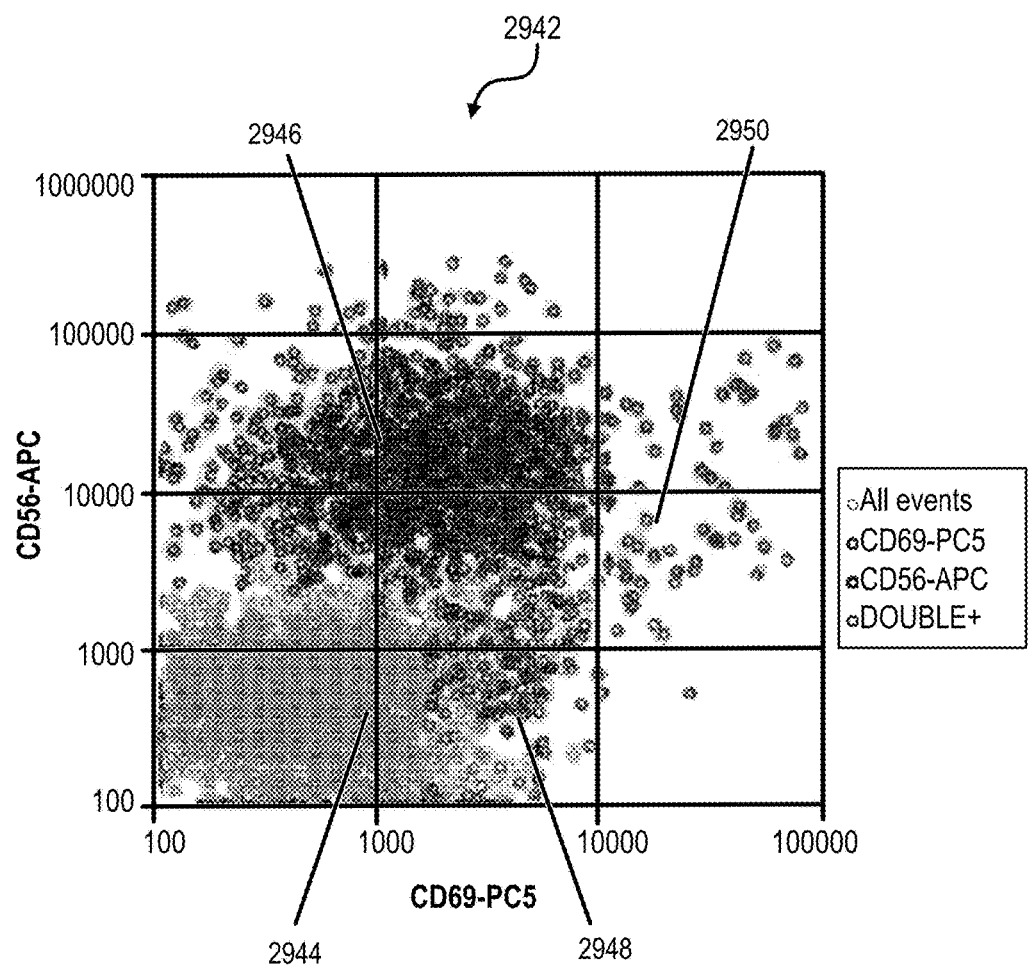

FIG. 29E depicts aspects of real data according to embodiments of the present disclosure particularly the plotting of event data acquired from a flow cytometry instrument, where the application of gating techniques may not be useful or possible. In particular, the plotting of event data acquired from a flow cytometry instrument for CD69-PC5 versus CD56-APC event signal 2942 is shown. Accordingly, the population of all events can be classified as populations of events that are: a negative for both CD69-PC5 and CD56-APC population 2944, a positive for CD69-PC5 and negative for CD56-APC population 2946, a negative for both CD69-PC5 and a positive for CD56-APC population 2948, and a positive for both CD69-PC5 versus CD56-APC population 2950. The plotting of CD69-PC5 versus CD56-APC event signal 2942, however, does not indicate a clear region that can define a "hinge" to reliably classify individual events as positive or negative relative to the channels evaluated. These results can reflect multiple superpositions of coefficients of variation (CV) between the various populations. Thus, in some aspects, analysis of CD69-PC5 versus CD56-APC in combination may be considered ungateable, and can be avoided in further analysis or panel design.

FIG. 30 is a table 3000 identifying an exemplary arrangement of target antigens 3002, dyes 3004, and excitation lasers 3006 for activating the identified dyes. As indicated, the excitation lasers 3006 are operative to excite their respective dyes 3004, which are in turn conjugated with their target antigens 3002.

Figure 30A:
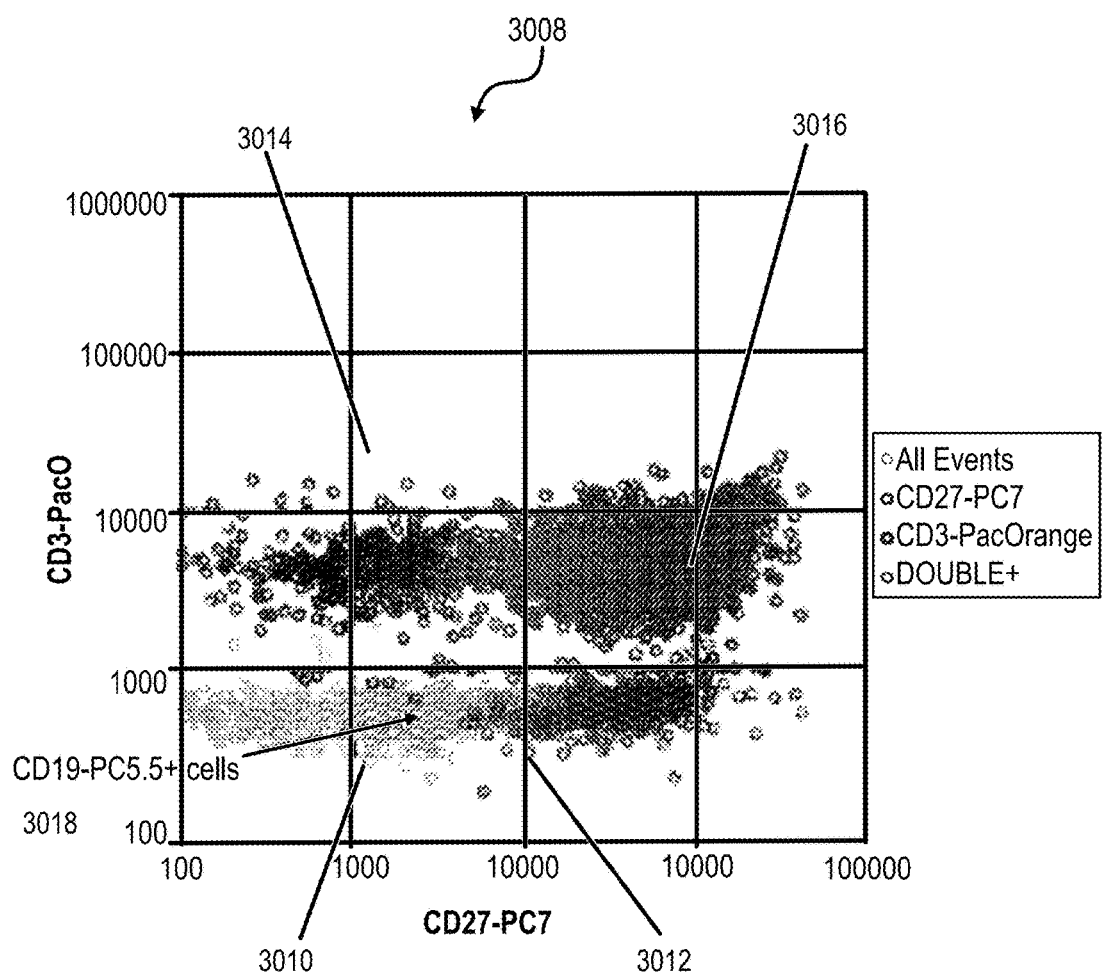

FIG. 30A depicts aspects of real data according to embodiments of the present disclosure, using the arrangement of target antigens 3002, dyes 3004, and excitation lasers 3006 as set forth in FIG. 30, particularly the plotting of event data acquired from a flow cytometry instrument. In FIG. 30A, gating techniques or algorithms are not applied, allowing for a holistic evaluation of positive and negative classification based on the PMT detection channels used to evaluate the event signals. Specifically, the plotting of event data acquired from a flow cytometry instrument for CD27-PC7 versus CD3-PacO (Pacific Orange) event signal 3008 is shown. The population of all events can be classified as populations of events that are: a negative for both CD27-PC7 and CD3-PacO population 3010, a positive for CD27-PC7 and negative for CD3-PacO population 3012, a negative for both CD27-PC7 and a positive for CD3-PacO population 3014, and a positive for both CD27-PC7 versus CD3-PacO population 3016. However, without application of a gating technique as presented in the present disclosure, a population of event signals from a different antigen-antibody conjugate may incorrectly be grouped as positive for another event signal population. For example, in FIG. 30A, an event signal population positive for CD19-PC5.5 3018 can be mistakenly grouped with the event signal positive for CD27-PC7 and negative for CD3-PacO 3012. These results again can reflect multiple superpositions of coefficients of variation (CV) between the various populations, and further reflect the errors that may arise without the application of gating techniques.

Various principles can be used and applied when predicting or determining detection limits. For example, according to some embodiments, bright dyes may work well with weakly expressed antigens, whereas both dim and bright dyes may work well with strongly expressed antigens. Further, untouched channels may work well with weakly expressed antigens, whereas silent channels may work well with strongly expressed antigens. In some cases, it may be desirable to allow for spillover between excluding antigens. In some cases, it may be desirable to avoid spillover between non-exclusively coexpressed markers. In some cases, it may be desirable to allow for spillover from subpopulation markers to parent markers. In some cases, it may be desirable to avoid spillover from parent markers to subpopulation markers or co-expressed markers to subpopulation or other co-expressed markers if the aim is to discriminate within the positive range, i.e. to discriminate prominent positive versus dim positive events. In some cases, it may be desirable to minimize the number of distorting fluorochromes per detection channel.

Various embodiments of the present disclosure are considered as follows. In aspects, the present disclosure is directed toward a method of determining a probe panel for analyzing a biological sample in a flow cytometry procedure, where the method includes: receiving information regarding a roster comprising a plurality of probes, the individual probes of the roster being associated with respective individual channel-specific detection limits; receiving information regarding an antigenic coexpression pattern; evaluating combinations of individual probes as the probe panel, based on the flow cytometer hardware configuration, the individual channel-specific detection limits, and the antigenic coexpression pattern, the combinations being subsets of probes from the roster; determining the probe panel for use with the flow cytometer hardware configuration, individual channel-specific detection limits, and antigenic coexpression pattern; and outputting a probe panel for use in a flow cytometry procedure. In some aspects, the method can further include receiving information regarding a flow cytometer hardware configuration. In other aspects, information received regarding the flow cytometer hardware configuration can include any or all of information regarding at least one excitation laser intensity, at least one excitation laser wavelength, and at least one photomultiplier tube detection channel range. In further aspects, information received regarding the roster comprising a plurality of probes further can involve any or all of accessing a non-transitory computer-readable medium having a library of channel-specific detection limits for the plurality of probes, an operator selecting an antibody and a corresponding dye as at least one member of the probe panel, automatically selecting an antibody and a corresponding dye from a library as at least one member of the probe panel, and a automatically selecting an antibody and a corresponding dye from a library for each member of the probe panel. In some embodiments, the roster can include one or more dummy members. In some aspects, receiving information regarding the antigenic coexpression pattern can include accessing a non-transitory computer-readable medium having a library of coexpression relationships. In yet further aspects, evaluating combinations of individual probes as the probe panel can include calculating any overlap or distortion between channel-specific detection limits of two or more individual probes. In some aspects, the antigenic coexpression pattern can include coexpression relationships between antigens for a particular cell type.

Further embodiments of the present disclosure can be directed toward a system for determining a probe panel for analyzing a biological sample in a flow cytometry procedure, where the system can include: an information input device; a flow cytometer with a hardware configuration having at least one excitation laser and at least one photomultiplier tube detector; a probe library stored in a database, where individual probes of the library are associated with respective individual channel-specific detection limits; an antigenic coexpression pattern stored in the database; a processor configured to evaluate a roster of individual probes selected from the probe library based on the flow cytometer hardware configuration, the channel-specific detection limits of the individual probes, and the antigenic coexpression pattern; and an output device providing a determination of detection limits for the probe panel, the probe panel comprising a subset of individual probes from the roster. In aspects, the flow cytometer hardware configuration of the system can include up to ten photomultiplier tube detectors, although in other embodiments the flow cytometer hardware configuration can have more than ten photomultiplier tube detectors. In other aspects, the flow cytometer hardware configuration of the system can also include up to four excitation lasers, although in other embodiments the flow cytometer hardware configuration can have more than four excitation lasers. In some aspects, wherein the information input device can be configurable to allow any or all of: an operator to select individual probes from the probe library for evaluation in the roster, an operator to input channel-specific detection limits for individual probes into the probe library, the processor to automatically select an antibody and a corresponding dye from the probe library for each member of the probe panel. In further aspects, the processor evaluating combinations can calculate any overlap or distortion between channel-specific detection limits of two or more individual probes.

Further embodiments of the present disclosure are directed toward a method of analyzing a biological sample in a flow cytometry procedure, where the method includes: measuring the light output of a plurality of probes in a biological sample with a flow cytometer; receiving information regarding a flow cytometer hardware configuration; receiving information regarding a roster comprising a plurality of probes used in the biological sample, the individual probes of the roster being associated with respective individual channel-specific detection limits; receiving information regarding an antigenic coexpression pattern; determining a positivity criteria and a negativity criteria for each individual probe in the roster and determining gating parameters for the roster, based on the flow cytometer hardware configuration, the individual channel-specific detection limits, and the antigenic coexpression pattern; and evaluating the light output of the plurality of probes in the biological sample according to the positivity criteria, negativity criteria, and gating parameters. In aspects, receiving information regarding the flow cytometer hardware configuration further includes receiving information regarding at least one excitation laser intensity, at least one excitation laser wavelength, and at least one photomultiplier tube detection channel range. In some aspects, receiving information regarding the roster comprising a plurality of probes can further include either or both of accessing a non-transitory computer-readable medium having a library of channel-specific detection limits for the plurality of probes and an operator selecting an antibody and a corresponding dye for the plurality of probes. In further aspects, the roster can include one or more dummy members. In some aspects, receiving information regarding the antigenic coexpression pattern further can include accessing a non-transitory computer-readable medium having a library of coexpression relationships. In other aspects, the evaluation of combinations of individual probes as the probe panel can include calculating any overlap or distortion between channel-specific detection limits of two or more individual probes. In yet other aspects, the antigenic coexpression pattern can include coexpression relationships between antigens for a particular cell type.

Further embodiments of the present disclosure can be directed toward a system for analyzing a biological sample in a flow cytometry procedure, where the system can include: an operator input device, though which a roster comprising a plurality of probes used in a biological sample can be input; a flow cytometer hardware configuration having at least one excitation laser and at least one photomultiplier tube detector; a probe library stored in a database, where individual probes of the library are associated with respective individual channel-specific detection limits; an antigenic coexpression pattern stored in the database; a processor configured to evaluate light emitted by the plurality of probes and detected by the at least one photomultiplier tube detector, calculate any overlap and distortion between channel-specific detection limits the plurality of probes; and an output device providing a determination the presence or absence of a probe in the biological sample. In some aspects, the system can have a flow cytometer hardware configuration that includes up to ten photomultiplier tube detectors. In other aspects, the system can have a flow cytometer hardware configuration that includes up to four excitation lasers. In further aspects, the system can include an operator input device that is configurable to allow an operator to select individual probes from the probe library for evaluation in the roster, or that is configurable to allow an operator to input channel-specific detection limits for individual probes into the probe library.

Further embodiments of the present disclosure can be directed toward a method for determining a probe panel for analyzing a biological sample in a flow cytometry procedure including: providing a selection of flow cytometry hardware configurations; providing a plurality of selections of antibody pairings; providing a selection of at least one target population; providing a selection for a plurality of antibodies, and providing at least one selection to indicate if an antibody of the plurality of antibodies is an antigen of interest or an unrelated antigen; providing a plurality of a selection of antigen-antibody pairings, and for an individual antigen-antibody paring, providing a selection of antigens to which the individual antigen-antibody paring is mutually excluding; providing a plurality of a selection of antigen-antibody pairings, and for an individual antigen-antibody paring, providing a selection of antigens that are developmental descendants of the individual antigen-antibody paring; providing a selection of adjustable antigen density parameters; and responsive to the selection of a selection of flow cytometry hardware configurations, a plurality of selections of antibody pairings, a selection of at least one target population, a selection for a plurality of antibodies, a selection of antigens to which at least one antigen-antibody paring is mutually excluding, a selection of antigens that are developmental descendants of at least one antigen-antibody paring, and a selection of adjustable antigen density parameters, providing a display of detection limit estimates for the probe panel. In embodiments, providing a plurality of selections of antibody pairings can further include providing a selection of selectivity for each antibody pairing and providing a section of dye for each antibody paring. In aspects, providing a selection of at least one target population can include providing a selection corresponding to a phenotype of the target population. In some aspects, providing a selection of at least one target population is configurable to allow for the addition or removal of target populations. In some aspects, the selection of antigens to which an individual antigen-antibody paring is mutually excluding can be automatically determined by a mutual exclusion database, and the selection of antigens to which an individual antigen-antibody paring is mutually excluding is automatically selected. In other aspects, a selection of antigens that are developmental descendants of individual antigen-antibody paring can be automatically determined by a developmental family pattern database, and the selection of antigens that are developmental descendants of the individual antigen-antibody paring is automatically selected. In some aspects, the provided adjustable antigen density parameters can include a selection to discriminate in the display between positive and negative detection limit estimates, while in other aspects, the provided adjustable antigen density parameters can include a selection to discriminate in the display between bright positive and dim positive detection limit estimates. In further aspects, the provided adjustable antigen density parameters include a selection to display either discrete or modulated detection limit estimates, while in yet further aspects, the provided adjustable antigen density parameters include a selection to scale the display according to an estimated detection limit of the probe panel.

Each of the calculations or operations described herein may be performed using a computer, communication network, or other processor having hardware, software, and/or firmware. An exemplary system with attendant computer, communication network, or other processor having hardware, software, and/or firmware can be found in U.S. patent application Ser. No. 13/935,154, which is hereby incorporated by reference. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

It is appreciated that a flow cytometry system as described herein can be configured to carry out various aspects of methods of the present invention. For example, a processor component or module of a system can be a microprocessor control module configured to receive cellular parameter signals from a sensor input device or module, from a user interface input device or module, and/or from an analyzer system, optionally via an analyzer system interface and/or a network interface and a communication network. In some instances, sensor input device(s) may include or be part of a cellular analysis system such as a flow cytometer. In some instances, user interface input device(s) and/or network interface may be configured to receive cellular parameter signals generated by a cellular analysis system such as a flow cytometer. In some instances, analyzer system may include or be part of a cellular analysis system such as a flow cytometer.

Processor component or module can also be configured to transmit cellular parameter signals, optionally processed according to any of the techniques disclosed herein, to a sensor output device or module, to a user interface output device or module, to a network interface device or module, to an analyzer system interface, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, Macintosh, and Unix, along with any of a variety of commonly used programming languages, may be used to implement embodiments of the present invention.

User interface input devices may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices may also download a computer executable code from a tangible storage media or from communication network, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system.

User interface output devices may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system to a user.

A bus subsystem can provide a mechanism for letting the various components and subsystems of module system communicate with each other as intended or desired. The various subsystems and components of module system need not be at the same physical location but may be distributed at various locations within a distributed network. A bus subsystem can be a single bus or may utilize multiple busses.

A network interface can provide an interface to an outside network or other devices. Outside communication network can be configured to effect communications as needed or desired with other parties. In many embodiments, the communication network can be a web-based or cloud-based processing system, allowing for remote access and processing. It can thus receive an electronic packet from module system and transmit any information as needed or desired back to module system. In addition to providing such infrastructure communications links internal to the system, a communications network system may also provide a connection to other networks such as the internet and may comprise a wired, wireless, modem, and/or other type of interfacing connection.

All patents, patent publications, patent applications, journal articles, books, technical references, and the like discussed in the instant disclosure are incorporated herein by reference in their entirety for all purposes.

It is to be understood that the figures and descriptions of the invention have been simplified to illustrate elements that are relevant for a clear understanding of the invention. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A method of designing a probe panel for differentiating populations of particles in a sample using a flow cytometer, the method comprising:
   determining a distortion factor that quantifies spillover effect caused by emission of a first label, intended to be measured in a first channel, into a second channel;
   determining a maximum expected signal of a first probe-label combination including the first label and a first probe, wherein the first probe binds to a first antigen associated with a population of particles of interest in the sample, and wherein the maximum expected signal is determined based on a brightness of the first label and a density of the first antigen on or inside the particles of interest in the sample;
   calculating in a detection limit of a second antigen detected in the second channel, wherein calculating the detection limit comprises multiplying the distortion factor by the maximum expected signal of the first probe-label combination, and wherein the detection limit is a threshold of signal intensity dividing particles considered to be positive for the second antigen from particles considered to be negative for the second antigen;
   selecting a probe-label combination to include in the probe panel based on the calculated detection limit; and
   differentiating the populations of particles in the sample using the probe panel in the flow cytometer.

2. The method of claim 1, wherein the distortion factor is an estimate of an increase in detection limit of the second antigen in the second channel as a function of an emission intensity of the first probe-label combination.

3. The method of claim 2, wherein the increase in detection limit of the second antigen in the second channel is caused by an increase in a measurement error as a function of the emission intensity of the first probe-label combination.

4. The method of claim 2, wherein the distortion factor is calculated using a crosstalk index.

5. The method of claim 1 wherein the distortion factor is mathematically modified by a coefficient representing a coexpression pattern of the first and second antigens.

6. The method of claim 1 further comprising:
   determining a distortion factor for each label in a first potential probe panel to calculate a total increase in detection limit in the second channel.

7. The method of claim 6, wherein selecting the probe-label combination is based on a comparison of the calculated total increase in detection limit with an expected minimum signal of a second probe-label combination, corresponding to the second antigen, in the second channel.

8. The method of claim 6, further comprising calculating a total increase in detection limit for each probe in the first potential probe panel.

9. The method of claim 8, further comprising:
calculating a total increase in detection limit for each probe in a second potential probe panel; and
selecting the probe panel based on a comparison of the calculated total increase in detection limit for each probe in the first potential probe panel with the calculated total increase in detection limit for each probe in the second potential probe panel.

10. The method of claim 8, further comprising:
calculating a total increase in detection limit for each probe in a second potential probe panel; and
selecting the probe panel based on the calculated total increase in detection limit for a prioritized probe in the first potential probe panel and the second potential probe panel.

11. A method of designing a probe panel for differentiating populations of particles in a sample using a flow cytometer, the method comprising:
determining a distortion factor that quantifies spillover effect caused by emission of a first label, intended to be measured in a first channel, into a second channel;
determining a maximum expected signal of a first probe-label combination including the first label and a first probe, wherein the first probe binds to a first antigen associated with a population of particles of interest in the sample, and wherein the maximum expected signal is a function of a brightness of the first label and an expression pattern of the first antigen;
calculating a detection limit of a second antigen detected in the second channel, wherein calculating the detection limit comprises multiplying the distortion factor by the maximum expected signal of the first probe-label combination, and wherein the detection limit is a threshold of signal intensity dividing particles considered to be positive for the second antigen from particles considered to be negative for the second antigen;
selecting a probe-label combination to include in the probe panel based on the calculated detection limit; and
differentiating the populations of particles in the sample using the probe panel in the flow cytometer.

12. The method of claim 11, wherein the expression pattern of the first antigen includes a mean density of the first antigen on or inside the particles of interest in the sample.

13. The method of claim 11, wherein the expression pattern of the first antigen includes a range of expression of the first antigen in the particles of interest in the sample.

14. The method of claim 11, wherein the distortion factor is mathematically modified by a coefficient representing a coexpression pattern of the first and second antigens.

15. The method of claim 14, wherein the coefficient is either one or zero.

16. The method of claim 15, wherein the coefficient is zero if the coexpression pattern of the first and second antigens is mutually exclusive.

17. The method of claim 15, wherein the coefficient is zero if the first antigen is a descendent of the second antigen.

18. A method of designing a probe panel for differentiating populations of particles in a sample using a flow cytometer, the method comprising:
determining a distortion factor that quantifies spillover effect caused by emission of a first label, intended to be measured in a first channel, into a second channel;
determining a maximum expected signal of a first probe-label combination including the first label and a first probe, wherein the first probe binds to a first antigen associated with a population of particles of interest in the sample, and wherein the maximum expected signal is a function of the brightness of the first label and an expression pattern of the first antigen;
calculating a detection limit of a second antigen detected in the second channel using a second probe-label combination including a second label and a second probe corresponding to the second antigen, wherein calculating the detection limit comprises multiplying the distortion factor by the maximum expected signal of the first probe-label combination, and wherein the detection limit is represented as a slope of a graph of emission measured in the second channel as a function of emission measured in the first channel;
selecting a probe-label combination to include in the probe panel based on the calculated detection limit; and
differentiating the populations of particles in the sample using the probe panel in the flow cytometer.

19. The method of claim 18, wherein calculating the detection limit is based on a linear superpositioning model of CV enlargements.

20. The method of claim 18, wherein the distortion factor is a measure of CV enlargements caused by color compensation.

* * * * *